US009738727B2

(12) United States Patent
Wu et al.

(10) Patent No.: US 9,738,727 B2
(45) Date of Patent: Aug. 22, 2017

(54) ANTI-HTRA1 ANTIBODIES AND METHODS OF USE

(71) Applicant: Genentech, Inc., South San Francisco, CA (US)

(72) Inventors: Yan Wu, Foster City, CA (US); Menno van Lookeren-Campagne, San Francisco, CA (US); Daniel Kirchhofer, Los Altos, CA (US); Michael Terry Lipari, Santa Clara, CA (US); Kenneth J. Katschke, Jr., Fairfield, CA (US); Paul M. Moran, El Cerrito, CA (US); Scott Stawicki, San Francisco, CA (US); Wei-Ching Liang, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 1010 days.

(21) Appl. No.: 13/651,289

(22) Filed: Oct. 12, 2012

(65) Prior Publication Data

US 2013/0129743 A1    May 23, 2013

Related U.S. Application Data

(60) Provisional application No. 61/547,649, filed on Oct. 14, 2011.

(51) Int. Cl.
*C07K 16/40* (2006.01)

(52) U.S. Cl.
CPC .......... *C07K 16/40* (2013.01); *C07K 2317/34* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. |
| 4,376,110 A | 3/1983 | David et al. |
| 4,469,863 A | 9/1984 | Ts'o et al. |
| 4,476,301 A | 10/1984 | Imbach et al. |
| 4,485,045 A | 11/1984 | Regen |
| 4,486,530 A | 12/1984 | David et al. |
| 4,522,811 A | 6/1985 | Eppstein et al. |
| 4,544,545 A | 10/1985 | Ryan et al. |
| 4,816,567 A | 3/1989 | Cabilly et al. |
| 4,845,205 A | 7/1989 | Huynh Dinh et al. |
| 4,868,105 A | 9/1989 | Urdea et al. |
| 4,981,957 A | 1/1991 | Lebleu et al. |
| 5,013,556 A | 5/1991 | Woodle et al. |
| 5,023,243 A | 6/1991 | Tullis |
| 5,034,506 A | 7/1991 | Summerton et al. |
| 5,047,335 A | 9/1991 | Paulson et al. |
| 5,093,246 A | 3/1992 | Cech et al. |
| 5,118,800 A | 6/1992 | Smith et al. |
| 5,130,302 A | 7/1992 | Spielvogel et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,299 A | 1/1994 | Wong et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,367,066 A | 11/1994 | Urdea et al. |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |

(Continued)

FOREIGN PATENT DOCUMENTS

EP    0073675 A1    3/1983
EP    0225807 B1    6/1987

(Continued)

OTHER PUBLICATIONS

By Rudikoff et al. (Proc Natl Acad Sci USA 1982 vol. 79 p. 1979).*
MacCallum et al. (J. Mol. Biol. 1996 262, 732-745).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Ali et al. "Epidemiology and Biology of Insulin-like Growth Factor Binding Protein-3 (IGFBP-3) as an Anti-Cancer Molecule." Database Accession No. PREV200400113781, Hormone and Metabolic Research. 35(11-12):726-33 (2003).
Atlschul et al., "Basic local alignment search tool," J Mol Biol. 215(3): 403-10 (1990).
Altschul et al., "Gapped BLAST and PSI-BLAST: a new generation of protein database search programs," Nucleic Acids Res. 25(17):3389-402 (1997).

(Continued)

*Primary Examiner* — Sharon Wen
(74) *Attorney, Agent, or Firm* — Clark & Elbing LLP; Karen L. Elbing

(57) ABSTRACT

The invention provides anti-HtrA1 antibodies and methods of using the same.

33 Claims, 22 Drawing Sheets

(56) References Cited

U.S. PATENT DOCUMENTS

| | | | |
|---|---|---|---|
| 5,489,677 A | 2/1996 | Sanghvi et al. |
| 5,502,177 A | 3/1996 | Matteucci et al. |
| 5,510,261 A | 4/1996 | Goochee et al. |
| 5,514,785 A | 5/1996 | Van Ness et al. |
| 5,519,126 A | 5/1996 | Hecht |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,545,806 A | 8/1996 | Lonberg et al. |
| 5,545,807 A | 8/1996 | Surani et al. |
| 5,550,111 A | 8/1996 | Suhadolnik et al. |
| 5,561,225 A | 10/1996 | Maddry et al. |
| 5,563,253 A | 10/1996 | Agrawal et al. |
| 5,567,811 A | 10/1996 | Misiura et al. |
| 5,569,825 A | 10/1996 | Lonberg et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,618,704 A | 4/1997 | Sanghvi et al. |
| 5,623,070 A | 4/1997 | Cook et al. |
| 5,625,050 A | 4/1997 | Beaton et al. |
| 5,625,126 A | 4/1997 | Lonberg et al. |
| 5,627,053 A | 5/1997 | Usman et al. |
| 5,633,425 A | 5/1997 | Lonberg et al. |
| 5,639,873 A | 6/1997 | Barascut et al. |
| 5,646,265 A | 7/1997 | McGee |
| 5,652,094 A | 7/1997 | Usman et al. |
| 5,658,873 A | 8/1997 | Bertsch-Frank et al. |
| 5,661,016 A | 8/1997 | Lonberg et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,698,046 A | 12/1997 | St. Laurent et al. |
| 5,700,920 A | 12/1997 | Altmann et al. |
| 5,714,331 A | 2/1998 | Buchardt et al. |
| 5,739,277 A | 4/1998 | Presta et al. |
| 5,741,713 A | 4/1998 | Brown et al. |
| 5,750,373 A | 5/1998 | Garrard et al. |
| 5,750,692 A | 5/1998 | Cook et al. |
| 5,800,998 A | 9/1998 | Glucksmann |
| 5,837,492 A | 11/1998 | Tavtigian et al. |
| 5,891,628 A | 4/1999 | Reeders et al. |
| 6,004,794 A | 12/1999 | Karran et al. |
| 6,261,801 B1 | 7/2001 | Wei et al. |
| 6,274,376 B1 | 8/2001 | Black et al. |
| 6,274,720 B1 | 8/2001 | Lal et al. |
| 6,943,241 B2 | 9/2005 | Isogai et al. |
| 7,972,787 B2 | 7/2011 | Deangelis |
| 2005/0059002 A1 | 3/2005 | Nie et al. |
| 2010/0129358 A1 | 5/2010 | Zhang et al. |
| 2010/0166743 A1 | 7/2010 | Zhang et al. |

FOREIGN PATENT DOCUMENTS

| | | |
|---|---|---|
| EP | 0332435 B2 | 9/1989 |
| EP | 0519463 A1 | 12/1992 |
| WO | WO-84/03564 A1 | 9/1984 |
| WO | WO-91/03162 A1 | 3/1991 |
| WO | WO-92/07065 A1 | 4/1992 |
| WO | WO-93/06213 A1 | 4/1993 |
| WO | WO-93/15187 A1 | 8/1993 |
| WO | WO-99/07409 A1 | 2/1999 |
| WO | WO-99/32619 A1 | 7/1999 |
| WO | WO-99/55885 A2 | 11/1999 |
| WO | WO-00/01846 A2 | 1/2000 |
| WO | WO-00/08134 A2 | 2/2000 |
| WO | WO-00/44895 A1 | 8/2000 |
| WO | WO-00/44914 A1 | 8/2000 |
| WO | WO-01/29058 A1 | 4/2001 |
| WO | WO-01/36646 A1 | 5/2001 |
| WO | WO-2006/133295 A2 | 12/2006 |
| WO | WO-2008/067040 A2 | 6/2008 |
| WO | WO-2008/094370 A2 | 8/2008 |
| WO | WO-2008/101160 A2 | 8/2008 |
| WO | WO-2008/103299 A2 | 8/2008 |
| WO | WO-2009/046405 A2 | 4/2009 |

OTHER PUBLICATIONS

Bach et al., Monoclonal Antibodies in Diagnostic Pathology. *Handbook of Monoclonal Antibodies*. Soldano Ferrone and Manfred P. Dierich, 303-59, 419-35 (1985).

Barbas et al., "In vitro evolution of a neutralizing human antibody to human immunodeficiency virus type 1 to enhance affinity and broaden strain cross-reactivity," Proc Natl Acad Sci U S A. 91(9):3809-13 (1994).

Bartel, et al., 7: Using the two-hybrid system to detect protein-protein interactions. *Cellular Interactions in Development: A Practical Approach*. David A. Hartley, Oxford University Press, 153-179 (1993).

Beaucage et al., "Deoxynucleoside phosphoramidites—a new class of key intermediates for deoxypolynucleotide synthesis," Tetrahedron Lett. 22(20):1859-62 (1981).

Bird et al., "An international classification and grading system for age-related maculopathy and age-related macular degeneration. The International ARM Epidemiological Study Group," Surv Ophthalmol. 39(5):367-74 (1995).

Boerner et al., "Production of antigen-specific human monoclonal antibodies from in vitro-primed human splenocytes," J Immunol. 147(1):86-95 (1991).

Borchardt et al., "Synthetic receptor binding elucidated with an encoded combinatorial library," J Am Chem Soc. 116(1):373-374 (1994).

Borman, "DNA Chips Come of Age," Chemical & Engineering News. 74(50):42-3 (1996) (3 pages).

Boyd et al., "The effect of the removal of sialic acid, galactose and total carbohydrate on the functional activity of Campath-1H," Mol Immunol. 32(17-18):1311-8 (1995).

Brennan et al., "Preparation of bispecific antibodies by chemical recombination of monoclonal immunoglobulin G1 fragments," Science. 229(4708):81-3 (1985).

Brodeur et al., Mouse-Human Myeloma Partners for the Production of Heterohybridomas. *Monoclonal Antibody Production Techniques and Applications*. Lawrence B. Schook, University of Illinois, 51-63 (1987).

Burnham, "Polymers for delivering peptides and proteins," Am J Hosp Pharm. 51(2):210-8 (1994).

Capecchi, "Altering the genome by homologous recombination," Science. 244(4910):1288-92 (1989).

Cariello et al., "Resolution of a missense mutant in human genomic DNA by denaturing gradient gel electrophoresis and direct sequencing using in vitro DNA amplification: HPRT Munich," Am J Hum Genet. 42(5):726-34 (1988).

Carrillo et al., "The mutiple sequence alignment problem in biology," SIAM J Appl Math. 48(5):1073-82 (1988).

Carter et al., "High level *Escherichia coli* expression and production of a bivalent humanized antibody fragment," Biotechnology (N Y). 10(2):163-7 (1992).

Chee et al., "Accessing genetic information with high-density DNA arrays," Science. 274(5287):610-4 (1996).

Chevray et al., "Protein interaction cloning in yeast: identification of mammalian proteins that react with the leucine zipper of Jun," Proc Natl Acad Sci U S A. 89(13):5789-93 (1992).

Chothia et al., "Domain association in immunoglobulin molecules. The packing of variable domains," J Mol Biol. 186(3):651-63 (1985).

(56) References Cited

OTHER PUBLICATIONS

Clackson et al., "Making antibody fragments using phage display libraries," Nature. 352(6336):624-8 (1991).
Cole et al., The EBV-Hybridoma Technique and Its Application to Human Lung Cancer. *Monoclonal Antibodies and Cancer Therapy.* Alan R. Liss, Inc. 77-96 (1985).
Conner et al., "Detection of sickle cell beta S-globin allele by hybridization with synthetic oligonucleotides," Proc Natl Acad Sci U S A. 80(1):278-82 (1983).
Cotton et al., "Reactivity of cytosine and thymine in single-base-pair mismatches with hydroxylamine and osmium tetroxide and its application to the study of mutations," Proc Natl Acad Sci U S A. 85(12):4397-401 (1988).
Cunningham et al., "High-resolution epitope mapping of hGH-receptor interactions by alanine-scanning mutagenesis," Science. 244(4908):1081-5 (1989).
David et al., "Protein iodination with solid state lactoperoxidase," Biochemistry. 13(5):1014-21 (1974).
Dejneka et al., "Systemic rapamycin inhibits retinal and choroidal neovascularization in mice," Mol Vis. 10:964-72 (2004).
DeRisi et al., "Use of a cDNA microarray to analyse gene expression patterns in human cancer," Nat Genet. 14(4):457-60 (1996).
Devereux et al., "A comprehensive set of sequence analysis programs for the VAX," Nucleic Acids Res. 12(1 Pt 1):387-95 (1984).
Dewan et al., "HTRA1 promoter polymorphism in wet age-related macular degeneration," Science. 314(5801):989-92 (2006).
Donehower et al., "Mice deficient for p53 are developmentally normal but susceptible to spontaneous tumours," Nature. 356(6366):215-21 (1992).
Edwards et al., "Complement factor H polymorphism and age-related macular degeneration," Science. 308(5720):421-4 (2005).
Elbashir et al., "Duplexes of 21-nucleotide RNAs mediate RNA interference in cultured mammalian cells," Nature. 411(6836):494-8 (2001).
Eppstein et al., "Biological activity of liposome-encapsulated murine interferon gamma is mediated by a cell membrane receptor," Proc Natl Acad Sci U S A. 82(11):3688-92 (1985).
Feil et al., "Ligand-activated site-specific recombination in mice," Proc Natl Acad Sci U S A. 93(20):10887-90 (1996).
Fields et al., "A novel genetic system to detect protein-protein interactions," Nature. 340(6230):245-6 (1989).
Finkelstein et al., "Use of denaturing gradient gel electrophoresis for detection of mutation and prospective diagnosis in late onset ornithine transcarbamylase deficiency," Genomics. 7(2):167-72 (1990).
Fishwild et al., "High-avidity human IgG kappa monoclonal antibodies from a novel strain of minilocus transgenic mice," Nat Biotechnol. 14(7):845-51 (1996).
Fodor, "Massively parallel genomics," Science. 277(5324):393, 395 (1997).
Fu et al., "The R345W mutation in EFEMP1 is pathogenic and causes AMD-like deposits in mice," Hum Mol Genet. 16(20):2411-22 (2007).
Fuh et al., "Structure-function studies of two synthetic anti-vascular endothelial growth factor Fabs and comparison with the Avastin Fab," J Biol Chem. 281(10):6625-31 (2006).
Gagneten et al., "Brief expression of a GFP cre fusion gene in embryonic stem cells allows rapid retrieval of site-specific genomic deletions," Nucleic Acids Res. 25(16):3326-31 (1997).
Goding, Nature of Antigens; Antibody Structure and Function; Genetics of Antibodies. *Monoclonal Antibodies: Principles and Practice: Production and Application of Monoclonal Antibodies in Cell Biology, Biochemistry and Immunology, Third Edition.* Academic Press Limited, 58-103 (1996).
Godowski et al., "Signal transduction and transcriptional regulation by glucocorticoid receptor-LexA fusion proteins," Science. 241(4867):812-6 (1988).
Griffiths et al., "Human anti-self antibodies with high specificity from phage display libraries," EMBO J. 12(2):725-34 (1993).
Grompe, "The rapid detection of unknown mutations in nucleic acids," Nat Genet. 5(2):111-7 (1993).
Grompe et al., "Scanning detection of mutations in human ornithine transcarbamoylase by chemical mismatch cleavage," Proc Natl Acad Sci U S A. 86(15):5888-92 (1989).
Hacia et al., "Detection of heterozygous mutations in BRCA1 using high density oligonucleotide arrays and two-colour fluorescence analysis," Nat Genet. 14(4):441-7 (1996).
Hannon, "RNA interference," Nature. 418(6894):244-51 (2002).
Hasty et al., "Introduction of a subtle mutation into the Hox-2.6 locus in embryonic stem cells," Nature. 350(6315):243-6 (1991).
Hawkins et al., "Selection of phage antibodies by binding affinity. Mimicking affinity maturation," J Mol Biol. 226(3):889-96 (1992).
Hoogenboom et al., "By-passing immunisation. Human antibodies from synthetic repertoires of germline VH gene segments rearranged in vitro," J Mol Biol. 227(2):381-8 (1992).
Hsu et al., "Differential N-glycan patterns of secreted and intracellular IgG produced in Trichoplusia ni cells," J Biol Chem. 272(14):9062-70 (1997).
Hunter et al., "Preparation of iodine-131 labelled human growth hormone of high specific activity," Nature. 194:495-6 (1962).
Hwang et al., "Hepatic uptake and degradation of unilamellar sphingomyelin/cholesterol liposomes: a kinetic study," Proc Natl Acad Sci U S A. 77(7):4030-4. (1980).
Illiades et al., "Triabodies: single chain Fv fragments without a linker form trivalent trimers," FEBS Lett. 409(3):437-41 (1997).
Jablonski et al., "Preparation of oligodeoxynucleotide-alkaline phosphatase conjugates and their use as hybridization probes," Nucleic Acids Res. 14(15):6115-28 (1986).
Jackson et al., "In vitro antibody maturation. Improvement of a high affinity, neutralizing antibody against IL-1 beta," J Immunol. 154(7):3310-9 (1995).
Jakobovits et al., "Analysis of homozygous mutant chimeric mice: deletion of the immunoglobulin heavy-chain joining region blocks B-cell development and antibody production," Proc Natl Acad Sci U S A. 90(6):2551-5 (1993).
Jakobovits et al., "Germ-line transmission and expression of a human-derived yeast artificial chromosome," Nature. 362(6417):255-8 (1993).
Jakobsdottir et al., "Susceptibility genes for age-related maculopathy on chromosome 10q26," Am J Hum Genet. 77(3):389-407 (2005).
Jefferis et al., "Glycosylation of antibody molecules: structural and functional significance," Chem Immunol. 65:111-28 (1997).
Johnson et al., "Human antibody engineering," Curr Opin Struct Biol. 3:564-71 (1993).
Jones et al., "Replacing the complementarity-determining regions in a human antibody with those from a mouse," Nature. 321(6069):522-5 (1986).
Justilien et al., "SOD2 knockdown mouse model of early AMD," Invest Ophthalmol Vis Sci. 48(10):4407-20 (2007).
Karan et al., "Lipofuscin accumulation, abnormal electrophysiology, and photoreceptor degeneration in mutant ELOVL4 transgenic mice: a model for macular degeneration," Proc Natl Acad Sci U S A. 102(11):4164-9 (2005).
Kinzler et al., "Identification of a gene located at chromosome 5q21 that is mutated in colorectal cancers," Science. 251(4999):1366-70 (1991).
Köhler et al., "Continuous cultures of fused cells secreting antibody of predefined specificity," Nature. 256(5517):495-7 (1975).
Kortt et al., "Single-chain Fv fragments of anti-neuraminidase antibody NC10 containing five- and ten-residue linkers form dimers and with zero-residue linker a trimer," Protein Eng. 10(4):423-33 (1997).
Kozbor et al., "A human hybrid myeloma for production of human monoclonal antibodies," J Immunol. 133(6):3001-5 (1984).
Landegren et al. "DNA diagnostics—molecular techniques and automation," Science. 242(4876):229-37 (1988).
Lee et al., "Conversion of Xenopus ectoderm into neurons by NeuroD, a basic helix-loop-helix protein," Science. 268(5212):836-44 (1995).
Levin, "The occurence of lung cancer in man," Acta Unio Int Contra Cancrum. 9(3):531-41 (1953).

(56) References Cited

OTHER PUBLICATIONS

Lewis et al., "Efficient delivery of siRNA for inhibition of gene expression in postnatal mice," Nat Genet. 32(1):107-8 (2002).
Limbach et al., "Summary: the modified nucleosides of RNA," Nucleic Acids Res. 22(12):2183-96 (1994).
Lipshutz et al., "Using oligonucleotide probe arrays to access genetic diversity," Biotechniques. 19(3):442-7 (1995).
Lobe et al., "Conditional genome alteration in mice," Bioessays. 20(3):200-8 (1998).
Lockhart et al., "Expression monitoring by hybridization to high-density oligonucleotide arrays," Nat Biotechnol. 14(13):1675-80 (1996).
Lonberg et al., "Antigen-specific human antibodies from mice comprising four distinct genetic modifications," Nature. 368(6474):856-9 (1994).
Lonberg et al., "Human antibodies from transgenic mice," Int Rev Immunol. 13(1):65-93 (1995).
Ma et al., "Deletion analysis of GAL4 defines two transcriptional activating segments," Cell. 48(5):847-53 (1987).
Ma et al., "The carboxy-terminal 30 amino acids of GAL4 are recognized by GAL80," Cell. 50(1):137-42 (1987).
Ma et al., "A new class of yeast transcriptional activators," Cell. 51(1):113-9 (1987).
Mage et al., Preparation of Fab and F(ab')2 Fragments from Monoclonal Antibodies. *Monoclonal Antibody Production Techniques and Applications*. Lawrence B. Schook, 79-97 (1987).
Marks et al., "By-passing immunization. Human antibodies from V-gene libraries displayed on phage," J Mol Biol. 222(3):581-97 (1991).
Marks et al., "By-passing immunization: building high affinity human antibodies by chain shuffling," Biotechnology (N Y). 10(7):779-83 (1992).
Martin et al., "Irreversible coupling of immunoglobulin fragments to preformed vesicles. An improved method for liposome targeting," J Biol Chem. 257(1):286-8 (1982).
Matteucci et al., "Synthesis of deoxyoligonucleotides on a polymer support," J Am Chem Soc. 103:3185-91 (1981).
Matthews et al., "Analytical strategies for the use of DNA probes," Anal Biochem. 169(1):1-25 (1988).
McCafferty et al., "Phage antibodies: filamentous phage displaying antibody variable domains," Nature. 348(6301):552-4 (1990).
McCaffrey et al., "RNA interference in adult mice," Nature. 418(6893):38-9 (2002).
Mendez et al., "Functional transplant of megabase human immunoglobulin loci recapitulates human antibody response in mice," Nat Genet. 15(2):146-56 (1997).
Mifflin, "Use and applications of nucleic acid probes in the clinical laboratory," Clin Chem. 35(9):1819-25 (1989).
Modrich, "Mechanisms and biological effects of mismatch repair," Annu Rev Genet. 25:229-53 (1991).
Mombaerts et al., "RAG-1-deficient mice have no mature B and T lymphocytes," Cell. 68(5):869-77 (1992).
Moran et al., "Radio frequency tag encoded combinatorial library method for the discovery of tripeptide-substituted cinnamic acid inhibitors of the protein tyrosine phosphatase PTP1B," J Am Chem Soc. 117(43):10787-8 (1995).
Morimoto et al., "Single-step purification of F(ab')2 fragments of mouse monoclonal antibodies (immunoglobulins G1) by hydrophobic interaction high performance liquid chromatography using TSKgel Phenyl-5PW," J Biochem Biophys Methods. 24(1-2):107-17 (1992).
Morrison, "Immunology. Success in specification," Nature. 368(6474):812-3 (1994).
Morrison et al., "Chimeric human antibody molecules: mouse antigen-binding domains with human constant region domains," Proc Natl Acad Sci U S A. 81(21):6851-5 (1984).
Munson et al., "Ligand: a versatile computerized approach for characterization of ligand-binding systems," Anal Biochem. 107(1):220-39 (1980).

Nambu et al., "Combretastatin A-4 phosphate suppresses development and induces regression of choroidal neovascularization," Invest Ophthalmol Vis Sci. 44(8):3650-5 (2003).
Neuberger, "Generating high-avidity human Mabs in mice," Nat Biotechnol. 14(7):826 (1996).
Newton et al., "Analysis of any point mutation in DNA. The amplification refractory mutation system (ARMS)," Nucleic Acids Res. 17(7):2503-16 (1989).
Nguyen et al., "A two-step hybridization method for chemiluminescent detection of single copy genes," Biotechniques. 13(1):116-23 (1992).
Nielsen et al., "Sequence-selective recognition of DNA by strand displacement with a thymine-substituted polyamide," Science. 254(5037):1497-500 (1991).
Novack et al., "Detection of single base-pair mismatches in DNA by chemical modification followed by electrophoresis in 15% polyacrylamide gel," Proc Natl Acad Sci U S A. 83(3):586-90 (1986).
Novotný et al., "Structural invariants of antigen binding: comparison of immunoglobulin VL-VH and VL-VL domain dimers," Proc Natl Acad Sci U S A. 82(14):4592-6 (1985).
Nygren et al., "Conjugation of horseradish peroxidase to Fab fragments with different homobifunctional and heterobifunctional cross-linking reagents. A comparative study," J Histochem Cytochem. 30(5):407-12 (1982).
Oka et al., "HtrA1 serine protease inhibits signaling mediated by Tgfbeta family proteins," Development. 131(5):1041-53 (2004).
Orita et al., "Detection of polymorphisms of human DNA by gel electrophoresis as single-strand conformation polymorphisms," Proc Natl Acad Sci U S A. 86(8):2766-70 (1989).
Osterrieder et al., "Lessons from gene knockouts," Rev Sci Tech. 17(1):351-64 (1998).
Pain et al., "Preparation of protein A-peroxidase monoconjugate using a heterobifunctional reagent, and its use in enzyme immunoassays," J Immunol Methods. 40(2):219-30 (1981).
Paul et al., "Effective expression of small interfering RNA in human cells," Nat Biotechnol. 20(5):505-8 (2002).
Perreault et al., "Mixed deoxyribo- and ribo-oligonucleotides with catalytic activity," Nature. 344(6266):565-7 (1990).
Peters et al., "Robot spotting," "Browser half-life," and "Products," Science. 277:398-401 (1997).
Philpott et al., "Lymphoid development in mice congenitally lacking T cell receptor alpha beta-expressing cells," Science. 256(5062):1448-52 (1992).
Pieken et al., "Kinetic characterization of ribonuclease-resistant 2'-modified hammerhead ribozymes," Science. 253(5017):314-7 (1991).
Riechmann et al., "Reshaping human antibodies for therapy," Nature. 332(6162):323-7 (1988).
Rigby et al., "Labeling deoxyribonucleic acid to high specific activity in vitro by nick translation with DNA polymerase I," J Mol Biol. 113(1):237-51 (1977).
Rosenfeld et al., "Ranibizumab: Phase III clinical trial results," Ophthalmol Clin North Am. 19(3):361-72 (2006).
Ruano et al., "Direct haplotyping of chromosomal segments from multiple heterozygotes via allele-specific PCR amplification," Nucleic Acids Res. 17(20):8392 (1989).
Saishin et al., "VEGF-TRAP(R1R2) suppresses choroidal neovascularization and VEGF-induced breakdown of the blood-retinal barrier," J Cell Physiol. 195(2):241-8 (2003).
Scaringe et al., "Chemical synthesis of biologically active oligoribonucleotides using beta-cyanoethyl protected ribonucleoside phosphoramidites," Nucleic Acids Res. 18(18):5433-41 (1990).
Schier et al., "Identification of functional and structural amino-acid residues by parsimonious mutagenesis," Gene. 169(2):147-55 (1996).
Sharrow et al., Overview of Flow Cytometry; Analysis of Flow Cytometry Data; Measurement of Intercellular Conjugates by Flow Cytometry. *Current Protocols in Immunology*. John Wiley & Sons, 5.1.1-5.1.8; 5.2.1-5.2.10; 5.6.1-5.6.8 (1991).
Shastry, "Genetic knockouts in mice: an update," Experientia. 51(11):1028-39 (1995).

(56) References Cited

OTHER PUBLICATIONS

Shastry, "Gene disruption in mice: models of development and disease," Mol Cell Biochem. 181(1-2):163-79 (1998).
Sheets et al., "Efficient construction of a large nonimmune phage antibody library: the production of high-affinity human single-chain antibodies to protein antigens," Proc Natl Acad Sci U S A. 95(11):6157-62 (1998).
Sheffield et al., "Attachment of a 40-base-pair G+C-rich sequence (GC-clamp) to genomic DNA fragments by the polymerase chain reaction results in improved detection of single-base changes," Proc Natl Acad Sci U S A. 86(1):232-6 (1989).
Sheffield et al., "Identification of novel rhodopsin mutations associated with retinitis pigmentosa by GC-clamped denaturing gradient gel electrophoresis," Am J Hum Genet. 49(4):699-706 (1991).
Shenk et al., "Biochemical method for mapping mutational alterations in DNA with S1 nuclease: the location of deletions and temperature-sensitive mutations in simian virus 40," Proc Natl Acad Sci U S A. 72(3):989-93 (1975).
Shi, "Mammalian RNAi for the masses," Trends Genet. 19(1):9-12 (2003).
Shinkai et al., "RAG-2-deficient mice lack mature lymphocytes owing to inability to initiate V(D)J rearrangement," Cell. 68(5):855-67 (1992).
Shoemaker et al., "Quantitative phenotypic analysis of yeast deletion mutants using a highly parallel molecular bar-coding strategy," Nat Genet. 14(4):450-6 (1996).
Sikela et al., "Screening an expression library with a ligand probe: isolation and sequence of a cDNA corresponding to a brain calmodulin-binding protein," Proc Natl Acad Sci U S A. 84(9):3038-42 (1987).
Smith et al., Cardiac Glycoside-Specific Antibodies in the Treatment of Digitalis Intoxication. *Antibodies in Human Diagnosis and Therapy.* Edgar Haber and Richard M. Krause, 365-389 (1977).
Smith et al., "Oxygen-induced retinopathy in the mouse," Invest Ophthalmol Vis Sci. 35(1):101-11 (1994).
Snouwaert et al., "An animal model for cystic fibrosis made by gene targeting," Science. 257(5073):1083-8 (1992).
Song et al., "RNA interference targeting Fas protects mice from fulminant hepatitis," Nat Med. 9(3):347-51 (2003).
Sui et al., "A DNA vector-based RNAi technology to suppress gene expression in mammalian cells," Proc Natl Acad Sci U S A. 99(8):5515-20 (2002).
Tanaka et al., "Choroidal neovascularization in transgenic mice expressing prokineticin 1: an animal model for age-related macular degeneration," Mol Ther. 13(3):609-16 (2006).
"The siRNA user guide," <https://web.archive.org/web/20020220171546/http://www.mpibpc.gwdg.de/abteilungen/100/105/sirna.html>, retrieved on Aug. 20, 2015 (5 pages).
Tsuchiya et al., "Expression of mouse HtrA1 serine protease in normal bone and cartilage and its upregulation in joint cartilage damaged by experimental arthritis," Bone. 37(3):323-36 (2005).
Umaña et al., "Engineered glycoforms of an antineuroblastoma IgG1 with optimized antibody-dependent cellular cytotoxic activity," Nat Biotechnol. 17(2):176-80 (1999).
Usman et al., "Automated chemical synthesis of long oligoribunucleotides using 2'-O-silylated ribonucleoside 3'-O-phosphoramidites on a controlled-pore glass support: synthesis of a 43-nucleotide sequence similar to the 3'-half molecule of an *Escherichia coli* formylmethionine tRNA," Am Chem Soc. 109(25):7845-54 (1987).
Usman, et al., "Exploiting the chemical synthesis of RNA," Trends Biochem Sci. 17(9):334-9 (1992).
Valancius et al., "Double-strand gap repair in a mammalian gene targeting reaction," Mol Cell Biol. 11(9):4389-97 (1991).
Vaughan et al., "Human antibodies with sub-nanomolar affinities isolated from a large non-immunized phage display library," Nat Biotechnol. 14(3):309-14 (1996).
Verhoeyen et al., "Reshaping human antibodies: grafting an antilysozyme activity," Science. 239(4847):1534-6 (1988).
Von Mehren et al., "Monoclonal antibody-based therapy," Curr Opin Oncol. 8(6):493-8 (1996).
Wartell et al., "Detecting base pair substitutions in DNA fragments by temperature-gradient gel electrophoresis," Nucleic Acids Res. 18(9):2699-705 (1990).
Waterhouse et al., "Combinatorial infection and in vivo recombination: a strategy for making large phage antibody repertoires," Nucleic Acids Res. 21(9):2265-6 (1993).
Wetmur et al., "Kinetics of renaturation of DNA," J Mol Biol. 31(3):349-70 (1968).
White et al., "Sets of linked genetic markers for human chromosomes," Annu Rev Genet. 22:259-79 (1988).
White et al., "Detecting single base substitutions as heteroduplex polymorphisms," Genomics. 12(2):301-6 (1992).
Wittwer et al., "Glycosylation at Asn-184 inhibits the conversion of single-chain to two-chain tissue-type plasminogen activator by plasmin," Biochemistry. 29(17):4175-80 (1990).
Wright et al., "Effect of glycosylation on antibody function: implications for genetic engineering," Trends Biotechnol. 15(1):26-32 (1997).
Wyss et al., "The structural role of sugars in glycoproteins," Curr Opin Biotechnol. 7(4):409-16 (1996).
Xia et al., "siRNA-mediated gene silencing in vitro and in vivo," Nat Biotechnol. 20(10):1006-10 (2002).
Yang et al., "A variant of the HTRA1 gene increases susceptibility to age-related macular degeneration," Science. 314(5801):992-3 (2006).
Yelton et al., "Affinity maturation of the BR96 anti-carcinoma antibody by codon-based mutagenesis," J Immunol. 155(4):1994-2004 (1995).
Yu et al., "RNA interference by expression of short-interfering RNAs and hairpin RNAs in mammalian cells," Proc Natl Acad Sci U S A. 99(9):6047-52 (2002).
Zamore et al., "siRNAs knock down hepatitis," Nat Med. 9(3):266-7 (2003).
Zola et al., Using monoclonal antibodies: Soluble antigens. *Monoclonal antibodies: A manual of techniques.* CRC Press, Inc., 147-158 (2000).
Zumbrunn et al., "Primary structure of a putative serine protease specific for IGF-binding proteins," FEBS Lett. 398(2-3):187-92 (1996).
Clausen et al., "HTRA proteases: regulated proteolysis in protein quality control," Nat Rev Mol Cell Biol. 12(3):152-62 (2011).
Extended European Search Report for European Patent Application No. 12840084.3, dated Jun. 3, 2015 (7 pages).
International Preliminary Report on Patentability for International Patent Application No. PCT/US2012/059878, dated Apr. 15, 2014 (6 pages).
International Search Report and Written Opinion for International Patent Application No. PCT/US2012/059878, dated Dec. 12, 2012 (9 pages).
Written Opinion for Singaporean Patent Application No. 11201401477X, dated Feb. 12, 2016 (8 pages).
"Roche initiates phase III trials for lampalizumab, first potential treatment for geographic atrophy (GA)," <http://www.roche.com/investors/updates/inv-update-2014-09-15.htm>, dated Sep. 15, 2014, retrieved on Feb. 1, 2017 (6 pages).
Ciferri et al., "The trimeric serine protease HtrA1 forms a cage-like inhibition complex with an anti-HtrA1 antibody," Biochem J. 472(2):169-81 (2015).
Eigenbrot et al., "Structural and functional analysis of HtrA1 and its subdomains," Structure. 20(6):1040-50 (2012).
Ganesan et al., "Structural and mechanistic insight into how antibodies inhibit serine proteases," Biochem J. 430(2):179-89 (2010).
Le et al., "Population Pharmacokinetics and Pharmacodynamics of Lampalizumab Administered Intravitreally to Patients With Geographic Atrophy," CPT Pharmacometrics Syst Pharmacol. 4(10):595-604 (2015).
Saldanha, Molecular Engineering I: Humanization. *Handbook of Therapeutic Antibodies.* Wiley-VCH, 119-144 (2007).
Invitation to Pay Additional Fees for International Patent Application No. PCT/US2016/059110, mailed Jan. 26, 2017 (9 pages).

(56) References Cited

OTHER PUBLICATIONS

International Search Report and Written Opinion for International Patent Application No. PCT/US2016/059110, mailed Mar. 31, 2017 (23 pages).

* cited by examiner

FIG. 1A

| Kabat# | 1 2 3 4 5 6 7 8 9 10 11 12 13 14 15 16 17 18 19 20 21 22 23 24 25 26 27 28 29 30 31 32 33 34 35 36 37 38 39 40 |
|---|---|
| hum III  | E V Q L V E S G G G L V Q P G G S L R L S C A A S G F T F S S Y A M S W V R Q A |
| YW505.94 | E V Q L V E S G G G L V Q P G G S L R L S C A A S G F X F S G Y XIX W V R Q A |

CDR regions marked: Chothia-CDR H1, Kabat-CDR H1, Contact-CDR H1

| Kabat# | 41 42 43 44 45 46 47 48 49 50 51 52 A 53 54 55 56 57 58 59 60 61 62 63 64 65 66 67 68 69 70 71 72 73 74 75 76 77 78 79 |
|---|---|
| hum III  | P G K G L E W V S V I S G D G G S T Y Y A D S V K G R F T I S A D T S K N T A Y |
| YW505.94 | P G K G L E W V G I D P G D G T G Y Y A D S V K G R F T I S A D T S K N T A Y |

CDR regions marked: Chothia-CDR H2, Kabat-CDR H2, Contact-CDR H2

| Kabat# | 80 81 82 A B C 83 84 85 86 87 88 89 90 91 92 93 94 95 96 97 98 99 100 A B C D E P G 101 102 103 104 105 106 107 |
|---|---|
| hum III  | L Q M N S L R A E D T A V Y Y C A R G             F D Y W G Q G T |
| YW505.94 | L Q M N S L R A E D T A V Y Y C A R G T F T S N G R I - - E D Y W G Q G T |

CDR regions marked: Kabat-CDR H3, Chothia-CDR H3, Contact-CDR H3

*FIG. 1B*

| HtrA1 Residue Number | YW505.94 Fab [EC50 (nM)] Mean ± SD | Relative to WT EC50 Fold Decrease |
|---|---|---|
| R190A | — | — |
| K191A | 14.0 ± 3.3 | 2.5 |
| V201A | 112.5 ± 16.4 | 20 |
| H220A | 32.0 ± 1.4 | 5.7 |
| T223A | 62.9 ± 2.2 | 11.2 |
| N224A | 134.6 ± 12.3 | 24 |
| K225A | 52.2 ± 1.3 | 9.3 |
| R227A | 25.9 ± 0.2 | 4.6 |
| E239A | 5.4 ± 0.2 | 0.9 |
| K241A | 23.0 ± 0.5 | 4.1 |
| K243A | 64.9 ± 4.2 | 11.6 |
| D244A | 4.7 ± 0.3 | 0.8 |
| E247A | 41.7 ± 0.9 | 7.4 |
| K248A | 195.8 ± 21.9 | 35 |
| D250A | 9.4 ± 3.5 | 1.7 |
| Y325A | 7.7 ± 0.6 | 1.4 |
| S328A | 2.3 ± 0.3 | 0.4 |
| L345A | — | — |
| WT | 5.6 ± 0.9 | 1 |

*FIG. 7A*

```
huHtrA1  ---MQIPRAALLPLILLLLAAPASAQLSRAGRSAPLAAGCPDRCEPARCPPQPEHCEGGR-  57
muHtrA1  ---MQSLRTTLLSLLLLLAAPSLALPSGTGRSAPAATVCPEHCDPTRCAPPPTDCEGGR-  57
muHtrA3  ---MQAR--ALLPATLAIATLAVLALARE-----PPAAPCPARCDVSRCPSP---RCPGGY-  49
muHtrA4  MSFQRLWAVRTQFLLLWLLLPAVPVPWAEARRSRVSLPCPDACDPTRCPTLPTCSAGLAP  60
          :*         *                           .  :    ::  *       .    * huHtrA1  ARDACGCCEVCGAPEGAACG-LQEGPCGEGLQCVVPFGVPASATVRRRAQAGLCVCAS--- 114
muHtrA1  VRDACGCCEVCGALEGAACG-LQEGPCGEGLQCVVPFGVPASATVRRRAQAGLCVCAS--- 114
muHtrA3  VPDLCNCCLVCAASEGEPCGGRPLDSPCGDSLECVR------------------------  91
muHtrA4  VPDRCGCCRVCAAAEGQECGGARGRPCAPRLRCGAPFSRDPSG------GAWLGTCGCAEGA 116
          * *  *  ** *:  *  *   *   :*                         *  * huHtrA1  -SEPVCGSDANTYANLCQLRAASRRSERLHRPPVIVLQRGACGQ-GQEDPNSLRHKYNFI 172
muHtrA1  -SEPVCGSDAKTYTNLCQLRAASRRSEKLRQPPVIVLQRGACGQ-GQEDPNSLRHKYNFI 172
muHtrA3  -THTVCGTDGHTYADVCALQAASRRALQVSGTPVRQLQKGACPS-GLHQLTSPRYKFNFI 149
muHtrA4  EDAVVCGSDGRTYPSLCALRKENRAARQRGALPAVPVQKGACEEAGTTRAGRLRKKYNFI 176
             . * :.....::* *:  :      :  :          *  :*.***   . *:*:*** huHtrA1  ADVVEKIAPAVVHIELFRKLPFSKREVPVASGSGFIVSEDGLIVTNAHVVTN------KH 226
muHtrA1  ADVVEKIAPAVVHIELYRKLPFSKREVPVASGSGFIVSEDGLIVTNAHVVTN------KN 226
muHtrA3  ADVVEKIAPAVVHIELFLRHPLFGRNVPLSSGSGFIMSEAGLIVTNAHVVSSSSTASGRQ 209
muHtrA4  AAVVEKVAPSVVHLQLFRRSPITNQEIPSSSGSGFIVSEDGLIVTNAHVLTN------QQ 230
          *.****:**.***::*:*:.*:      * :*:.****:**:*********::.          ::

huHtrA1  RVKVELKNGATYEAKIKDVDEKADIALIKIDHQGKLPVLLLGRSSELRPGEFVVAIGSPF 286
muHtrA1  RVKVELKNGATYEAKIKDVDEKADIALIKIDHQGKLPVLLLGRSSELRPGEFVVAIGSPF 286
muHtrA3  QLKVQLQNGDAVEATIQDIDIDKKSDIATTVIHPKKKLPVLLLGHSADLRPGEFVVAIGSPF 269
muHtrA4  KIQVELQSGARYEATVKDIDHKLDLALIKIEPDTELPVLLLGRSSDLRAGEFVVALGSPF 290
          ::::.:.:*:.*  * ****..:::..::*: *. .:::****.: *:.*****:****
```

FIG. 10A

```
huHtrA1   SLQNTVTTGIVSTTQRGGKELGLRNSDMDYIQTDAIINYGNSGGPLVNLDGEVIGINTLK  346
muHtrA1   SLQNTVTTGIVSTTQRGGKELGLRNSDMDYIQTDAIINYGNSGGPLVNLDGEVIGINTLK  346
muHtrA3   ALQNTVTTGIVSTAQRDGKELGLRDSDMDYIQTDAIINYGNSGGPLVNLDGEVIGINTLK  329
muHtrA4   SLQNTVTAGIVSTTQRGGRELGLKNSDIDYIQTDAIINHGNSGGPLVNLDGDVIGINTLK  350
          :*****.* .*:*:. *******:******.**** huHtrA1   VTAGISFAIPSDKIKKFLTESHDRQAKGKAITKKKYIGIRMMSLTSSKAKELKDRHRDFP  406
muHtrA1   VTAGISFAIPSDKIKKFLTESHDRQAKGKAITKKKYIGIRMMSLTSSKAKELKDRHRDFP  406
muHtrA3   VAAGISFAIPSDRITRFLSEFQNKHVKD---WKKRFIGIRMRTITPSLVEELKAANPDFP  386
muHtrA4   VTAGISFAIPSDRIRQFLEDYHERQLKGKAPLQKKYLGLRMLPLTLNLLQEMKRQDPEEP  410
          *:**********:* :**.: :.: *    :*:*::*:  .:*  . .: :. ..*: * huHtrA1   DVISGAYIIEVIPDTPAEAGGLKENDVIISINGQSVVSANDVSDVIKRESTLNMVVRRGN  466
muHtrA1   DVLSGAYIIEVIPDTPAEAGGLKENDVIISINGQSVVTANDVSDVIKKENTLNMVVRRGN  466
muHtrA3   AVSSGIYVQEVVPNSPSQRGGIQDGDIIVKVNGRPLADSSELQEAVLNESSLLEVRRGN  446
muHtrA4   DVSSGVFVYEVIQGSAAASSGLRDHDVIVSINGQPVTTTTDVIEAAVKDNDFLSIIVLRGS  470
          .* .* ::.**:  .. :..*:::.**:.:*: :  :: :   * :.: .* : : **.

huHtrA1   EDIMITVIPEEIDP  480
muHtrA1   EDIVITVIPEEIDP  480
muHtrA3   DDLLFSIIPEVVM-  459
muHtrA4   QTLFLTVTPEIIN-  483
          : :: :: **::

| Clone | CDR-L1 | | | | | | | CDR-L2 | | | | | | | CDR-L3 | | | | | | |
|---|---|---|---|---|---|---|---|---|---|---|---|---|---|---|---|---|---|---|---|---|---|
| | 28 | 29 | 30 | 31 | 32 | 33 | SEQ | 50 | 51 | 52 | 53 | 54 | 55 | SEQ | 91 | 92 | 93 | 94 | 95 | 96 | SEQ |
| YW505.94a (WT) | D | V | S | T | A | V | 54 | S | A | S | F | L | Y | 58 | S | Y | T | T | P | P | 59 |
| YW505.94a.1 | D | V | S | T | A | V | 54 | S | A | S | F | L | Y | 58 | S | Y | S | H | P | P | 60 |
| YW505.94a.7 | D | V | S | T | A | V | 54 | S | A | S | F | L | Y | 58 | S | Y | T | N | P | P | 61 |
| YW505.94a.22 | D | V | S | T | A | V | 54 | S | A | S | F | L | Y | 58 | S | Y | A | T | P | P | 62 |
| YW505.94a.26 | S | V | N | T | Y | L | 55 | S | A | S | F | L | Y | 58 | S | Y | D | T | P | P | 59 |
| YW505.94a.28 | D | H | S | T | A | V | 54 | S | A | S | F | L | Y | 58 | S | Y | S | S | P | A | 63 |
| YW505.94a.37 | D | V | S | T | A | V | 54 | S | A | S | F | L | Y | 58 | V | Y | T | T | P | P | 64 |
| YW505.94a.38 | D | V | S | T | A | V | 54 | S | A | S | F | L | Y | 58 | S | Y | A | T | P | P | 59 |
| YW505.94a.39 | D | V | S | T | A | V | 54 | S | A | S | F | L | Y | 58 | V | Y | N | S | P | S | 65 |
| YW505.94a.40 | D | V | S | T | A | V | 54 | S | A | S | F | L | Y | 58 | S | Y | S | T | P | A | 66 |
| YW505.94a.42 | D | V | S | T | A | V | 54 | S | A | S | F | L | Y | 58 | S | Y | T | T | P | A | 67 |
| YW505.94a.46 | D | V | S | T | A | V | 54 | S | A | S | F | L | Y | 58 | S | Y | S | T | P | P | 68 |
| YW505.94a.47 | D | V | S | T | N | L | 57 | S | A | S | F | L | Y | 58 | D | S | S | T | P | P | 59 |
| YW505.94a.50 | D | V | S | N | A | V | 54 | S | A | S | F | L | Y | 58 | S | Y | T | T | P | P | 69 |
| YW505.94a.51 | D | V | S | T | A | V | 54 | S | A | S | F | L | Y | 58 | D | S | A | A | P | P | 70 |
| YW505.94a.52 | D | V | S | T | Y | L | 56 | S | A | S | F | L | Y | 58 | D | D | D | L | P | A | 71 |
| YW505.94a.54 | P | V | S | T | A | V | 54 | S | A | S | F | L | Y | 58 | S | Y | T | A | P | P | 72 |
| YW505.94a.77 | D | V | S | T | A | V | 54 | S | A | S | F | L | Y | 58 | S | Y | S | L | P | P | 59 |
| YW505.94a.78 | D | V | S | T | A | V | 54 | S | A | S | F | L | Y | 58 | S | Y | A | A | P | P | 73 |
| YW505.94a.82 | D | V | G | T | A | V | 54 | S | A | S | F | L | Y | 58 | S | Y | S | T | P | P | 59 |
| YW505.94a.89 | D | V | S | T | A | V | 54 | S | A | S | F | L | Y | 58 | S | Y | T | R | P | P | 74 |

| Clone | CDR-H1 | | | | | | | | | CDR-H2 | | | | | | | | | | | CDR-H3 | | | | | | | | | | |
|---|---|---|---|---|---|---|---|---|---|---|---|---|---|---|---|---|---|---|---|---|---|---|---|---|---|---|---|---|---|---|---|---|
| | 26 | 27 | 28 | 29 | 30 | 31 | 32 | 33 | SEQ | 50 | 51 | 52 | A | 53 | 54 | 55 | 56 | 57 | 58 | SEQ | 95 | 96 | 97 | 98 | 99 | 100 | A | B | C | D | SEQ |
| YW505.94a (WT) | G | F | S | T | S | G | Y | Y | 75 | W | I | T | P | A | Y | G | D | T | N | 81 | G | T | F | T | L | S | W | G | H | Y | 83 |
| YW505.94a.1 | G | F | S | T | S | G | Y | Y | 75 | W | I | T | P | A | Y | G | D | T | N | 81 | G | T | F | T | L | S | W | G | H | Y | 83 |
| YW505.94a.7 | G | F | S | T | S | D | Y | Y | 76 | W | I | T | P | A | Y | G | D | T | N | 81 | G | T | F | T | L | S | W | G | H | Y | 83 |
| YW505.94a.22 | G | F | S | T | S | G | Y | Y | 75 | W | I | T | P | A | Y | G | D | T | N | 81 | G | T | F | T | L | S | W | G | H | Y | 83 |
| YW505.94a.26 | G | F | S | T | D | G | Y | Y | 77 | W | I | T | P | A | Y | G | D | T | N | 81 | G | T | F | T | L | S | W | G | H | Y | 83 |
| YW505.94a.28 | G | F | S | T | S | D | Y | Y | 76 | W | I | T | P | A | Y | G | D | T | N | 81 | G | T | F | T | L | S | W | G | H | Y | 83 |
| YW505.94a.37 | G | F | S | T | Y | G | Y | Y | 78 | W | I | T | P | A | Y | G | D | T | N | 81 | G | T | F | T | L | S | W | G | H | Y | 83 |
| YW505.94a.38 | G | F | S | T | S | G | Y | Y | 75 | W | I | T | P | A | Y | G | D | T | N | 81 | G | T | F | T | L | S | W | G | H | Y | 83 |
| YW505.94a.39 | G | F | S | T | S | G | Y | Y | 75 | W | I | T | P | A | Y | G | D | T | N | 81 | G | T | F | T | L | S | W | G | H | Y | 83 |
| YW505.94a.40 | G | F | S | T | S | G | Y | Y | 75 | W | I | T | P | A | Y | G | D | T | D | 82 | G | T | F | T | L | S | W | G | H | Y | 83 |
| YW505.94a.42 | G | F | S | T | S | G | Y | Y | 75 | W | I | T | P | A | Y | G | D | T | N | 81 | G | T | F | T | L | S | W | G | H | Y | 84 |
| YW505.94a.46 | G | F | S | T | S | G | Y | Y | 75 | W | I | T | P | A | Y | G | D | T | D | 82 | G | T | F | T | L | S | W | G | H | Y | 83 |
| YW505.94a.47 | G | F | S | T | S | D | Y | Y | 76 | W | I | T | P | A | Y | G | D | T | D | 82 | G | T | F | T | L | S | W | G | H | Y | 83 |
| YW505.94a.50 | G | F | S | T | S | G | Y | Y | 75 | W | I | T | P | A | Y | G | D | T | N | 81 | G | T | F | T | L | S | W | G | H | Y | 83 |
| YW505.94a.51 | G | F | T | T | S | G | Y | Y | 75 | W | I | T | P | A | Y | G | D | T | N | 81 | G | T | F | T | L | S | W | G | H | Y | 83 |
| YW505.94a.52 | G | F | S | T | S | G | Y | Y | 75 | W | I | T | P | A | Y | G | D | T | N | 81 | G | T | F | T | L | S | W | G | H | Y | 83 |
| YW505.94a.54 | G | F | S | T | S | G | Y | Y | 75 | W | I | T | P | A | Y | G | D | T | N | 81 | G | T | F | T | L | S | W | G | H | Y | 83 |
| YW505.94a.77 | G | F | S | T | A | G | Y | Y | 79 | W | I | T | P | A | Y | G | D | T | N | 81 | G | T | F | T | L | S | W | G | H | Y | 83 |
| YW505.94a.78 | C | F | S | T | S | G | Y | Y | 80 | W | I | T | P | A | Y | G | D | T | N | 81 | G | T | F | T | L | S | W | G | H | Y | 83 |
| YW505.94a.82 | G | F | S | T | S | G | Y | Y | 75 | W | I | T | P | A | Y | G | D | T | N | 81 | G | T | F | T | L | S | W | G | H | Y | 83 |
| YW505.94a.89 | G | F | S | T | S | G | Y | Y | 75 | W | I | T | P | A | Y | G | D | T | D | 82 | G | T | F | T | L | S | W | G | H | Y | 83 |

FIG. 16

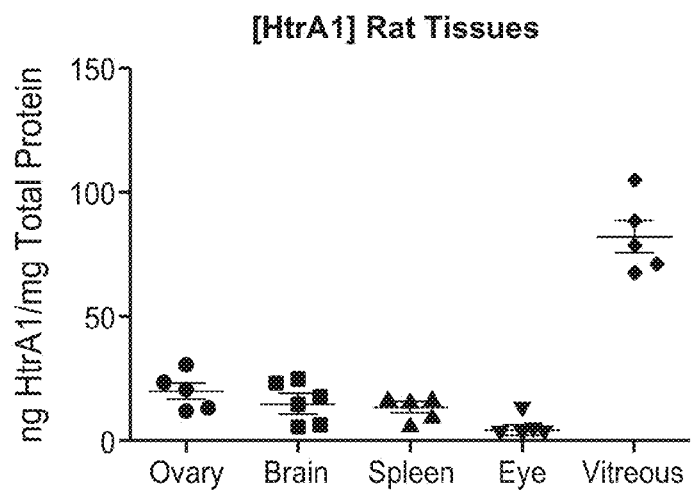
FIG. 19A
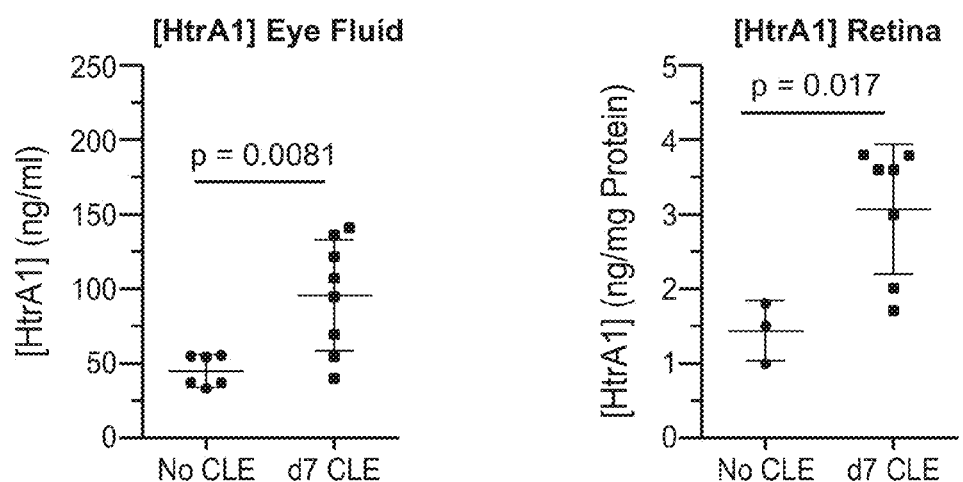
FIG. 19B
FIG. 19C

ANTI-HTRA1 ANTIBODIES AND METHODS OF USE

CROSS REFERENCE TO RELATED APPLICATIONS

This application claims the benefit of U.S. Provisional Application Ser. No. 61/547,649, filed Oct. 14, 2011, which application is hereby incorporated by reference in its entirety.

SEQUENCE LISTING

The instant application contains a Sequence Listing submitted in ASCII format via EFS-Web and hereby incorporated by reference in its entirety. Said ASCII copy, created on Oct. 4, 2012, is named P4761RUS.txt and is 47,451 bytes in size.

FIELD OF THE INVENTION

The present invention relates to anti-HtrA1 antibodies and methods of using the same.

BACKGROUND

The serine protease HtrA1 (PRSS11; Clan PA, family S1) belongs to an evolutionarily conserved family of HtrA proteins (Clausen, T., et al., *Nat Rev Mol Cell Biol* 12:152-62 (2011); Clausen, T., et al., *Mol Cell* 10:443-55 (2002)). In humans, HtrA1, 3, and 4 share the same domain architecture: an N-terminal IGFBP-like module and a Kazal-like module, a protease domain with trypsin-like fold, and a C-terminal PDZ domain. The physiological relevance of HtrA1 has been firmly established by the identification of human loss-of-function mutations causing familial ischemic cerebral small-vessel disease (Hara, K., et al., *N Engl J Med* 360:1729-39 (2009)). The molecular mechanism involves deficient TGF-β inhibition by HtrA1 resulting in increased TGF-β signaling (Hara et al., 2009). Dysregulated TGF-β signaling by aberrant HtrA1 expression may also contribute to arthritic disease (Oka, C., et al., *Development* 131:1041-53 (2004); Tsuchiya, A., et al., *Bone* 37:323-36 (2005)), perhaps in conjunction with HtrA1-mediated degradation of various extracellular matrix components (Chamberland et al., *J Biol Chem* 284:27352-9 (2009); Grau, S., et al., *J Biol Chem* 281:6124-9 (2006); Hadfield, K. D., et al., *J Biol Chem* 283:5928-38 (2008); Tocharus, J., et al., *Dev Growth Differ* 46:257-74 (2004); Tsuchiya et al., 2005)), or indirectly via up-regulation of matrix metalloproteases (Grau et al., 2006). In addition, human genetic studies identified a strong correlation between progression of age-related macular degeneration and a SNP in the HtrA1 promoter region, which results in increased HtrA1 transcript levels (Dewan, A., et al., *Science* 314:989-92 (2006); Yang, Z., et al., *Science* 314:992-3 (2006)). Therefore, inhibition of HtrA1 enzymatic function is an attractive therapeutic approach, e.g. in age-related macular degeneration and in arthritic disease.

SUMMARY

The invention provides anti-HtrA1 antibodies and methods of using the same for diagnostic and therapeutic purposes.

In one aspect, the invention provides an isolated antibody that binds to HtrA1 competitively with antibody comprising a VH sequence of SEQ ID NO:8 and a VL sequence of SEQ ID NO:7. Competitive binding may be determined, for example, using an ELISA assay.

In one aspect, the invention provides an isolated antibody that bind to HtrA1 having one or more of the following properties: (i) an $IC_{50}$ of less than 50 nM, 30 nM, 25 nM, 20 nM, 15 nM, 10 nM, 5 nM, 3 nM, 2.5 nM, 2 nM, 1 nM, or less for one or more HtrA1 substrates; (ii) binds to HtrA1 with a ratio of 1 variable domain to one subunit of an HtrA1 trimer (e.g., a Fab binds to an HtrA1 trimer with a ratio of 3 Fab to 1 HtrA1 trimer, and an IgG binds to an HtrA1 trimer with a ratio of 3 IgG to 2 HtrA1 trimers), (iii) for antibodies comprising two variable domains, binds to HtrA1 in a manner that results in the forming a "cage" similar to that shown in FIG. 9, (iv) does not prevent trimer formation of HtrA1, (v) binds to one or more residues in Loop C of the HtrA1 protein, (vi) binds to the protease domain of HtrA1, (vii) binds to an epitope comprising one or both of amino acids N224 or K248 of SEQ ID NO:13, or amino acids equivalent thereto in a different HtrA1 sequence (e.g., amino acids N224 and K248 of SEQ ID NO:14, see FIGS. 10A and B); (viii) binds to an epitope comprising one or more of the following residues of N224, K248, V201, T223, K243, K225, E247 and H220 of SEQ ID NO:13, or amino acids equivalent thereto in a different HtrA1 sequence; (ix) cross-reacts with murine HtrA1; (x) does not cross-react with HtrA2, HtrA3 and/or HtrA4; (xi) binds to HtrA1 competitively with an antibody comprising a VH sequence of SEQ ID NO:8 and a VL sequence of SEQ ID NO:7, (xii) binds to HtrA1 with a dissociation constant of ≤500 nM, or (xiii) inhibits complex formation between HtrA1 and α1-antitrypsin (A1AT).

In another aspect, the invention provides an isolated antibody that binds to HtrA1, wherein the antibody (i) binds to an epitope that includes N224, K248, or both of HtrA1, and (ii) inhibits HtrA1 with an $IC_{50}$ of ≤30 nM. In certain embodiments, the epitope further includes one or more of the following residues of HtrA1: V201, T223, K243, K225, E247 and H220. In certain embodiments, the antibody may further comprise one or more of the following properties: (i) binds to HtrA1 with a ratio of 1 variable domain to one subunit of an HtrA1 trimer, or (ii) does not prevent trimer formation of HtrA1. In certain embodiments, the $IC_{50}$ is determined using a serine protease assay with a substrate having SEQ ID NO:12, e.g., such as the FRET assay described herein.

In certain embodiments, an antibody described herein does not cross-react with one or more of HtrA2, HtrA3 and HtrA4.

In certain embodiments, an antibody described herein has a dissociation constant of ≤500 nM. The dissociation constant may be determined, for example, by BIAcore using a Fab.

In certain embodiments, an antibody described herein is a monoclonal antibody.

In certain embodiments, an antibody described herein is a human, humanized, or chimeric antibody.

In certain embodiments, an antibody described herein is an antibody fragment that binds HtrA1.

In certain embodiments, an antibody described herein comprises (a) HVR-H3 comprising the amino acid sequence GTFLTX$_p$WGHYFDY, wherein X$_p$ is S or T (SEQ ID NO: 27); (b) HVR-L3 comprising the amino acid sequence QQX$_g$X$_h$X$_i$X$_j$PX$_k$T, wherein X$_g$ is S, V or D; X$_h$ is Y, D or S; X$_i$ is T, S, A, D or N; X$_j$ is T, H, N, S, A, L or R; and X$_k$ is P, T, A or S (SEQ ID NO: 24); and (c) HVR-H2 comprising the amino acid sequence WIDPYGGDTX$_o$Y-ADSVKG, wherein X$_o$ is N or D (SEQ ID NO: 26).

In certain embodiments, an antibody described herein comprises (a) HVR-H3 comprising the amino acid sequence of SEQ ID NO:6; (b) HVR-L3 comprising the amino acid sequence of SEQ ID NO:3; and (c) HVR-H2 comprising the amino acid sequence of SEQ ID NO:5.

In certain embodiments, an antibody described herein comprises (a) HVR-H3 comprising the amino acid sequence of SEQ ID NO:6; (b) HVR-L3 comprising the amino acid sequence of SEQ ID NO:19; and (c) HVR-H2 comprising the amino acid sequence of SEQ ID NO:5.

In certain embodiments, an antibody described herein comprises (a) HVR-H3 comprising the amino acid sequence of SEQ ID NO:6; (b) HVR-L3 comprising the amino acid sequence of SEQ ID NO:22; and (c) HVR-H2 comprising the amino acid sequence of SEQ ID NO:5.

In certain embodiments, an antibody described herein comprises (a) HVR-H1 comprising the amino acid sequence GFX$_l$IX$_m$X$_n$YYIH, wherein X$_l$ is N, S or T; X$_m$ is S, D, Y or A; and X$_n$ is G or D (SEQ ID NO: 25); (b) HVR-H2 comprising the amino acid sequence WIDPYGGDTX$_o$Y-ADSVKG, wherein X$_o$ is N or D (SEQ ID NO:26); and (c) HVR-H3 comprising the amino acid sequence GTFLTX$_p$-WGHYFDY, wherein X$_p$ is S or T (SEQ ID NO: 27).

In certain embodiments, an antibody described herein further comprises (a) HVR-L1 comprising the amino acid sequence RASQX$_a$X$_b$X$_c$X$_d$X$_e$X$_f$A, wherein X$_a$ is D, S or V; X$_b$ is V or I; X$_c$ is S, N or G; X$_d$ is T or N; X$_e$ is A or Y; and X$_f$ is V or L (SEQ ID NO: 23); (b) HVR-L2 comprising the amino acid sequence of SEQ ID NO:2; and (c) HVR-L3 comprising the amino acid sequence QQX$_g$X$_h$X$_i$X$_j$PX$_k$T, wherein X$_g$ is S, V or D; X$_h$ is Y, D or S; X$_i$ is T, S, A, D or N; X$_j$ is T, H, N, S, A, L or R; and X$_k$ is P, T, A or S (SEQ ID NO: 24).

In certain embodiments, an antibody described herein comprises (a) HVR-H1 comprising the amino acid sequence of SEQ ID NO:4; (b) HVR-H2 comprising the amino acid sequence of SEQ ID NO:5; and (c) HVR-H3 comprising the amino acid sequence of SEQ ID NO:6.

In certain embodiments, an antibody described herein further comprises (a) HVR-L1 comprising the amino acid sequence of SEQ ID NO:1; (b) HVR-L2 comprising the amino acid sequence of SEQ ID NO:2; and (c) HVR-L3 comprising the amino acid sequence of SEQ ID NO:3.

In certain embodiments, an antibody described herein comprises (a) HVR-H1 comprising the amino acid sequence of SEQ ID NO:20; (b) HVR-H2 comprising the amino acid sequence of SEQ ID NO:5; and (c) HVR-H3 comprising the amino acid sequence of SEQ ID NO:6.

In certain embodiments, an antibody described herein further comprises (a) HVR-L1 comprising the amino acid sequence of SEQ ID NO:18; (b) HVR-L2 comprising the amino acid sequence of SEQ ID NO:2; and (c) HVR-L3 comprising the amino acid sequence of SEQ ID NO:19.

In certain embodiments, an antibody described herein further comprises (a) HVR-L1 comprising the amino acid sequence of SEQ ID NO:21; (b) HVR-L2 comprising the amino acid sequence of SEQ ID NO:2; and (c) HVR-L3 comprising the amino acid sequence of SEQ ID NO:22.

In certain embodiments, an antibody described herein comprises (a) HVR-L1 comprising the amino acid sequence of SEQ ID NO:1; (b) HVR-L2 comprising the amino acid sequence of SEQ ID NO:2; and (c) HVR-L3 comprising the amino acid sequence of SEQ ID NO:3.

In certain embodiments, an antibody described herein comprises (a) HVR-L1 comprising the amino acid sequence of SEQ ID NO:18; (b) HVR-L2 comprising the amino acid sequence of SEQ ID NO:2; and (c) HVR-L3 comprising the amino acid sequence of SEQ ID NO:19.

In certain embodiments, an antibody described herein comprises (a) HVR-L1 comprising the amino acid sequence of SEQ ID NO:21; (b) HVR-L2 comprising the amino acid sequence of SEQ ID NO:2; and (c) HVR-L3 comprising the amino acid sequence of SEQ ID NO:22.

In certain embodiments, an antibody described herein further comprises a heavy chain variable domain framework (FR2) sequence of SEQ ID NO:17.

In certain embodiments, an antibody described herein comprises (a) a VH sequence having at least 95% sequence identity to the amino acid sequence of SEQ ID NO:8; (b) a VL sequence having at least 95% sequence identity to the amino acid sequence of SEQ ID NO:7; or (c) a VH sequence as in (a) and a VL sequence as in (b).

In certain embodiments, an antibody described herein comprises (a) a VH sequence having at least 95% sequence identity to the amino acid sequence of SEQ ID NO:29; (b) a VL sequence having at least 95% sequence identity to the amino acid sequence of SEQ ID NO:7; or (c) a VH sequence as in (a) and a VL sequence as in (b).

In certain embodiments, an antibody described herein comprises (a) a VH sequence having at least 95% sequence identity to the amino acid sequence of SEQ ID NO:29; (b) a VL sequence having at least 95% sequence identity to the amino acid sequence of SEQ ID NO:28; or (c) a VH sequence as in (a) and a VL sequence as in (b).

In certain embodiments, an antibody described herein comprises (a) a VH sequence having at least 95% sequence identity to the amino acid sequence of SEQ ID NO:29; (b) a VL sequence having at least 95% sequence identity to the amino acid sequence of SEQ ID NO:30; or (c) a VH sequence as in (a) and a VL sequence as in (b).

In certain embodiments, an antibody described herein comprises (a) a VH sequence comprising SEQ ID NO: 32; (b) a VL sequence comprising SEQ ID NO: 31; or (c) a VH sequence comprising SEQ ID NO: 32 and a VL sequence comprising SEQ ID NO: 31.

In certain embodiments, an antibody described herein comprises a VH sequence of SEQ ID NO:8.

In certain embodiments, an antibody described herein comprises a VL sequence of SEQ ID NO:7.

In certain embodiments, an antibody described herein comprises a VH sequence of SEQ ID NO:30.

In certain embodiments, an antibody described herein comprises a VL sequence of SEQ ID NO:28.

In certain embodiments, an antibody described herein comprises a VL sequence of SEQ ID NO:29.

In certain embodiments, an antibody described herein comprises a VH sequence of SEQ ID NO:8 and a VL sequence of SEQ ID NO:7.

In certain embodiments, an antibody described herein comprises a VH sequence of SEQ ID NO:30 and a VL sequence of SEQ ID NO:28.

In certain embodiments, an antibody described herein comprises a VH sequence of SEQ ID NO:30 and a VL sequence of SEQ ID NO:29.

In certain embodiments, an antibody described herein comprises (a) HVR-H1 comprising the amino acid sequence GFX$_l$IX$_m$X$_n$YYIH, wherein X$_l$ is N, S or T; X$_m$ is S, D, Y or A; and X$_n$ is G or D (SEQ ID NO: 25); (b) HVR-H2 comprising the amino acid sequence WIDPYGGDTX$_o$Y-ADSVKG, wherein X$_o$ is N or D (SEQ ID NO:26); (c) HVR-H3 comprising the amino acid sequence GTFLTX$_p$-WGHYFDY, wherein X$_p$ is S or T (SEQ ID NO: 27); (d) HVR-L1 comprising the amino acid sequence RASQX$_a$ $X_bX_cX_dX_eX_fA$, wherein $X_a$ is D, S or V; $X_b$ is V or I; $X_c$ is S, N or G; $X_d$ is T or N; $X_e$ is A or Y; and $X_f$ is V or L (SEQ ID NO: 23); (e) HVR-L2 comprising the amino acid sequence of SEQ ID NO:2; and (f) HVR-L3 comprising the amino acid sequence $QQX_gX_hX_iX_jPX_kT$, wherein $X_g$ is S, V or D; $X_h$ is Y, D or S; $X_i$ is T, S, A, D or N; $X_j$ is T, H, N, S, A, L or R; and $X_k$ is P, T, A or S (SEQ ID NO: 24).

In certain embodiments, an antibody described herein comprises (a) HVR-H1 comprising an amino acid sequence selected from: SEQ ID NO:4, 20, and 47-51; (b) HVR-H2 comprising an amino acid sequence selected from: SEQ ID NO:5 and 52; (c) HVR-H3 comprising an amino acid sequence selected from: SEQ ID NO:6 and 53; (d) HVR-L1 comprising an amino acid sequence selected from: SEQ ID NO:1, 18, 21 and 33; (e) HVR-L2 comprising the amino acid sequence of SEQ ID NO:2; and (f) HVR-L3 comprising an amino acid sequence selected from: SEQ ID NO:3, 19, 22, and 34-46.

In certain embodiments, an antibody described herein comprises (a) HVR-H1 comprising the amino acid sequence of SEQ ID NO:4; (b) HVR-H2 comprising the amino acid sequence of SEQ ID NO:5; (c) HVR-H3 comprising the amino acid sequence of SEQ ID NO:6; (d) HVR-L1 comprising the amino acid sequence of SEQ ID NO:1; (e) HVR-L2 comprising the amino acid sequence of SEQ ID NO:2; and (f) HVR-L3 comprising the amino acid sequence of SEQ ID NO:3.

In certain embodiments, an antibody described herein comprises (a) HVR-H1 comprising the amino acid sequence of SEQ ID NO:20; (b) HVR-H2 comprising the amino acid sequence of SEQ ID NO:5; (c) HVR-H3 comprising the amino acid sequence of SEQ ID NO:6; (d) HVR-L1 comprising the amino acid sequence of SEQ ID NO:18; (e) HVR-L2 comprising the amino acid sequence of SEQ ID NO:2; and (f) HVR-L3 comprising the amino acid sequence of SEQ ID NO:19.

In certain embodiments, an antibody described herein comprises (a) HVR-H1 comprising the amino acid sequence of SEQ ID NO:20; (b) HVR-H2 comprising the amino acid sequence of SEQ ID NO:5; (c) HVR-H3 comprising the amino acid sequence of SEQ ID NO:6; (d) HVR-L1 comprising the amino acid sequence of SEQ ID NO:21; (e) HVR-L2 comprising the amino acid sequence of SEQ ID NO:2; and (f) HVR-L3 comprising the amino acid sequence of SEQ ID NO:22.

In certain embodiments, an antibody described herein comprises (a) HVR-H3 comprising the amino acid sequence $GTFLTX_pWGHY$, wherein $X_p$ is S or T (SEQ ID NO: 89); (b) HVR-L3 comprising the amino acid sequence $X_gX_hX_iX_jPX_k$, wherein $X_g$ is S, V or D; $X_h$ is Y, D or S; $X_i$ is T, S, A, D or N; $X_j$ is T, H, N, S, A, L or R; and $X_k$ is P, T, A or S (SEQ ID NO: 86); and (c) HVR-H2 comprising the amino acid sequence $WIDPYGGDTX_o$, wherein $X_o$ is N or D (SEQ ID NO:88).

In certain embodiments, an antibody described herein comprises (a) HVR-H1 comprising the amino acid sequence $GFX_lIX_mX_nYY$, wherein $X_l$ is N, S or T; $X_m$ is S, D, Y or A; and $X_n$ is G or D (SEQ ID NO:87); (b) HVR-H2 comprising the amino acid sequence $WIDPYGGDTX_o$, wherein $X_o$ is N or D (SEQ ID NO:88); and (c) HVR-H3 comprising the amino acid sequence $GTFLTX_pWGHY$, wherein $X_p$ is S or T (SEQ ID NO: 89).

In certain embodiments, an antibody described herein further comprises (a) HVR-L1 comprising the amino acid sequence $X_aX_bX_cX_dX_eX_f$, wherein $X_a$ is D, S or V; $X_b$ is V or I; $X_c$ is S, N or G; $X_d$ is T or N; $X_e$ is A or Y; and $X_f$ is V or L (SEQ ID NO: 85); (b) HVR-L2 comprising the amino acid sequence of SEQ ID NO:58; and (c) HVR-L3 comprising the amino acid sequence $X_gX_hX_iX_jPX_k$, wherein $X_g$ is S, V or D; $X_h$ is Y, D or S; $X_i$ is T, S, A, D or N; $X_j$ is T, H, N, S, A, L or R; and $X_k$ is P, T, A or S (SEQ ID NO: 86).

In certain embodiments, an antibody described herein comprises (a) HVR-H1 comprising the amino acid sequence $GFX_lIX_mX_nYY$, wherein $X_l$ is N, S or T; $X_m$ is S, D, Y or A; and $X_n$ is G or D (SEQ ID NO:87); (b) HVR-H2 comprising the amino acid sequence $WIDPYGGDTX_o$, wherein $X_o$ is N or D (SEQ ID NO:88); (c) HVR-H3 comprising the amino acid sequence $GTFLTX_pWGHY$, wherein $X_p$ is S or T (SEQ ID NO: 89); (d) HVR-L1 comprising the amino acid sequence $X_aX_bX_cX_dX_eX_f$, wherein $X_a$ is D, S or V; $X_b$ is V or I; $X_c$ is S, N or G; $X_d$ is T or N; $X_e$ is A or Y; and $X_f$ is V or L (SEQ ID NO: 85); (e) HVR-L2 comprising the amino acid sequence of SEQ ID NO:58; and (f) HVR-L3 comprising the amino acid sequence $X_gX_hX_iX_jPX_k$, wherein $X_g$ is S, V or D; $X_h$ is Y, D or S; $X_i$ is T, S, A, D or N; $X_j$ is T, H, N, S, A, L or R; and $X_k$ is P, T, A or S (SEQ ID NO:86).

In certain embodiments, an antibody described herein comprises (a) HVR-H1 comprising an amino acid sequence selected from: SEQ ID NO:4, 20, 47-51, and 75-80; (b) HVR-H2 comprising an amino acid sequence selected from: SEQ ID NO:5, 52, and 81-82; (c) HVR-H3 comprising an amino acid sequence selected from: SEQ ID NO:6, 53 and 83-84; (d) HVR-L1 comprising an amino acid sequence selected from: SEQ ID NO:1, 18, 21, 33, and 54-57; (e) HVR-L2 comprising an amino acid sequence selected from: SEQ ID NO:2 and 58; and (f) HVR-L3 comprising an amino acid sequence selected from: SEQ ID NO:3, 19, 22, 34-46, and 59-74.

In certain embodiments, an antibody described herein is a full length IgG1 or IgG4 antibody.

In another aspect, an isolated nucleic acid encoding an anti-HtrA1 antibody described herein is provided.

In another aspect, a host cell comprising an isolated nucleic acid encoding an anti-HtrA1 antibody described herein is provided.

In another aspect, a method of producing an antibody is provided. The method may comprise culturing a host cell comprising an isolated nucleic acid encoding an anti-HtrA1 antibody under conditions suitable for expression of the nucleic acid encoding the anti-HtrA1 antibody. The method may further comprise recovering the anti-HtrA1 antibody from the host cell culture, purifying the anti-HtrA1 antibody, or formulating the anti-HtrA1 antibody with a pharmaceutically acceptable excipient.

In another aspect, an immunoconjugate comprising an anti-HtrA1 antibody and a cytotoxic agent is provided.

In another aspect, a pharmaceutical formulation comprising an anti-HtrA1 antibody and a pharmaceutically acceptable carrier is provided.

In another aspect, the application provides an anti-HtrA1 antibody for use as a medicament, e.g., for use in treating age-related macular degeneration (wet or dry), geographic atrophy, diabetic retinopathy, retinopathy of prematurity, or polypoidal choroidal vasculopathy, for inhibiting degeneration of retinal or photoreceptor cells, or for inhibiting HtrA1 protease activity in an eye.

In another aspect, the application provides use of an anti-HtrA1 antibody for the manufacture of a medicament, e.g., a medicament for the treatment of age-related macular degeneration (AMD, wet or dry), geographic atrophy (GA), diabetic retinopathy (DR), retinopathy of prematurity (ROP), or polypoidal choroidal vasculopathy (PCV), for inhibiting degeneration of retinal or photoreceptor cells, or for inhibiting HtrA1 protease activity in an eye.

In another aspect, the application provides a method of treating an individual having age-related macular degeneration (wet or dry), geographic atrophy, diabetic retinopathy, retinopathy of prematurity, or polypoidal choroidal vasculopathy, comprising administering to the individual an effective amount of an anti-HtrA1 antibody as described herein.

In another aspect, the application provides a method for inhibiting retinal or photoreceptor cell degeneration in an individual comprising administering to the individual an effective amount of an anti-HtrA1 antibody as described herein to inhibit retinal or photoreceptor cell degeneration.

In another aspect, the application provides a method of inhibiting HtrA1 serine protease activity in an eye of an individual comprising administering to the individual an effective amount of an anti-HtrA1 antibody as described herein to inhibit HtrA1 serine protease activity in the eye.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 1A-B. FIG. 1A shows the light chain variable domain sequence of anti-HtrA1 antibody94 (YW505.94) (SEQ ID NO:7). FIG. 1B shows the heavy chain variable domain sequence of anti-HtrA1 antibody94 (YW505.94) (SEQ ID NO:8). The residues are numbered according to the Kabat numbering system (Kabat, E. A., et al., 1991, In: Sequences of proteins of immunological interest, fifth edition. National Institutes of Health, Bethesda, Md.). The YW505.94 light chain variable domain sequence is aligned with human Kappa1 light chain consensus sequence (SEQ ID NO: 9) and the YW505.94 heavy chain variable domain sequence is aligned with the human subgroup III heavy chain sequence (SEQ ID NO: 10). The boxed sequences are CDRs according to Kabat definitions. The sequence differences between anti-HtrA1 (YW505.94) and consensus sequences are shaded.

FIGS. 7A-C. Mapping the functional epitope of IgG94 on HuHtrA1_PD. FIG. 7A shows the results of an ELISA measuring the binding of IgG94 to HuHtrA1_PD mutants with alanine substitutions of residues surrounding the active site. The shaded rows indicate alanine substitutions that resulted in a greater than 5-fold decrease in binding. FIG. 7B shows the structure of HuHtrA1_PD (PDB 3NWU) (Clausen, T., et al., Nat Rev Mol Cell Biol. 12:152-62 (2011)) with Mutated residues indicated. Medium gray shading shows mutations without loss of IgG94 binding in initial experiments; dark gray shading shows a subset of residues with >5-fold loss in binding affinity. The three monomers forming the protease domain trimer, shown in surface representation, are shaded light gray. Catalytic triad residues D250 and S328 are underlined. FIG. 7C shows a close-up view of the loops harboring the epitope residues N224 and K248 on monomer (light gray, as cartoon) of HuHtrA1_PD (PDB 3NWU). Also included is the catalytic residue H220.

FIGS. 10A-B. Alignment of human HtrA1 (SEQ ID NO:13), murine HtrA1 (SEQ ID NO:14), murine HtrA3 (SEQ ID NO:15), and murine HtrA4 (SEQ ID NO:16).

FIG. 15. Light chain HVR sequences for affinity-improved variants of anti-HtrA1 antibody YW505.94a.

FIG. 16. Heavy chain HVR sequences for affinity-improved variants of anti-HtrA1 antibody YW505.94a.

FIGS. 19A-C. Results of ELISA assay showing levels of HtrA1 protein in rat tissues (FIG. 19A), mouse eye fluid (FIG. 19B) and mouse retina tissue (FIG. 19C).

DETAILED DESCRIPTION OF EMBODIMENTS OF THE INVENTION

I. Definitions

Figure 2:
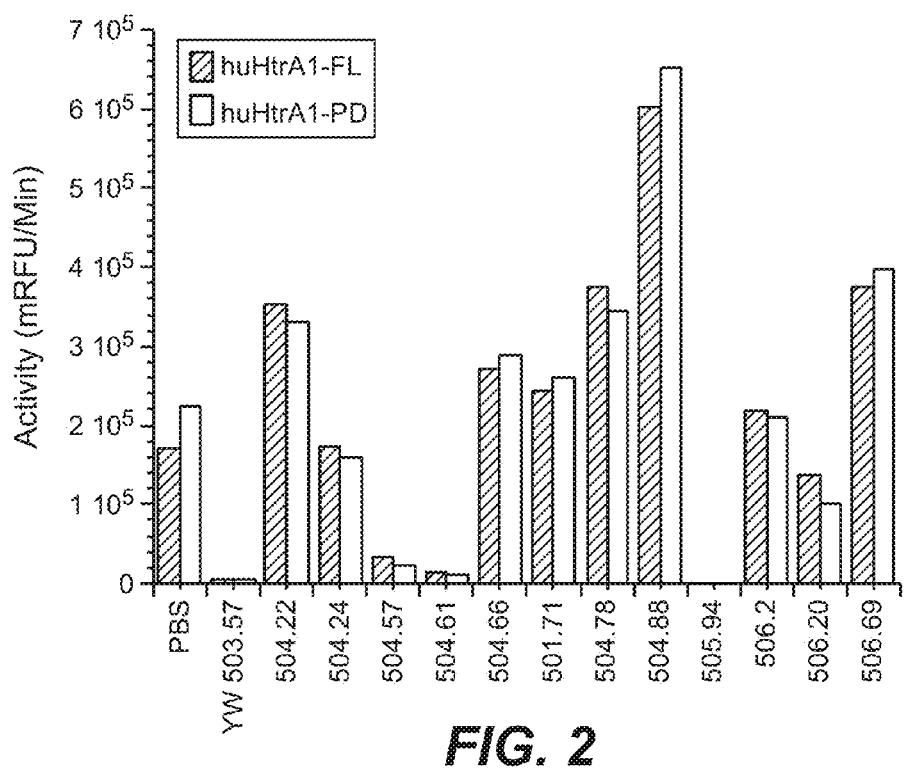
FIG. 2. Screening of panel of 13 phage derived antibodies (IgG). Single concentrations (0.08-0.28 mg/ml final) of IgG were incubated with HuHtrA1 or HuHtrA1_PD and enzyme activity measured in the FRET assay. Of the 13 antibodies tested, antibodies YW503.57, YW504.57, YW504.61 and YW505.94 (also referred to as Ab94 or IgG94) strongly inhibited both HuHtrA1 and HuHtrA1_PD activities.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-HtrA1 antibody" and "an antibody that binds to HtrA1" refer to an antibody that is capable of binding HtrA1 with sufficient affinity such that the antibody is useful as a diagnostic and/or therapeutic agent in targeting HtrA1. In one embodiment, the extent of binding of an anti-HtrA1 antibody to an unrelated, non-HtrA1 protein is less than about 10% of the binding of the antibody to HtrA1 as measured, e.g., by a radioimmunoassay (RIA). In certain embodiments, an antibody that binds to HtrA1 has a dissociation constant (Kd) of $\leq 1$ μM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g., from $10^{-9}$ M to $10^{-13}$ M). In certain embodiments, an anti-HtrA1 antibody binds to an epitope of HtrA1 that is conserved among HtrA1 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, Md., 1991.

"Framework region" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1 (L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH(H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. An HVR region as used herein comprise any number of residues located within positions 24-36 (for L1), 46-56 (for L2), 89-97 (for L3), 26-35B (for H1), 47-65 (for H2), and 93-102 (for H3). Therefore, an HVR includes residues in positions described previously:

A) 24-34 (L1), 50-52 (L2), 91-96 (L3), 26-32 (H1), 53-55 (H2), and 96-101 (H3) (Chothia and Lesk, *J. Mol. Biol.* 196:901-917 (1987);

B) 24-34 of L1, 50-56 of L2, 89-97 of L3, 31-35B of H1, 50-65 of H2, and 95-102 of H3 (Kabat et al., *Sequences of Proteins of Immunological Interest*, 5th Ed. Public Health Service, National Institutes of Health, Bethesda, Md. (1991).

C) 30-36 (L1), 46-55 (L2), 89-96 (L3), 30-35 (H1), 47-58 (H2), 93-100a-j (H3) (MacCallum et al. *J. Mol. Biol.* 262: 732-745 (1996).

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally, at a chromosomal location that is different from its natural chromosomal location, or contains only coding sequences.

"Isolated nucleic acid encoding an anti-HtrA1 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "High-temperature requirement associated A" or "HtrA1," as used herein, refers to any native HtrA1 from any vertebrate source, including mammals such as primates (e.g. humans) and rodents (e.g., mice and rats), unless otherwise indicated. The term encompasses "full-length," unprocessed HtrA1 as well as any form of HtrA1 that results from processing in the cell. The term also encompasses naturally occurring variants of HtrA1, e.g., splice variants or allelic variants. The amino acid sequence of an exemplary HtrA1 is shown in SEQ ID NO:13. Exemplary fragments of human HtrA1 include fragments comprising, consisting essentially of, or consistingof amino acids Q23-P480 or P161-K379.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on the discovery that a reduction of HtrA1 activity has protective effects on photoreceptor cells in the eye, the outer nuclear layer, and on elecroretinogram functionality. In certain embodiments, antibodies that bind to HtrA1 are provided. Antibodies of the invention are useful, e.g., for the diagnosis or treatment of various diseases associated with HtrA1 activity, including ocular disorders such as age-related macular degeneration or geographic atrophy.

A. Exemplary Anti-HtrA1 Antibodies

Figure 9:
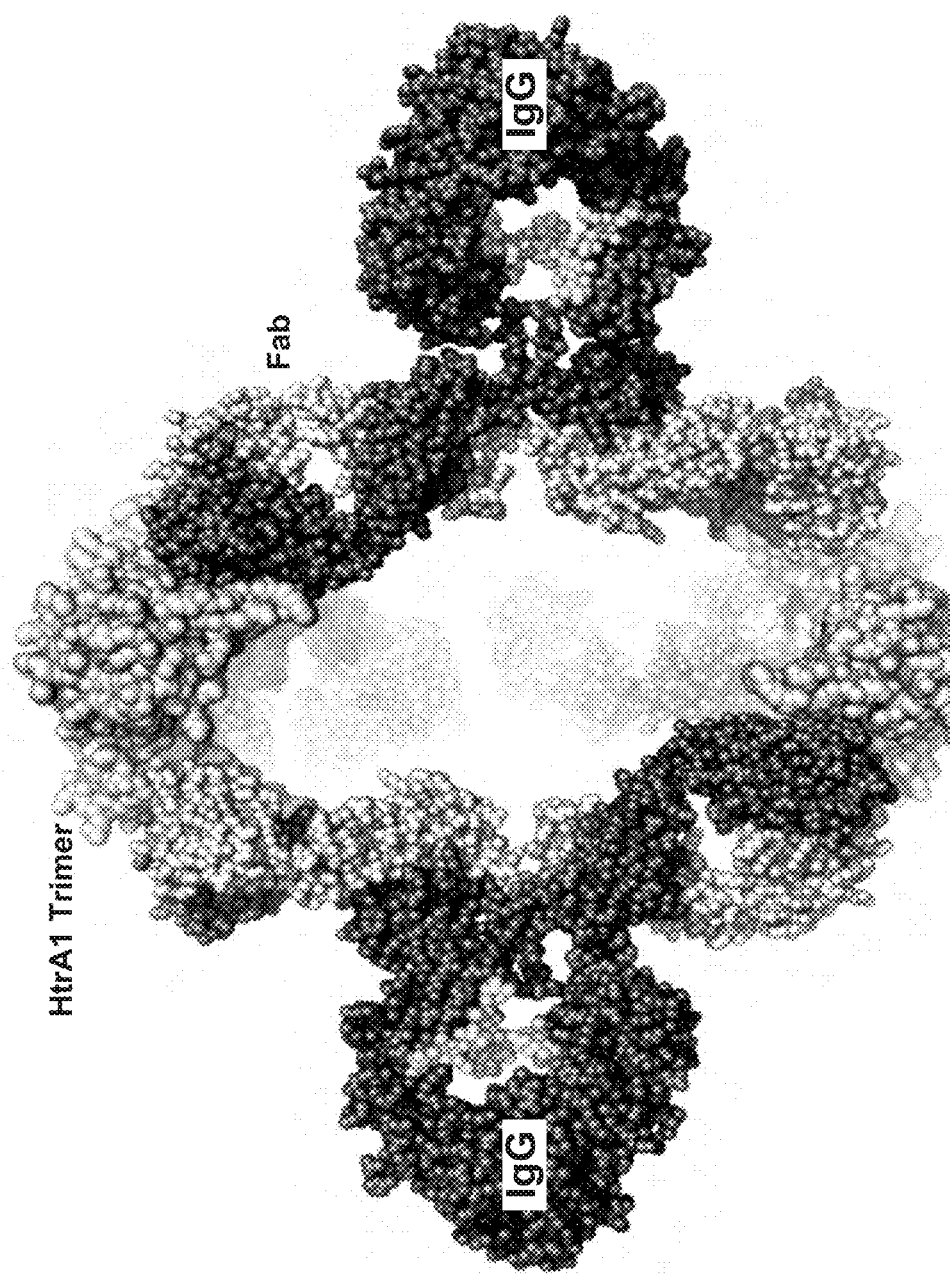
FIG. 9. Hypothetical 'cage model' of the IgG:HuHtrA1-PD complex.

In one aspect, the invention provides isolated antibodies that bind to HtrA1. In certain embodiments, an anti-HtrA1 antibody has one or more of the following properties: (i) has an IC$_{50}$ of less than 50 nM, 30 nM, 25 nM, 20 nM, 15 nM, 10 nM, 5 nM, 3 nM, 2.5 nM, 2 nM, 1 nM, or less for one or more HtrA1 substrates; (ii) binds to HtrA1 with a ratio of 1 variable domain to one subunit of an HtrA1 trimer (e.g., a Fab binds to an HtrA1 trimer with a ratio of 3 Fab to 1 HtrA1 trimer, and an IgG binds to an HtrA1 trimer with a ratio of 3 IgG to 2 HtrA1 trimers), (iii) for antibodies comprising two variable domains, binds to HtrA1 in a manner that results in the forming a "cage" similar to that shown in FIG. 9, (iv) does not prevent trimer formation of HtrA1, (v) binds to one or more residues in Loop C of the HtrA1 protein, (vi) binds to the protease domain of HtrA1, (vii) binds to an epitope comprising one or both of amino acids N224 or K248 of SEQ ID NO:13, or amino acids equivalent thereto in a different HtrA1 sequence (e.g., amino acids N224 and K248 of SEQ ID NO:14, see FIGS. 10A-B); (viii) binds to an epitope comprising one or more of residues N224, K248, V201, T223, K243, K225, E247 and H220 of SEQ ID NO:13, or amino acids equivalent thereto in a different HtrA1 sequence; (ix) cross-reacts with murine HtrA1; (x) does not cross-react with HtrA2, HtrA3 and/or HtrA4; (xi) binds to HtrA1 competitively with an antibody comprising a VH sequence of SEQ ID NO:8 and a VL sequence of SEQ ID NO:7, or (xii) binds to HtrA1 with a dissociation constant of ≤500 nM, or (xiii) inhibits complex formation between HtrA1 and α1-antitrypsin (A1AT).

In one aspect, the invention provides an anti-HtrA1 antibody comprising at least one, two, three, four, five, or six HVRs selected from (a) HVR-H1 comprising the amino acid sequence of SEQ ID NO:87; (b) HVR-H2 comprising the amino acid sequence of SEQ ID NO:88; (c) HVR-H3 comprising the amino acid sequence of SEQ ID NO:89; (d) HVR-L1 comprising the amino acid sequence of SEQ ID NO:85; (e) HVR-L2 comprising the amino acid sequence of SEQ ID NO:58; and (f) HVR-L3 comprising the amino acid sequence of SEQ ID NO:86. In one embodiment, the invention provides an anti-HtrA1 antibody comprising at least one, two, three, four, five, or six HVRs selected from (a) HVR-H1 comprising the amino acid sequence of SEQ ID NO:25; (b) HVR-H2 comprising the amino acid sequence of SEQ ID NO:26; (c) HVR-H3 comprising the amino acid sequence of SEQ ID NO:27; (d) HVR-L1 comprising the amino acid sequence of SEQ ID NO:23; (e) HVR-L2 comprising the amino acid sequence of SEQ ID NO:2; and (f) HVR-L3 comprising the amino acid sequence of SEQ ID NO:24. In one embodiment, the invention provides an anti-HtrA1 antibody comprising at least one, two, three, four, five, or six HVRs selected from (a) HVR-H1 comprising an amino acid sequence selected from: SEQ ID NO:4, 20, 47-51 and 75-80; (b) HVR-H2 comprising an amino acid sequence selected from: SEQ ID NO:5, 52 and 81-82; (c) HVR-H3 comprising an amino acid sequence selected from: SEQ ID NO:6, 53 and 83-84; (d) HVR-L1 comprising an amino acid sequence selected from: SEQ ID NO:1, 18, 21, 33 and 54-57; (e) HVR-L2 comprising an amino acid sequence selected from: SEQ ID NO:2 and 58; and (f) HVR-L3 comprising an amino acid sequence selected from: SEQ ID NO:3, 19, 22, 34-46 and 59-74. In one embodiment, the invention provides an anti-HtrA1 antibody comprising at least one, two, three, four, five, or six HVRs selected from (a) HVR-H1 comprising the amino acid sequence of SEQ ID NO:4; (b) HVR-H2 comprising the amino acid sequence of SEQ ID NO:5; (c) HVR-H3 comprising the amino acid sequence of SEQ ID NO:6; (d) HVR-L1 comprising the amino acid sequence of SEQ ID NO:1; (e) HVR-L2 comprising the amino acid sequence of SEQ ID NO:2; and (f) HVR-L3 comprising the amino acid sequence of SEQ ID NO:3. In one embodiment, the invention provides an anti-HtrA1 antibody comprising at least one, two, three, four, five, or six HVRs selected from (a) HVR-H1 comprising the amino acid sequence of SEQ ID NO:20; (b) HVR-H2 comprising the amino acid sequence of SEQ ID NO:5; (c) HVR-H3 comprising the amino acid sequence of SEQ ID NO:6; (d) HVR-L1 comprising the amino acid sequence of SEQ ID NO:18; (e) HVR-L2 comprising the amino acid sequence of SEQ ID NO:2; and (f) HVR-L3 comprising the amino acid sequence of SEQ ID NO:19. In one embodiment, the invention provides an anti-HtrA1 antibody comprising at least one, two, three, four, five, or six HVRs selected from (a) HVR-H1 comprising the amino acid sequence of SEQ ID NO:20; (b) HVR-H2 comprising the amino acid sequence of SEQ ID NO:5; (c) HVR-H3 comprising the amino acid sequence of SEQ ID NO:6; (d) HVR-L1 comprising the amino acid sequence of SEQ ID NO:21; (e) HVR-L2 comprising the amino acid sequence of SEQ ID NO:2; and (f) HVR-L3 comprising the amino acid sequence of SEQ ID NO:22.

In one aspect, the invention provides an antibody comprising at least one, at least two, or all three VH HVR sequences selected from (a) HVR-H1 comprising the amino acid sequence of SEQ ID NO:87; (b) HVR-H2 comprising the amino acid sequence of SEQ ID NO:88; and (c) HVR-H3 comprising the amino acid sequence of SEQ ID NO:89. In one embodiment, the antibody comprises HVR-H3 comprising the amino acid sequence of SEQ ID NO:89. In another embodiment, the antibody comprises HVR-H3 comprising the amino acid sequence of SEQ ID NO:89 and HVR-L3 comprising the amino acid sequence of SEQ ID NO:86. In a further embodiment, the antibody comprises HVR-H3 comprising the amino acid sequence of SEQ ID NO:89, HVR-L3 comprising the amino acid sequence of SEQ ID NO:86, and HVR-H2 comprising the amino acid sequence of SEQ ID NO:88. In a further embodiment, the antibody comprises (a) HVR-H1 comprising the amino acid sequence of SEQ ID NO:87; (b) HVR-H2 comprising the amino acid sequence of SEQ ID NO:88; and (c) HVR-H3 comprising the amino acid sequence of SEQ ID NO:89.

In one aspect, the invention provides an antibody comprising at least one, at least two, or all three VH HVR sequences selected from (a) HVR-H1 comprising the amino acid sequence of SEQ ID NO:25; (b) HVR-H2 comprising the amino acid sequence of SEQ ID NO:26; and (c) HVR-H3 comprising the amino acid sequence of SEQ ID NO:27. In one embodiment, the antibody comprises HVR-H3 comprising the amino acid sequence of SEQ ID NO:27. In another embodiment, the antibody comprises HVR-H3 comprising the amino acid sequence of SEQ ID NO:27 and HVR-L3 comprising the amino acid sequence of SEQ ID NO:24. In a further embodiment, the antibody comprises HVR-H3 comprising the amino acid sequence of SEQ ID NO:27, HVR-L3 comprising the amino acid sequence of SEQ ID NO:24, and HVR-H2 comprising the amino acid sequence of SEQ ID NO:26. In a further embodiment, the antibody comprises (a) HVR-H1 comprising the amino acid sequence of SEQ ID NO:25; (b) HVR-H2 comprising the amino acid sequence of SEQ ID NO:26; and (c) HVR-H3 comprising the amino acid sequence of SEQ ID NO:27.

In one embodiment, the invention provides an antibody comprising at least one, at least two, or all three VH HVR sequences selected from (a) HVR-H1 comprising an amino acid sequence selected from: SEQ ID NO:4, 20, 47-51 and 75-80; (b) HVR-H2 comprising an amino acid sequence selected from SEQ ID NO:5, 52 and 81-82; and (c) HVR-H3 comprising an amino acid sequence selected from: SEQ ID NO:6, 53 and 83-84. In one embodiment, the antibody comprises HVR-H3 comprising an amino acid sequence selected from SEQ ID NO:6 and 53. In another embodiment, the antibody comprises HVR-H3 comprising an amino acid sequence selected from SEQ ID NO:6, 53 and 83-84 and HVR-L3 comprising an amino acid sequence selected from SEQ ID NO:3, 19, 22, 34-46 and 59-74. In a further embodiment, the antibody comprises HVR-H3 comprising an amino acid sequence selected from SEQ ID NO:6, 53 and 83-84, HVR-L3 comprising an amino acid sequence selected from SEQ ID NO: 3, 19, 22, 34-46 and 59-74, and HVR-H2 comprising an amino acid sequence selected from SEQ ID NO:5, 52 and 81-82. In a further embodiment, the antibody comprises (a) HVR-H1 comprising an amino acid sequence selected from SEQ ID NO:4, 20, 47-51 and 75-80; (b) HVR-H2 comprising an amino acid sequence selected from SEQ ID NO:5, 52 and 81-82; and (c) HVR-H3 comprising an amino acid sequence selected from SEQ ID NO:6, 53 and 83-84.

In one embodiment, the invention provides an antibody comprising at least one, at least two, or all three VH HVR sequences selected from (a) HVR-H1 comprising the amino acid sequence of SEQ ID NO:4; (b) HVR-H2 comprising the amino acid sequence of SEQ ID NO:5; and (c) HVR-H3 comprising the amino acid sequence of SEQ ID NO:6. In one embodiment, the antibody comprises HVR-H3 comprising the amino acid sequence of SEQ ID NO:6. In another embodiment, the antibody comprises HVR-H3 comprising the amino acid sequence of SEQ ID NO:6 and HVR-L3 comprising the amino acid sequence of SEQ ID NO:3. In a further embodiment, the antibody comprises HVR-H3 comprising the amino acid sequence of SEQ ID NO:6, HVR-L3 comprising the amino acid sequence of SEQ ID NO:3, and HVR-H2 comprising the amino acid sequence of SEQ ID NO:5. In a further embodiment, the antibody comprises (a) HVR-H1 comprising the amino acid sequence of SEQ ID NO:4; (b) HVR-H2 comprising the amino acid sequence of SEQ ID NO:5; and (c) HVR-H3 comprising the amino acid sequence of SEQ ID NO:6.

In one embodiment, the invention provides an antibody comprising at least one, at least two, or all three VH HVR sequences selected from (a) HVR-H1 comprising the amino acid sequence of SEQ ID NO:20; (b) HVR-H2 comprising the amino acid sequence of SEQ ID NO:5; and (c) HVR-H3 comprising the amino acid sequence of SEQ ID NO:6. In one embodiment, the antibody comprises HVR-H3 comprising the amino acid sequence of SEQ ID NO:20. In another embodiment, the antibody comprises HVR-H3 comprising the amino acid sequence of SEQ ID NO:20 and HVR-L3 comprising the amino acid sequence of SEQ ID NO:19. In a further embodiment, the antibody comprises HVR-H3 comprising the amino acid sequence of SEQ ID NO:20, HVR-L3 comprising the amino acid sequence of SEQ ID NO:19, and HVR-H2 comprising the amino acid sequence of SEQ ID NO:5. In another embodiment, the antibody comprises HVR-H3 comprising the amino acid sequence of SEQ ID NO:20 and HVR-L3 comprising the amino acid sequence of SEQ ID NO:22. In a further embodiment, the antibody comprises HVR-H3 comprising the amino acid sequence of SEQ ID NO:20, HVR-L3 comprising the amino acid sequence of SEQ ID NO:22, and HVR-H2 comprising the amino acid sequence of SEQ ID NO:5. In a further embodiment, the antibody comprises (a) HVR-H1 comprising the amino acid sequence of SEQ ID NO:20; (b) HVR-H2 comprising the amino acid sequence of SEQ ID NO:5; and (c) HVR-H3 comprising the amino acid sequence of SEQ ID NO:6.

In another aspect, the invention provides an antibody comprising at least one, at least two, or all three VL HVR sequences selected from (a) HVR-L1 comprising the amino acid sequence of SEQ ID NO:85; (b) HVR-L2 comprising the amino acid sequence of SEQ ID NO:58; and (c) HVR-L3 comprising the amino acid sequence of SEQ ID NO:86. In one embodiment, the invention provides an antibody comprising at least one, at least two, or all three VL HVR sequences selected from (a) HVR-L1 comprising the amino acid sequence of SEQ ID NO:23; (b) HVR-L2 comprising the amino acid sequence of SEQ ID NO:2; and (c) HVR-L3 comprising the amino acid sequence of SEQ ID NO:24. In one embodiment, the antibody comprises (a) HVR-L1 comprising the amino acid sequence of SEQ ID NO:85; (b) HVR-L2 comprising the amino acid sequence of SEQ ID NO:58; and (c) HVR-L3 comprising the amino acid sequence of SEQ ID NO:86. In one embodiment, the antibody comprises (a) HVR-L1 comprising the amino acid sequence of SEQ ID NO:23; (b) HVR-L2 comprising the amino acid sequence of SEQ ID NO:2; and (c) HVR-L3 comprising the amino acid sequence of SEQ ID NO:24.

In another embodiment, the invention provides an antibody comprising at least one, at least two, or all three VL HVR sequences selected from (a) HVR-L1 comprising an amino acid sequence selected from SEQ ID NO:1, 18, 21, 33 and 54-57; (b) HVR-L2 comprising an amino acid sequence selected from SEQ ID NO:2 and 58; and (c) HVR-L3 comprising an amino acid sequence selected from SEQ ID NO:3, 19, 22, 34-46 and 59-74. In one embodiment, the antibody comprises (a) HVR-L1 comprising an amino acid sequence selected from SEQ ID NO:1, 18, 21, 33 and 54-57; (b) HVR-L2 comprising an amino acid sequence selected from SEQ ID NO:2 and 58; and (c) HVR-L3 comprising an amino acid sequence selected from SEQ ID NO:3, 19, 22, 34-46 and 59-74.

In another embodiment, the invention provides an antibody comprising at least one, at least two, or all three VL HVR sequences selected from (a) HVR-L1 comprising the amino acid sequence of SEQ ID NO:1; (b) HVR-L2 comprising the amino acid sequence of SEQ ID NO:2; and (c) HVR-L3 comprising the amino acid sequence of SEQ ID NO:3. In one embodiment, the antibody comprises (a) HVR-L1 comprising the amino acid sequence of SEQ ID NO:1; (b) HVR-L2 comprising the amino acid sequence of SEQ ID NO:2; and (c) HVR-L3 comprising the amino acid sequence of SEQ ID NO:3.

In another embodiment, the invention provides an antibody comprising at least one, at least two, or all three VL HVR sequences selected from (a) HVR-L1 comprising the amino acid sequence of SEQ ID NO:18; (b) HVR-L2 comprising the amino acid sequence of SEQ ID NO:2; and (c) HVR-L3 comprising the amino acid sequence of SEQ ID NO:19. In one embodiment, the antibody comprises (a) HVR-L1 comprising the amino acid sequence of SEQ ID NO:18; (b) HVR-L2 comprising the amino acid sequence of SEQ ID NO:2; and (c) HVR-L3 comprising the amino acid sequence of SEQ ID NO:19.

In another embodiment, the invention provides an antibody comprising at least one, at least two, or all three VL HVR sequences selected from (a) HVR-L1 comprising the amino acid sequence of SEQ ID NO:21; (b) HVR-L2 comprising the amino acid sequence of SEQ ID NO:2; and (c) HVR-L3 comprising the amino acid sequence of SEQ ID NO:22. In one embodiment, the antibody comprises (a) HVR-L1 comprising the amino acid sequence of SEQ ID NO:21; (b) HVR-L2 comprising the amino acid sequence of SEQ ID NO:2; and (c) HVR-L3 comprising the amino acid sequence of SEQ ID NO:22.

In another aspect, an antibody of the invention comprises (a) a VH domain comprising at least one, at least two, or all three VH HVR sequences selected from (i) HVR-H1 comprising the amino acid sequence of SEQ ID NO:87, (ii) HVR-H2 comprising the amino acid sequence of SEQ ID NO:88, and (iii) HVR-H3 comprising the amino acid sequence of SEQ ID NO:89; and (b) a VL domain comprising at least one, at least two, or all three VL HVR sequences selected from (i) HVR-L1 comprising the amino acid sequence of SEQ ID NO:85, (ii) HVR-L2 comprising the amino acid sequence of SEQ ID NO:58, and (c) HVR-L3 comprising the amino acid sequence of SEQ ID NO:86. In one embodiment, an antibody of the invention comprises (a) a VH domain comprising at least one, at least two, or all three VH HVR sequences selected from (i) HVR-H1 comprising the amino acid sequence of SEQ ID NO:25, (ii) HVR-H2 comprising the amino acid sequence of SEQ ID NO:26, and (iii) HVR-H3 comprising the amino acid sequence of SEQ ID NO:27; and (b) a VL domain comprising at least one, at least two, or all three VL HVR sequences selected from (i) HVR-L1 comprising the amino acid sequence of SEQ ID NO:23, (ii) HVR-L2 comprising the amino acid sequence of SEQ ID NO:2, and (c) HVR-L3 comprising the amino acid sequence of SEQ ID NO:24.

In another embodiment, an antibody of the invention comprises (a) a VH domain comprising at least one, at least two, or all three VH HVR sequences selected from (i) HVR-H1 comprising an amino acid sequence selected from SEQ ID NO:4, 20, 47-51 and 75-80, (ii) HVR-H2 comprising an amino acid sequence selected from SEQ ID NO:5, 52 and 81-82, and (iii) HVR-H3 comprising an amino acid sequence selected from SEQ ID NO:6, 53 and 83-84; and (b) a VL domain comprising at least one, at least two, or all three VL HVR sequences selected from (i) HVR-L1 comprising an amino acid sequence selected from SEQ ID NO:1, 18, 21, 33 and 54-57, (ii) HVR-L2 comprising an amino acid sequence selected from SEQ ID NO:2 and 58, and (c) HVR-L3 comprising an amino acid sequence selected from SEQ ID NO:3, 19, 22, 34-46 and 59-74.

In another embodiment, an antibody of the invention comprises (a) a VH domain comprising at least one, at least two, or all three VH HVR sequences selected from (i) HVR-H1 comprising the amino acid sequence of SEQ ID NO:4, (ii) HVR-H2 comprising the amino acid sequence of SEQ ID NO:5, and (iii) HVR-H3 comprising the amino acid sequence of SEQ ID NO:6; and (b) a VL domain comprising at least one, at least two, or all three VL HVR sequences selected from (i) HVR-L1 comprising the amino acid sequence of SEQ ID NO:1, (ii) HVR-L2 comprising the amino acid sequence of SEQ ID NO:2, and (c) HVR-L3 comprising the amino acid sequence of SEQ ID NO:3.

In another embodiment, an antibody of the invention comprises (a) a VH domain comprising at least one, at least two, or all three VH HVR sequences selected from (i) HVR-H1 comprising the amino acid sequence of SEQ ID NO:20, (ii) HVR-H2 comprising the amino acid sequence of SEQ ID NO:5, and (iii) HVR-H3 comprising the amino acid sequence of SEQ ID NO:6; and (b) a VL domain comprising at least one, at least two, or all three VL HVR sequences selected from (i) HVR-L1 comprising the amino acid sequence of SEQ ID NO:18, (ii) HVR-L2 comprising the amino acid sequence of SEQ ID NO:2, and (c) HVR-L3 comprising the amino acid sequence of SEQ ID NO:19.

In another aspect, an antibody of the invention comprises (a) a VH domain comprising at least one, at least two, or all three VH HVR sequences selected from (i) HVR-H1 comprising the amino acid sequence of SEQ ID NO:20, (ii) HVR-H2 comprising the amino acid sequence of SEQ ID NO:5, and (iii) HVR-H3 comprising the amino acid sequence of SEQ ID NO:6; and (b) a VL domain comprising at least one, at least two, or all three VL HVR sequences selected from (i) HVR-L1 comprising the amino acid sequence of SEQ ID NO:21, (ii) HVR-L2 comprising the amino acid sequence of SEQ ID NO:2, and (c) HVR-L3 comprising the amino acid sequence of SEQ ID NO:22.

In another aspect, the invention provides an antibody comprising (a) HVR-H1 comprising the amino acid sequence of SEQ ID NO:87; (b) HVR-H2 comprising the amino acid sequence of SEQ ID NO:88; (c) HVR-H3 comprising the amino acid sequence of SEQ ID NO:89; (d) HVR-L1 comprising the amino acid sequence of SEQ ID NO:85; (e) HVR-L2 comprising the amino acid sequence of SEQ ID NO:58; and (f) HVR-L3 comprising the amino acid sequence of SEQ ID NO:86. In one embodiment, the invention provides an antibody comprising (a) HVR-H1 comprising the amino acid sequence of SEQ ID NO:25; (b) HVR-H2 comprising the amino acid sequence of SEQ ID NO:26; (c) HVR-H3 comprising the amino acid sequence of SEQ ID NO:27; (d) HVR-L1 comprising the amino acid sequence of SEQ ID NO:23; (e) HVR-L2 comprising the amino acid sequence of SEQ ID NO:2; and (f) HVR-L3 comprising the amino acid sequence of SEQ ID NO:24.

In another embodiment, the invention provides an antibody comprising (a) HVR-H1 comprising an amino acid sequence selected from SEQ ID NO:4, 20, 47-51 and 75-80; (b) HVR-H2 comprising an amino acid sequence selected from SEQ ID NO:5, 52 and 81-82; (c) HVR-H3 comprising an amino acid sequence selected from SEQ ID NO:6, 53 and 83-84; (d) HVR-L1 comprising an amino acid sequence selected from SEQ ID NO:1, 18, 21, 33 and 54-57; (e) HVR-L2 comprising an amino acid sequence selected from SEQ ID NO:2 and 58; and (f) HVR-L3 comprising an amino acid sequence selected from SEQ ID NO:3, 19, 22, 34-46 and 59-74.

In another embodiment the invention provides an antibody comprising (a) HVR-H1 comprising the amino acid sequence of SEQ ID NO:4; (b) HVR-H2 comprising the amino acid sequence of SEQ ID NO:5; (c) HVR-H3 comprising the amino acid sequence of SEQ ID NO:6; (d) HVR-L1 comprising the amino acid sequence of SEQ ID NO:1; (e) HVR-L2 comprising the amino acid sequence of SEQ ID NO:2; and (f) HVR-L3 comprising the amino acid sequence of SEQ ID NO:3.

In another embodiment the invention provides an antibody comprising (a) HVR-H1 comprising the amino acid sequence of SEQ ID NO:20; (b) HVR-H2 comprising the amino acid sequence of SEQ ID NO:5; (c) HVR-H3 comprising the amino acid sequence of SEQ ID NO:6; (d) HVR-L1 comprising the amino acid sequence of SEQ ID NO:18; (e) HVR-L2 comprising the amino acid sequence of SEQ ID NO:2; and (f) HVR-L3 comprising the amino acid sequence of SEQ ID NO:19.

In another embodiment the invention provides an antibody comprising (a) HVR-H1 comprising the amino acid sequence of SEQ ID NO:20; (b) HVR-H2 comprising the amino acid sequence of SEQ ID NO:5; (c) HVR-H3 comprising the amino acid sequence of SEQ ID NO:6; (d) HVR-L1 comprising the amino acid sequence of SEQ ID NO:21; (e) HVR-L2 comprising the amino acid sequence of SEQ ID NO:2; and (f) HVR-L3 comprising the amino acid sequence of SEQ ID NO:22.

In any of the above embodiments, an anti-HtrA1 antibody is humanized. In one embodiment, an anti-HtrA1 antibody comprises HVRs as in any of the above embodiments, and further comprises an acceptor human framework, e.g. a human immunoglobulin framework or a human consensus framework. In another embodiment, an anti-HtrA1 antibody comprises HVRs as in any of the above embodiments, and further comprises a VH comprising an FR2 sequence of SEQ ID NO:17.

In another aspect, an anti-HtrA1 antibody comprises a heavy chain variable domain (VH) sequence having at least 90%, 91%, 92%, 93%, 94%, 95%, 96%, 97%, 98%, 99%, or 100% sequence identity to the amino acid sequence of any one of SEQ ID NO:8 or 29. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HtrA1 antibody comprising that sequence retains the ability to bind to HtrA1. In certain embodiments, a total of 1 to 10 amino acids have been substituted, inserted and/or deleted in SEQ ID NO:8 or 29. In certain embodiments, substitutions, insertions, or deletions occur in regions outside the HVRs (i.e., in the FRs). Optionally, the anti-HtrA1 antibody comprises the VH sequence in SEQ ID NO:8, 29 or 32, including post-translational modifications of that sequence. In a particular embodiment, the VH comprises one, two or three HVRs selected from: (a) HVR-H1 comprising an amino acid sequence selected from: SEQ ID NO:4, 20, 25 and 47-51, (b) HVR-H2 comprising an amino acid sequence selected from SEQ ID NO:5, 26 and 52, and (c) HVR-H3 comprising an amino acid sequence selected from SEQ ID NO:6, 27 and 53.

In another aspect, an anti-HtrA1 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of any one of SEQ ID NO:7, 28 or 30. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-HtrA1 antibody comprising that sequence retains the ability to bind to HtrA1. In certain embodiments, a total of 1 to 10 amino acids have been substituted, inserted and/or deleted in SEQ ID NO:7, 28 or 30. In certain embodiments, the substitutions, insertions, or deletions occur in regions outside the HVRs (i.e., in the FRs). Optionally, the anti-HtrA1 antibody comprises the VL sequence in SEQ ID NO:7, 28, 30 or 31, including post-translational modifications of that sequence. In a particular embodiment, the VL comprises one, two or three HVRs selected from (a) HVR-L1 comprising an amino acid sequence selected from SEQ ID NO:1, 18, 21, 23 and 33; (b) HVR-L2 comprising the amino acid sequence of SEQ ID NO:2; and (c) HVR-L3 comprising an amino acid sequence selected from SEQ ID NO:3, 19, 22, 24 and 34-36.

In another aspect, an anti-HtrA1 antibody is provided, wherein the antibody comprises a VH as in any of the embodiments provided above, and a VL as in any of the embodiments provided above. In one embodiment, the antibody comprises the VH and VL sequences in SEQ ID NO:32 and SEQ ID NO:31, respectively, including post-translational modifications of those sequences. In one embodiment, the antibody comprises the VH and VL sequences in SEQ ID NO:8 and SEQ ID NO:7, respectively, including post-translational modifications of those sequences. In one embodiment, the antibody comprises the VH and VL sequences in SEQ ID NO:29 and SEQ ID NO:28, respectively, including post-translational modifications of those sequences. In one embodiment, the antibody comprises the VH and VL sequences in SEQ ID NO:29 and SEQ ID NO:30, respectively, including post-translational modifications of those sequences.

In a further aspect, the invention provides an antibody that binds to the same epitope as an anti-HtrA1 antibody provided herein. For example, in certain embodiments, an antibody is provided that binds to the same epitope as an anti-HtrA1 antibody comprising a VH sequence of SEQ ID NO:8 and a VL sequence of SEQ ID NO:7. In certain embodiments, an antibody is provided that binds to an epitope of HtrA1 containing residue N224, K248 or both of SEQ ID NO:13, or residues equivalent thereto in a different HtrA1 sequence. In certain embodiments, the epitope of HtrA1 further comprising one or more of the following residues V201, T223, K243, K225, E247 and H220 of SEQ ID NO:13, or amino acids equivalent thereto in a different HtrA1 sequence. In certain embodiments, an antibody is provided that binds to an epitope of HtrA1 containing one or more of residues N224, K248 and V201 or all of the foregoing of SEQ ID NO:13, or residues equivalent thereto in a different HtrA1 sequence. In certain embodiments, an antibody is provided that binds to an epitope of HtrA1 containing one or more of residues N224, K248, V201, T223 and K243 or all of the foregoing of SEQ ID NO:13, or residues equivalent thereto in a different HtrA1 sequence. In certain embodiments, an antibody is provided that binds to an epitope of HtrA1 containing one or more of residues N224, K248, V201, T223, K243, K225, E247 and H22A or all of the foregoing of SEQ ID NO:13, or residues equivalent thereto in a different HtrA1 sequence. In certain embodiments, the epitope is a linear epitope. In other embodiments, the epitope is a conformational epitope.

In a further aspect of the invention, an anti-HtrA1 antibody according to any of the above embodiments is a monoclonal antibody, including a chimeric, humanized or human antibody. In one embodiment, an anti-HtrA1 antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein.

In certain embodiments, an anti-HtrA1 antibody according to any of the above embodiments is not an antibody having a VH sequence of SEQ ID NO:8 and a VL sequence of SEQ ID NO:7.

In a further aspect, an anti-HtrA1 antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for HtrA1 and the other is for any other antigen. In certain embodiments, bispecific antibodies may bind to two different epitopes of HtrA1. Bispecific antibodies may also be used to localize cytotoxic agents to cells which express HtrA1. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to HtrA1 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: H is, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001)).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816, 567. In one embodiment, isolated nucleic acid encoding an anti-HtrA1 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-HtrA1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-HtrA1 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology, Vol.* 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, N.J.), pp. 255-268 (2003).

C. Assays

Anti-HtrA1 antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with Fab94 or IgG94 for binding to HtrA1. In certain embodiments, such a competing antibody binds to the same epitope (e.g., a linear or a conformational epitope) that is bound by Fab94 or IgG94. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized HtrA1 is incubated in a solution comprising a first labeled antibody that binds to HtrA1 (e.g., Fab94 or IgG94) and a second unlabeled antibody that is being tested for its ability to compete with the first antibody for binding to HtrA1. The second antibody may be present in a hybridoma supernatant. As a control, immobilized HtrA1 is incubated in a solution comprising the first labeled antibody but not the second unlabeled antibody. After incubation under conditions permissive for binding of the first antibody to HtrA1, excess unbound antibody is removed, and the amount of label associated with immobilized HtrA1 is measured. If the amount of label associated with immobilized HtrA1 is substantially reduced in the test sample relative to the control sample, then that indicates that the second antibody is competing with the first antibody for binding to HtrA1. See Harlow and Lane (1988) *Antibodies: A Laboratory Manual* ch. 14 (Cold Spring Harbor Laboratory, Cold Spring Harbor, N.Y.).

2. Activity Assays

In one aspect, assays are provided for identifying anti-HtrA1 antibodies thereof having biological activity. Biological activity may include, e.g., blocking, antagonizing, suppressing, interfering, modulating and/or reducing one or more biological activities of HtrA1. Antibodies having such biological activity in vivo and/or in vitro are also provided.

In certain embodiments, an antibody of the invention is tested for such biological activity. In certain embodiments, an anti-HtrA1 antibody binds to HtrA1 and reduces or inhibits its serine protease activity for one or more HtrA1 substrates, including, for example, the H2-Opt peptide, β-casein or BODIPY FL casein substrates as described in the Examples below, or any other suitable HtrA1 substrate. In certain embodiments, an anti-HtrA1 antibody inhibits HtrA1 serine protease activity with an $IC_{50}$ of less than 50 nM, 30 nM, 25 nM, 20 nM, 15 nM, 10 nM, 5 nM, 3 nM, 2.5 nM, 2 nM, 1 nM, or less for one or more HtrA1 substrates. In certain embodiments, an anti-HtrA1 antibody protects photoreceptor cells from degredation, protects the thickness of the outer nuclear layer, or protects electroretinogram functional activity in an ocular disease model, such as the constant light exposure mouse model described in the Examples below.

D. Immunoconjugates

The invention also provides immunoconjugates comprising an anti-HtrA1 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7, 498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $Tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2, 4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SLAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-HtrA1 antibodies provided herein is useful for detecting the presence of HtrA1 in a biological sample. The term "detecting" as used herein encompasses quantitative or qualitative detection. In certain embodiments, a biological sample comprises a cell or tissue, such as a sample comprising photoreceptor cells, retinal pigment epithelium cells, cells of the outer nuclear layer, the inner nuclear layer, Muller cells, ciliary epithelium, or retinal tissue.

In one embodiment, an anti-HtrA1 antibody for use in a method of diagnosis or detection is provided. In a further aspect, a method of detecting the presence of HtrA1 in a biological sample is provided. In certain embodiments, the method comprises contacting the biological sample with an anti-HtrA1 antibody as described herein under conditions permissive for binding of the anti-HtrA1 antibody to HtrA1, and detecting whether a complex is formed between the anti-HtrA1 antibody and HtrA1. Such method may be an in vitro or in vivo method. In one embodiment, an anti-HtrA1 antibody is used to select subjects eligible for therapy with an anti-HtrA1 antibody, e.g. where HtrA1 is a biomarker for selection of patients.

In certain embodiments, a patient suitable for treatment with an anti-HtrA1 antibody may be identified by detecting one or more polymorphisms in the HtrA1 gene or HtrA1 control sequence, such as the HtrA1 promoter polymorphism rs11200638(G/A) (see e.g., A. DeWan, et al., *Science* 314: 989-992 (2006)).

Exemplary disorders that may be diagnosed using an antibody of the invention include ocular disorders, such as, for example, wet age-related macular degeneration (AMD), dry age-related macular degeneration, geographic atrophy (GA), diabetic retinopathy (DA), retinopathy of prematurity (ROP), or polypoidal choroidal vasculopathy (PCV).

In certain embodiments, labeled anti-HtrA1 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-HtrA1 antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other. For example, for treating an ocular disorder associated undesired neovascularization, such as wet AMD, it may be desirable to further provide an anti-angiogenic therapy, such as an anti-VEGF therapy like LUCENTIS™ (ranibizumab). Such active ingredients are suitably present in combination in amounts that are effective for the purpose intended. In other embodiments, treatment of a disease or disorder associated undesirable ocular neovascularization may involve a combination of an anti-HtrA1 antibody and photodynamic therapy (e.g., with MACUGEN™ or VISUDYNE™)

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-HtrA1 antibodies provided herein may be used in therapeutic methods.

In certain embodiments, an anti-HtrA1 antibody is useful for inhibiting the degeneration of retinal cells (such as, for example, retinal pigment epithelium (RPE) cells) or photoreceptor cells in an eye of a patient suffering from or at risk for developing an ocular disorder (e.g., a patient having an HtrA1 polymorphism, increased HtrA1 expression in the eye, or drusen in at least one eye). In certain embodiments, an anti-HtrA1 antibody may be used for slowing the progression to late stage geographic atrophy or dry age-related macular degeneration in an eye of a patient having drusen in the eye to be treated. In certain embodiments, a patient suitable for treatment with an anti-HtrA1 antibody may be identified by detecting the onset of disease in at least one eye of the patient. For example, certain patients may be slected by detecting drusen, geographic atrophy, or choroidal neo-vascularization in one eye, while the other eye is symptom free. Such patients may be good candidates for preventative treatment in the symptom free eye, e.g., to delay the onset or reduce the severity of such symptoms (e.g., drusen, geographic atrophy, and/or choroidal neovascularization) in the symptom free eye. Alternatively, the symptomatic eye may be treated, or both the symptomatic and symptom free eye may be treated in accordance with the methods described herein. Accordingly, an anti-HtrA1 antibody may be used for preventing or inhibiting the progression of an ocular disorder in an eye of patient, wherein the patient has developed drusen, wet AMD, or geographic atrophy in the other eye, but the eye being treated is not yet symptomatic. Alternatively, the symptomatic eye is treated, or both the symptomatic and the symptom free eye are treated.

In another embodiment, an anti-HtrA1 antibody is useful for treating arthritis.

In one aspect, an anti-HtrA1 antibody for use as a medicament is provided. In further aspects, an anti-HtrA1 antibody for use in treating an ocular disease or disorder, such as, for example, AMD (wet or dry), GA, DR, PCV or ROP, is provided. In certain embodiments, an anti-HtrA1 antibody for use in a method of treatment is provided. In certain embodiments, the invention provides an anti-HtrA1 antibody for use in a method of treating an individual having an ocular disease or disorder comprising administering to the individual an effective amount of the anti-HtrA1 antibody. In one such embodiment, the method further comprises administering to the individual an effective amount of at least one additional therapeutic agent, e.g., as described below. In further embodiments, the invention provides an anti-HtrA1 antibody for use in inhibiting degeneration of retinal cells (such as, for example, RPE cells) or photoreceptor cells in an eye of a patient. In certain embodiments, the invention provides an anti-HtrA1 antibody for use in a method of inhibiting degeneration of retinal or photoreceptor cells in an individual comprising administering to the individual an effective amount of the anti-HtrA1 antibody to inhibit degeneration of retinal or photoreceptor cells. In further embodiments, the invention provides an anti-HtrA1 antibody for use in inhibiting HtrA1 serine protease activity in an eye of a patient. In certain embodiments, the invention provides an anti-HtrA1 antibody for use in a method of inhibiting HtrA1 serine protease activity in an eye of an individual comprising administering to the individual an effective amount of the anti-HtrA1 antibody to inhibit HtrA1 serine protease activity in the eye. An "individual" according to any of the above embodiments is preferably a human. In further embodiments, the invention provides an anti-HtrA1 antibody for use in inhibiting PCV in a patient in need thereof, e.g., a patient having choroidal vascular networks with polyp-like aneurysmal dilations.

In a further aspect, the invention provides for the use of an anti-HtrA1 antibody in the manufacture or preparation of a medicament. In one embodiment, the medicament is for treatment of an ocular disorder, such as, for example, AMD (wet or dry), GA, DR, PCV or ROP. In a further embodiment, the medicament is for use in a method of treating an ocular disorder comprising administering to an individual having the ocular disorder an effective amount of the medicament. In one such embodiment, the method further comprises administering to the individual an effective amount of at least one additional therapeutic agent, e.g., as described below. In a further embodiment, the medicament is for inhibiting the degredation of retinal cells or photoreceptor cells in an eye of an individual. In a further embodiment, the medicament is for use in a method of inhibiting degeneration of retinal cells or photoreceptor cells in an individual comprising administering to the individual an amount effective of the medicament to inhibit degeneration of retinal or photoreceptor cells in the individual. In a further embodiment, the medicament is for inhibiting HtrA1 serine protease activity in the eye of an individual. In a further embodiment, the medicament is for use in a method of inhibiting HtrA1 serine protease activity in an eye of an individual comprising administering to the individual an amount effective of the medicament to inhibit HtrA1 serine protease activity in the eye. An "individual" according to any of the above embodiments may be a human.

In a further aspect, the invention provides a method for treating an ocular disorder, such as, for example, AMD (wet or dry), GA, DR, PCV or ROP. In one embodiment, the method comprises administering to an individual having such an ocular disorder an effective amount of an anti-HtrA1 antibody. In one such embodiment, the method further comprises administering to the individual an effective amount of at least one additional therapeutic agent, as described below. An "individual" according to any of the above embodiments may be a human.

In a further aspect, the invention provides a method for inhibiting degeneration of retinal or photoreceptor cells in an individual. In one embodiment, the method comprises administering to the individual an effective amount of an anti-HtrA1 antibody to inhibit degeneration of retinal or photoreceptor cells in the individual. In one embodiment, an "individual" is a human.

In a further aspect, the invention provides a method for inhibiting HtrA1 serine protease activity in an eye of an individual. In one embodiment, the method comprises administering to the individual an effective amount of an anti-HtrA1 antibody to inhibit HtrA1 serine protease activity in an eye of the individual. In one embodiment, an "individual" is a human.

The efficacy of the treatment of an ocular disorder using an anti-HtrA1 antibody, can be measured by various endpoints commonly used in evaluating intraocular diseases, such as, for example, performing an eye exam, measuring intraocular pressure, assessing visual acuity, measuring slit-lamp pressure, assessing intraocular inflammation, measuring the size of CNV, measuring the leakage of CNV (e.g., by Fluorescein angiography), measuring the amount of drusen, measuring the location of drusen, etc. In certain embodiments, vision loss can be assessed, for example, by measuring the mean change in best correction visual acuity (BCVA) from baseline to a desired time point (e.g., where the BCVA is based on Early Treatment Diabetic Retinopathy Study (ETDRS) visual acuity chart and assessment at a test distance of 4 meters), measuring the proportion of subjects who lose fewer than 15 letters in visual acuity at a desired time point compared to baseline, measuring the proportion of subjects who gain greater than or equal to 15 letters in visual acuity at a desired tine point compared to baseline, measuring the proportion of subjects with a visual-acuity Snellen equivalent of $20/2000$ or worse at a desired time point, or measuring the NEI Visual Functioning Questionnaire.

In a further aspect, the invention provides pharmaceutical formulations comprising any of the anti-HtrA1 antibodies provided herein, e.g., for use in any of the above therapeutic methods. In one embodiment, a pharmaceutical formulation comprises any of the anti-HtrA1 antibodies provided herein and a pharmaceutically acceptable carrier. In another embodiment, a pharmaceutical formulation comprises any of the anti-HtrA1 antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is a therapeutic agent suitable for treatment of an ocular disorder associated with undesirable neovascularization in the eye, such as, for example, wet AMD. Suitable therapeutic agents include, for example, anti-angiogenic therapies such as an anti-VEGF therapy like LUCENTIS™ (ranibizumab).

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with photdynamic therapy (e.g., with MACUGEN™ or VISUDYNE™).

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. In an exemplary embodiment, an antibody of the invention (and any additional therapeutic agent) can be administered by intravitreal injection. Dosing can be by any suitable route, e.g. by injections, such as intravenous, intravitreal or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered.

It is understood that any of the above formulations or therapeutic methods may be carried out using an immunoconjugate of the invention in place of or in addition to an anti-HtrA1 antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-HtrA1 antibody.

---

SEQUENCE KEY

Light chain HVRs for Anti-HtrA1 Antibody YW505.94
HVR L1: RASQDVSTAVA (SEQ ID NO: 1)

HVR L2: SASFLYS (SEQ ID NO: 2)

HVR L3: QQSYTTPPT (SEQ ID NO: 3)

Heavy chain HVRs for Anti-HtrA1 Antibody YW505.94
HVR H1: GFNISGYYIH (SEQ ID NO: 4)

SEQUENCE KEY

HVR H2: WIDPYGGDTNYADSVKG (SEQ ID NO: 5)

HVR H3: GTFLTSWGHYFDY (SEQ ID NO: 6)

Light chain VR for Anti-HtrA1 Antibody YW505.94
DIQMTQSPSSLSASVGDRVTITC<u>RASQDVSTAVA</u>WYQQKPGKAPKLLIYS<u>ASFLYS</u>GVPSR
FSGSGSGTDFTLTISSLQPEDFATYYC<u>QQSYTTPPT</u>FGQGTKVEIKR (SEQ ID NO: 7)

Heavy chain VR for Anti-HtrA1 Antibody YW505.94
EVQLVESGGGLVQPGGSLRLSCAAS<u>GFNISGYYIH</u>WVRQAPGKGLEWVG<u>WIDPYGGDTN
YADSVKG</u>RFTISADTSKNTAYLQMNSLRAEDTAVYYCAR<u>GTFLTSWGHYFDY</u>WGQGT
(SEQ ID NO: 8)

Human HtrA1 (full length sequence in caps, protease
domain is underlined, residues N224 and K248 are shaded)
mqipraallpllllllaapasaQLSRAGRSAPLAAGCPDRCEPARCPPQPEHCEGGRARDACGCCEVC
GAPEGAACGLQEGPCGEGLQCVVPFGVPASATVRRRAQAGLCVCASSEPVCGSDANTYA
NLCQLRAASRRSERLHRPPVIVLQRGACGQGQ<u>EDPNSLRHKYNFIADVVEKIAPAVVHIEL
FRKLPFSKREVPVASGSGFIVSEDGLIVTNAHVVT</u>NKHRVKVELKNGATYEAKIKDVDEK
ADIALIKIDHQGKLPVLLLGRSSELRPGEFVVAIGSPFSLQNTVTTGIVSTTQRGGKELGLRN
SDMDYIQTDAIINYGNSGGPLVNLDGEVIGINTLKVTAGISFAIPSDKIKKFLTESHDRQAKG
KAITKKKYIGIRMMSLTSSKAKELKDRHRDFPDVISGAYIIEVIPDTPAEAGGLKENDVIISIN
GQSVVSANDVSDVIKRESTLNMVVRRGNEDIMITVIPEEIDP</u> (SEQ ID NO: 13)

Murine HtrA1 (full length sequence in caps,
protease domain is underlined)
mqslrttllsllllllaapslalPSGTGRSAPAATVCPEHCDPTRCAPPPTDCEGGRVRDACGCCEVCGA
LEGAACGLQEGPCGEGLQCVVPFGVPASATVRRRAQAGLCVCASSEPVCGSDAKTYTNL
CQLRAASRRSEKLRQPPVIVLQRGAC<u>GQGQEDPNSLRHKYNFIADVVEKIAPAVVHIELYR
KLPFSKREVPVASGSGFIVSEDGLIVTNAHVVTNKNRVKVELKNGATYEAKIKDVDEKAD
IALIKIDHQGKLPVLLLGRSSELRPGEFVVAIGSPFSLQNTVTTGIVSTTQRGGKELGLRNSD
MDYIQTDAIINYGNSGGPLVNLDGEVIGINTLKVTAGISFAIPSDKIKKFLTESHDRQAKGK
AVTKKKYIGIRMMSLTSSKAKELKDRHRDFPDVLSGAYIIEVIPDTPAEAGGLKENDVIISIN
GQSVVTANDVSDVIKKENTLNMVVRRGNEDIVITVIPEEIDP</u> (SEQ ID NO: 14)

Murine HtrA3 (protease domain is underlined)
MQARALLPATLAILATLAVLALAREPPAAPCPARCDVSRCPSPRCPGGYVPDLCNCCLVC
AASEGEPCGRPLDSPCGDSLECVRGVCRCRWTHTVCGTDGHTYADVCALQAASRRALQ
VSGTPVRQLQKGAC<u>PSGLHQLTSPRYKFNFIADVVEKIAPAVVHIELFLRHPLFGRNVPLSS
GSGFIMSEAGLIVTNAHVVSSSSTASGRQQLKVQLQNGDAYEATIQDIDKKSDIATIVIHPK
KKLPVLLLGHSADLRPGEFVVAIGSPFALQNTVTTGIVSTAQRDGKELGLRDSDMDYIQTD
AIINYGNSGGPLVNLDGEVIGINTLKVAAGISFAIPSDRITRFLSEFQNKHVKDWKKRFIGIR
MRTITPSLVEELKAANPDFPAVSSGIYVQEVVPNSPSQRGGIQDGDIIVKVNGRPLADSSEL
QEAVLNESSLLLEVRRGNDDLLFSIIPEVVM</u> (SEQ ID NO: 15)

Murine HtrA4 (protease domain is underlined)
MSFQRLWAVRTQFLLLWLLLPAVPVPWAEARRSRVSLPCPDACDPTRCPTLPTCSAGLAP
VPDRCGCCRVCAAAEGQECGGARGRPCAPRLRCGAPFSRDPSGGAWLGTCGCAEGAED
AVVCGSDGRTYPSLCALRKENRAARQRGALPVPVQKGAC<u>EEAGTTRAGRLRRKYNFIA
AVVEKVAPSVVHLQLFRRSPLTNQEIPSSSGSGFIVSEDGLIVTNAHVLTNQQKIQVELQSG
ARYEATVKDIDHKLDLALIKIEPDTELPVLLLGRSSDLRAGEFVVALGSPFSLQNTVTAGIV
STTQRGGRELGLKNSDIDYIQTDAIINHGNSGGPLVNLDGDVIGINTLKVTAGISFAIPSDRIR
QFLEDYHERQLKGKAPLQKKYLGLRMLPLTLNLLQEMKRQDPEFPDVSSGVFVYEVIQGS
AAASSGLRDHDVIVSINGQPVTTTTDVIEAVKDNDFLSIIVLRGSQTLFLTVTPEIIN</u> (SEQ ID
NO: 16)

YW505.95 HC FR2
WVRQAPGKGLEWVG (SEQ ID NO: 17)

Light chain HVRs for Anti-HtrA1 Antibody YW505.94a.28
HVR L1: RASQSINTYLA (SEQ ID NO: 18)
HVR L2: SASFLYS (SEQ ID NO: 2)
HVR L3: QQSDDTPPT (SEQ ID NO: 19)

Heavy chain HVRs for Anti-HtrA1 Antibody YW505.94a.28
HVR H1: GFSISGYYIH (SEQ ID NO: 20)
HVR H2: WIDPYGGDTNYADSVKG (SEQ ID NO: 5)
HVR H3: GTFLTSWGHYFDY (SEQ ID NO: 6)

Light chain VR for Anti-HtrA1 Antibody YW505.94a.28
DIQMTQSPSSLSASVGDRVTITC<u>RASQSINTYLA</u>WYQQKPGKAPKLLIYS<u>ASFLYS</u>GVPSRF
SGSGSGTDFTLTISSLQPEDFATYYC<u>QQSDDTPPT</u>FGQGTKVEIKR (SEQ ID NO: 28)

Heavy chain VR for Anti-HtrA1 Antibody YW505.94a.28
EVQLVESGGGLVQPGGSLRLSCAAS<u>GFSISGYYIH</u>WVRQAPGKGLEWVG<u>WIDPYGGDTN
YADSVKG</u>RFTISADTSKNTAYLQMNSLRAEDTAVYYCAR<u>GTFLTSWGHYFDY</u>WGQGT (SEQ ID NO: 29)

-continued

SEQUENCE KEY

Light chain HVRs for Anti-HtrA1 Antibody YW505.94a.54
HVR L1: RASQVVGNYLA (SEQ ID NO: 21)
HVR L2: SASFLYS (SEQ ID NO: 2)
HVR L3: QQSDDHPPT (SEQ ID NO: 22)

Heavy chain HVRs for Anti-HtrA1 Antibody YW505.94a.54
HVR H1: GFSISGYYIH (SEQ ID NO: 20)
HVR H2: WIDPYGGDTNYADSVKG (SEQ ID NO: 5)
HVR H3: GTFLTSWGHYFDY (SEQ ID NO: 6)

Light chain VR for Anti-HtrA1 Antibody YW505.94a.54
DIQMTQSPSSLSASVGDRVTITCRASQVVGNYLAWYQQKPGKAPKLLIYSASFLYSGVPSR
FSGSGSGTDFTLTISSLQPEDFATYYCQQSDDHPPTFGQGTKVEIKR (SEQ ID NO: 30)

Heavy chain VR for Anti-HtrA1 Antibody YW505.94a.54
EVQLVESGGGLVQPGGSLRLSCAASGFSISGYYIHWVRQAPGKGLEWVGWIDPYGGDTN
YADSVKGRFTISADTSKNTAYLQMNSLRAEDTAVYYCARGTFLTSWGHYFDYWGQGT
(SEQ ID NO: 29)

Light chain HVR Consensus Sequences
HVR L1: RASQX$_a$X$_b$X$_c$X$_d$X$_e$X$_f$A, wherein X$_a$ is D, S or V;
X$_b$ is V or I; X$_c$ is S, N or G; X$_d$ is T or
N; X$_e$ is A or Y; and X$_f$ is V or L (SEQ ID NO: 23);
HVR L2: SASFLYS (SEQ ID NO: 2)
HVR L3: QQX$_g$X$_h$X$_i$X$_j$PX$_k$T, wherein X$_g$ is S, V or D;
X$_h$ is Y, D or S; X$_i$ is T, S, A, D or N; X$_j$ is
T, H, N, S, A, L or R; and X$_k$ is P, T, A or S (SEQ ID NO: 24);

Heavy chain HVR Consensus Sequences
HVR H1: GFX$_l$IX$_m$X$_n$YYIH, wherein X$_l$ is N, S or T;
X$_m$ is S, D, Y or A; and X$_n$ is G or D (SEQ ID NO: 25);
HVR H2: WIDPYGGDTX$_o$YADSVKG, wherein X$_o$ is N or D (SEQ ID NO: 26);
HVR H3: GTFLTX$_p$WGHYFDY, wherein X$_p$ is S or T (SEQ ID NO: 27).

Consensus Light chain VR
DIQMTQSPSSLSASVGDRVTITCRASQX$_a$X$_b$X$_c$X$_d$X$_e$X$_f$AWYQQKPGKAPKLLIYSASFLYSG
VPSRFSGSGSGTDFTLTISSLQPEDFATYYCQQX$_g$X$_h$X$_i$X$_j$PX$_k$TFGQGTKVEIKR,
wherein X$_a$ is D, S or V; X$_b$ is V or I; X$_c$ is S, N or G; X$_d$ is T or N;
X$_e$ is A or Y; X$_f$ is V or L; X$_g$ is S, V or D; X$_h$ is Y, D or S;
X$_i$ is T, S, A, D or N; X$_j$ is T, H, N, S, A, L or R; and
X$_k$ is P, T, A or S; (SEQ ID NO: 31)

Consensus Heavy chain VR
EVQLVESGGGLVQPGGSLRLSCAASGFX$_l$X$_m$X$_n$YYIHWVRQAPGKGLEWVGWIDPYGGD
TX$_o$YADSVKGRFTISADTSKNTAYLQMNSLRAEDTAVYYCARGTFLTX$_p$WGHYFDYWGQGT,
wherein X$_l$ is N, S or T; X$_m$ is S, D, Y or A;
X$_n$ is G or D; X$_o$ is N or D; and X$_p$ is S or T (SEQ ID NO: 32)

YW505.94a51 HVR L1: RASQDVGTYLA (SEQ ID NO: 33)

YW505.94a.1 HVR L3: QQVYSHPPT (SEQ ID NO: 34)

YW505.94a.7 HVR L3: QQSYTNPPT (SEQ ID NO: 35)

YW505.94a.22 HVR L3: QQSYATPTT (SEQ ID NO: 36)

YW505.94a.37 HVR L3: QQSYSSPAT (SEQ ID NO: 37)

YW505.94a.39 HVR L3: QQVYTTPPT (SEQ ID NO: 38)

YW505.94a.40 HVR L3: QQVYATPST (SEQ ID NO: 39)

YW505.94a.42 HVR L3: QQSYNSPAT (SEQ ID NO: 40)

YW505.94a.46 HVR L3: QQSYSTPAT (SEQ ID NO: 41)

YW505.94a.50 HVR L3: QQSYTAPTT (SEQ ID NO: 42)

YW505.94a.51 HVR L3: QQDSTLPPT (SEQ ID NO: 43)

YW505.94a.52 HVR L3: QQSDAAPPT (SEQ ID NO: 44)

YW505.94a.78 HVR L3: QQSYSTPPT (SEQ ID NO: 45)

YW505.94a.89 HVR L3: QQSYTRPPT (SEQ ID NO: 46)

-continued

SEQUENCE KEY

YW505.94a.7 HVR H1: GFSISDYYIH (SEQ ID NO: 47)

YW505.94a.26 HVR H1: GFSIDGYYIH (SEQ ID NO: 48)

YW505.94a.38 HVR H1: GFTIYDYYIH (SEQ ID NO: 49)

YW505.94a.78 HVR H1: GFSIAGYYIH (SEQ ID NO: 50)

YW505.94a.82 HVR H1: GFTISDYYIH (SEQ ID NO: 51)

YW505.94A.42 HVR H2: WIDPYGGDTDYADSVKG (SEQ ID NO: 52)

YW505.94A.46 HVR H3: GTFLTTWGHYFDY (SEQ ID NO: 53)

TABLE A

HVR and variable domain sequences for anti-HtrA1 YW505.94 antibody and affinity-improved variants thereof.

| | SEQ ID NOs | | | | | | | |
|---|---|---|---|---|---|---|---|---|
| | H1 | H2 | H3 | L1 | L2 | L3 | HC VR | LC VR |
| Consensus | 25 | 26 | 27 | 23 | 2 | 24 | 32 | 31 |
| YW505.94 | 4 | 5 | 6 | 1 | 2 | 3 | 8 | 7 |
| YW505.94a | 20 | 5 | 6 | 1 | 2 | 3 | 29 | 7 |
| YW505.94a.28 | 20 | 5 | 6 | 18 | 2 | 19 | 29 | 28 |
| YW505.94a.54 | 20 | 5 | 6 | 21 | 2 | 22 | 29 | 30 |
| YW505.94a.1 | 20 | 5 | 6 | 1 | 2 | 34 | | |
| YW505.94a.7 | 47 | 5 | 6 | 1 | 2 | 35 | | |
| YW505.94a.22 | 20 | 5 | 6 | 1 | 2 | 36 | | |
| YW505.94a.26 | 48 | 5 | 6 | 1 | 2 | 3 | | |
| YW505.94a.37 | 47 | 5 | 6 | 1 | 2 | 37 | | |
| YW505.94a.38 | 49 | 5 | 6 | 1 | 2 | 3 | | |
| YW505.94a.39 | 20 | 5 | 6 | 1 | 2 | 38 | | |
| YW505.94a.40 | 20 | 5 | 6 | 1 | 2 | 39 | | |
| YW505.94a.42 | 20 | 52 | 6 | 1 | 2 | 40 | | |
| YW505.94a.46 | 20 | 5 | 53 | 1 | 2 | 41 | | |
| YW505.94a.47 | 20 | 52 | 6 | 1 | 2 | 3 | | |
| YW505.94a.50 | 47 | 5 | 6 | 1 | 2 | 42 | | |
| YW505.94a.51 | 20 | 5 | 6 | 33 | 2 | 43 | | |
| YW505.94a.52 | 20 | 5 | 6 | 1 | 2 | 44 | | |
| YW505.94a.77 | 20 | 5 | 53 | 1 | 2 | 3 | | |
| YW505.94a.78 | 50 | 5 | 6 | 1 | 2 | 45 | | |
| YW505.94a.82 | 51 | 5 | 6 | 1 | 2 | 3 | | |
| YW505.94a.89 | 20 | 52 | 6 | 1 | 2 | 46 | | |

III. Examples

The following are examples of methods and compositions of the invention. It is understood that various other embodiments may be practiced, given the general description provided above.

Example 1: Generation of Anti-HtrA1 Antibodies

Phage Display.

Synthetic antibody libraries displayed bivalent Fab fragments on the M13 phage and the diversity was generated by use of oligo-directed mutagenesis in three complementarity determining regions (CDRs) of the heavy chain. The details of the Fab libraries were described previously (Lee, C. V., et al., *J Mol. Biol.* 340:1073-93 (2004); Lee, C. V., et al., *J Immunol Methods.* 284:119-32 (2004)). Nunc 96-well Maxisorp immunoplates were coated overnight at 4° C. with MuHtrA1_PD (10 µg/ml) and then blocked for 1 h at room temperature with phage blocking buffer (PBS, 1% (w/v) BSA, 0.05% (v/v) Tween 20). The antibody phage libraries were added to the MuHtrA1_PD-coated plates and incubated overnight at room temperature. The plates were washed with PBS, 0.05% (v/v) Tween-20 buffer and bound phage were eluted with 50 mM HCl-500 mM NaCl for 30 min and neutralized with an equal volume of 1 M Tris-HCl, pH 7.5. Recovered phage was amplified in *E. coli* XL-1 blue cells. During subsequent selection rounds, incubation of antibody phage with the antigen-coated plates was reduced to 2-3 hours and the stringency of plate washing was gradually increased. 13 identified clones were reformatted to IgG (as described below for Fab94), expressed in 293 cells and purified by Protein A affinity chromatography. The 13 purified IgG bound to MuHtrA1_PD in a binding ELISA.

Anti-HtrA1 Fab94 and IgG94 Expression and Purification.

The variable regions of both the heavy and light chains of Fab94 (YW505.94) were subcloned into a *E. coli* Fab expression vector (AEP1). The resulting plasmid was transformed into *E. coli.* strain 34B8. The single colony was grown overnight at 37° C. in 30 ml LB medium supplemented with 50 µg/ml of Carbenicilin. Five ml of the culture was inoculated into 500 ml of complete C.R.A.P. medium (Simmons, L. C., et al., *J Immunol Methods.* 263:133-47 (2002)) supplemented with Carbenicilin (50 µg/ml) and grown at 30° C. for 24 h. The Fab94 protein was purified using protein A agarose resin.

The variable domains of both the light chain and heavy chain of Fab94 were cloned into a pRK5-based plasmid with human light chain or heavy chain (human IgG1) constant domain for transient expression in Chinese hamster ovary (CHO) cells. The IgG94 protein was purified by use of protein A agarose chromatography.

The amino acid sequences for the light chain variable region and heavy chain variable region for Fab94 (YW505.94) are shown in FIGS. 1A and 1B, respectively.

Example 2: Production of HtrA1 Proteins

Protein Constructs.

Full length human HtrA1 (HuHtrA1) (Q23-P480) and full length murine HtrA1 (MuHtrA1) (P24-P480) were cloned by PCR amplification from full length clones using Taq polymerase. The primers contained the nucleotides required for adding portions of the restriction sites BamHI and EcoRI to the resulting PCR products. The PCR fragments were ligated into a modified pAcGP67 baculovirus transfer vector (BD Pharmingen) containing a $His_6$ sequence (SEQ ID NO: 90) upstream of the BamHI restriction site resulting in an N-terminal $His_6$ tag (SEQ ID NO: 90) on the HtrA1 proteins.

The protease domain of human HtrA1 (HtrA1_PD) lacking the N-domain and the PDZ domain (e.g., containing residues D161-K379) was cloned by PCR amplification. The amplified DNA was inserted into a modified pET vector resulting in an N-terminal His$_6$ tag (SEQ ID NO: 90) and a thrombin cleavage site fused upstream of the D161 codon of HtrA1. HtrA1_PD Ala mutants were generated using the QuikChange XL site-directed mutagenesis kit according to the manufacturer's protocol (Agilent Technologies, Santa Clara Calif.). Constructs were verified by DNA sequencing. The protease domains of murine HtrA1 (MuHtrA1_PD) (G156-S367), murine HtrA3 (MuHtrA3_PD) (P133-F350) and murine HtrA4 (MuHtrA4_PD) (E159-Y371) were cloned from full length clones using Pfu (Agilent) polymerase. The primers contained the nucleotides required for adding the restriction sites Not I and Stu I to the resulting PCR products. The PCR fragments were ligated into pST23 of an expression vector with a phoA promoter. This expression vector contains the amino acid sequences MK(HQ)$_6$ MHQSTAA (SEQ ID NO: 11) upstream of the Not I restriction site resulting in N-terminal fusion of unizyme tag to the protease domains.

As described herein, amino acid residues of huHtrA1, muHtrA1, muHtrA3, and muHtrA4 are made with reference to SEQ ID NOs:13-16, respectively. Amino acids positions are specified by the one letter amino acid code followed by its position within one of SEQ ID NOs:13-16. For example, full length huHtrA1 comprises a sequence starting at glutamine at position 23 of SEQ ID NO:13 and ending at proline at position 480 of SEQ ID NO:13, e.g., Q23-P480. Similarly, mutations at a particular position within an HtrA protein are designated by the starting amino acid, followed by the position within one of SEQ ID NOs:13-16, followed by the substituted amino acid. For Example, a mutation of Lysine at position 248 of HuHtrA1 (SEQ ID NO:13) to alanine is referred to as K248A.

Protein Expression and Purification.

HuHtrA1 and MuHtrA1 were expressed in *Trichoplusia ni* insect cells (Expression Systems LLC, Woodland, Calif.). Harvested insect cell media (after pH was adjusted to 6.8) had NiCl$_2$, CaCl$_2$, and NaCl added to final concentrations of 1.0, 2.5 and 150 mM respectively.

HuHtrA1_PD constructs (wildtype and S328A mutant) were expressed in *E. coli* BL21 (Stratagene). *E. coli* cultures were grown at 37° C. in LB medium containing 50 μg/ml carbenicillin until A$_{600}$ reached 0.8 to 1.0 and then induced with 0.4 mM IPTG and grown at 16° C. for 24 h. The bacterial cell pellets were resuspended in $\frac{1}{10}^{th}$ culture volume of 50 mM Tris pH 8.0, 500 mM NaCl and disrupted using a Microfluidizer. Lysates were centrifuged at 30,000×g for 30 min.

HuHtrA1, MuHtrA1, HuHtrA1_PD and HuHtrA1_PD (S328A) were purified using nickel-nitrilo-triacetic acid resin (Qiagen). After loading insect cell media or *E. coli* lysates, columns were washed with 10 column volumes (CV) of 50 mM Tris pH 8.0, 500 mM NaCl followed by 10 CV of 50 mM Tris pH 8.0, 1 M NaCl, 20 mM imidazole. Proteins were eluted with 50 mM Tris pH 8.0, 200 mM NaCl, 10% glycerol, 0.25% CHAPS, 300 mM imidazole. Pooled fractions were further purified by size exclusion chromatography on a S-200 column (GE Healthcare) and peak fractions corresponding to the trimeric protein forms were collected. Protein purity was greater than 90% as assessed by SDS-PAGE and protein concentrations were determined using the BCA™ protein assay (Pierce, Rockford, Ill.).

HuHtrA1_PD Ala mutants (panel of 15 mutants except S328A) were expressed as described for the wildtype form of HuHtrA1_PD (see above). Lysis buffer (PopCulture, EMD Chemical, San Diego Calif.) was added to bacterial cell pellets at 50 ml lysis buffer/500 ml pellet. The pellet was suspended completely in lysis buffer with a polytron and stirred at room temperature for 30 min. The cell lysate was centrifuged (Beckman, LA-16.250 rotor) at 33,700×g for 30 min at 4° C. and the resulting supernatant was filtered through a 0.22 μm filter unit (Nalgene). The filtered supernatant was loaded onto a Ni-NTA column (3 ml, Qiagen) pre-equilibrated with 50 mM Tris, 300 mM NaCl, 10 mM imidazole, 10% glycerol pH 8.0 (buffer A). Once loaded the column was washed with 12 CV of buffer A followed by 20 CV of buffer A+0.1% Triton X-114. The column was washed again with 15 CV of buffer A to remove detergent. Proteins were eluted with buffer A+200 mM imidazole, 0.25% CHAPS. Pooled Fractions were further purified with Superdex 200 (Hi load 16/60, 120 ml, GE Healthcare) equilibrated with 50 mM Tris pH 8.0, 200 mM NaCl, 10% glycerol, 0.25% CHAPS. The fractions corresponding to the HtrA1_PD trimer peak were pooled. Protein purity was greater than 90% as assessed by SDS-PAGE and protein concentrations were determined by use of the BCA™ protein assay (Pierce, Rockford, Ill.).

MuHtrA1_PD, MuHtrA3_PD and MuHtrA4_PD were expressed in *E. coli* 58F3 (Szeto, W., et al., *Cancer Res.* 61:4197-205 (2001)). Overnight *E. coli* cultures, grown at 30° C. in LB medium containing 50 μg/ml carbenicillin, were diluted ($\frac{1}{100}$ vol) into a larger culture containing C.R.A.P. medium (Simmons, L. C., et al., *J Immunol Methods.* 263:133-47 (2002)) supplemented with 50 μg/ml carbenicillin. After inoculation *E. coli* were grown for approximately 20 h at 30° C. MuHtrA1_PD was purified as described for HuHtrA1_PD (see above). For purification of MuHtrA3_PD and MuHtrA4_PD, lysis buffer (50 mM Tris pH 8.5, 500 mM NaCl, 10 mM imidazole, 10% glycerol) was added to the bacterial cell pellet. The pellet was homogenized in lysis buffer with a polytron and cells disrupted with a mircofludizer. The cell lysate was centrifuged and the resulting supernatant filtered through a 0.22 μm filter unit (Nalgene). The filtered supernatant was loaded onto a 3 ml Ni-NTA column (Qiagen) pre-equilibrated with 25 mM Tris pH 8.5, 500 mM NaCl, 20 mM imidazole, 10% glycerol (buffer B). After loading, the column was washed with 12 CV of buffer B followed by 20 CV of buffer B+0.1% Triton X-114. The column was washed again with 15 CV of buffer B to remove detergent. Proteins were eluted with 25 mM Tris pH 8.5, 500 mM NaCl, 250 mM imidazole, 10% glycerol, 0.25% CHAPS. Pooled fractions were further purified on a 120 ml Superdex 75 (GE Healthcare) equilibrated with 25 mM Tris pH 8.5, 10% glycerol, 0.5 mM TCEP, 0.25% CHAPS. The fractions corresponding to the protease trimer peak were pooled. Protein purity was greater than 90% as assessed by SDS-PAGE.

Example 3: Determination of Inhibitory Activity of Anti-HtrA1 Antibodies Using a FRET Assay Synthesis of Peptide Substrate.

The peptide H2-Opt (Mca-IRRVSYSF(Dnp)KK) (SEQ ID NO:12), originally described as a substrate for HtrA2 (Martins, L. M., et al., *J Biol. Chem.* 278:49417-27 (2003)), was synthesized on Fmoc-Lys(Boc)-wang resin using standard coupling procedures with HBTU. Fmoc-Lys(DNP)—OH (Anaspec) was incorporated in the P5' position. The peptide was synthesized up to P5 (Mca, 7-Methoxy-coumarin, Aldrich) and then cleaved from the solid support using trifluoroacetic acid, triisoproplysilane and water for 2 hours at room temperature. Peptide was precipitated from ethyl ether, extracted with acetic acid, acetonitrile, water and lyophilized. Crude labeled peptide was dissolved and purified on preparative reverse phase C18 column using acetonitrile/water. Purified fractions were pooled, lyophilized and analyzed by liquid chromatography/mass spectrometry (PE/Sciex) and found to be consistent with their calculated masses.

Enzymatic Assays with Peptide Substrate.

HtrA1 was incubated in 96-well black optical bottom plates (Nalge Nunc Int., Rochester, N.Y.) with IgG94 or Fab94 serially diluted in 50 mM Tris-HCl, pH 8.0, 200 mM NaCl, 0.25% CHAPS (assay buffer) for 20 min at 37° C. For initial testing a panel of 13 phage derived anti-HtrA1 antibodies, single concentrations of IgGs (final concentrations 0.16 mg/ml-0.28 mg/ml) were incubated with HuHtrA1 or HuHtrA1_PD. A 10 mM stock solution of the peptide substrate Mca-IRRVSYSF(Dnp)KK (SEQ ID NO:12) (H2-Opt) in DMSO was diluted in water to 12.5 µM, pre-warmed at 37° C. and then added to the reaction mixture. The final concentrations of the reactants were: 5 nM HuHtrA1 or MuHtrA1, 0.005-300 nM IgG94, 0.02-900 nM Fab94, 2.5 µM H2-Opt. The increase of fluorescence signal (excitation 328 nm, emission 393 nm) was measured on a SPECTRAmax M5 microplate reader (Molecular Devices, Sunnyvale, Calif.) and the linear rates of H2-Opt cleavage (mRFU/min) determined. Experiments with IgG94 inhibition of trypsin (Roche) and elastase (MP Biomedicals) were carried out identically, except that the final enzyme concentrations were 1 nM, the IgG94 concentration was 300 nM and the incubation time was 15 min.

As shown in FIG. 2, a panel of 13 phage derived antibodies (IgG) was incubated with HuHtrA1 or HuHtrA1_PD and enzyme activity measured. Of the 13 antibodies tested, antibodies YW503.57, YW504.57, YW504.61 and YW505.94 (also referred to as Fab94, antibody 94, Ab94 or IgG94) strongly inhibited both HuHtrA1 and HuHtrA1_PD activities.

Figure 3:
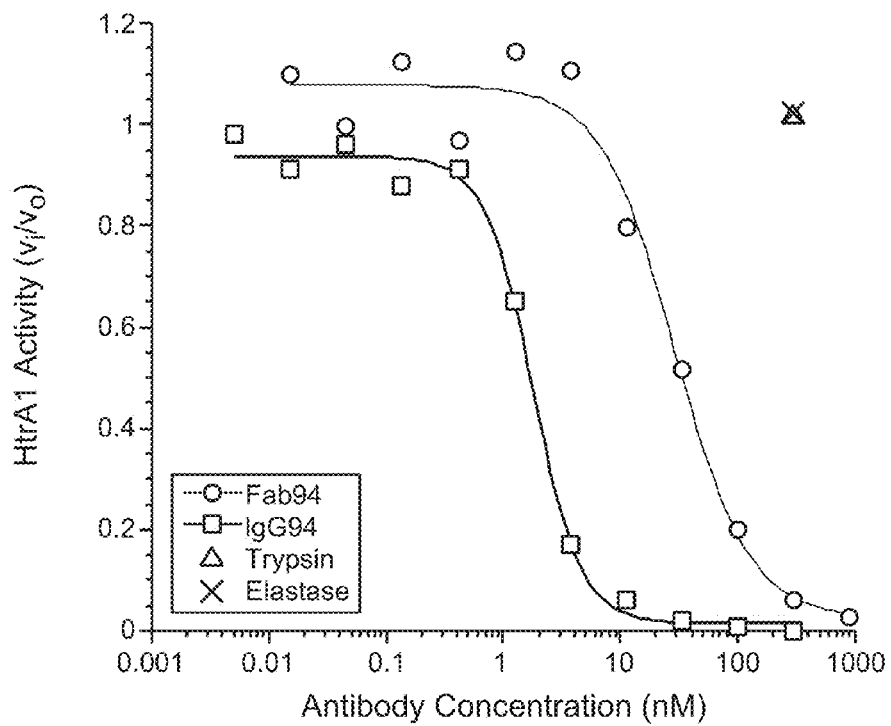
FIG. 3. Inhibition of HuHtrA1 by IgG94 and Fab94. HuHtrA1 was incubated with IgG94 and Fab94 for 20 min at 37° C. Enzyme activity towards the peptide substrate H2-Opt was measured and fractional activities ($v_i/v_o$) calculated from the determined linear velocities. IgG94 at 300 nM did not inhibit H2-Opt hydrolysis by trypsin (1 nM) or elastase (1 nM).

As shown in FIG. 3, IgG94 inhibited the enzymatic activity of HuHtrA1 towards the H2-Opt substrate in a concentration-dependent fashion with an $IC_{50}$ value of 1.8 nM. Complete inhibition was achieved above 30 nM IgG94. In contrast, two other members of the trypsin-like serine protease family, trypsin and elastase, were not inhibited by IgG94 at 300 nM, indicating that IgG94 has specificity towards HuHtrA1. Fab94 also inhibited HuHtrA1 in a concentration-dependent manner, but less potently than IgG94 as indicated by the $IC_{50}$ value of 29.1 nM. These results are in excellent agreement with the $K_D$ value of 31.1 nM determined by surface plasmon resonance experiments (see Table 1 below). The results show that IgG94 and Fab94 are able to completely neutralize the enzymatic activity of HuHtrA1 towards a small synthetic peptide substrate and that this activity is specific. Moreover, the about 16-fold increase in potency of IgG94 vs. Fab94 is consistent with the avidity effects predicted from the 'cage-like' IgG94:HuHtrA1 complex based on mass analysis (see e.g., Table 2 and FIG. 9).

The inhibitory potencies of affinity-improved variant antibody YW505.94a.28 was also determined using the assay described above with the fluorescence quenched peptide substrate H2-Opt and 1.0 nM of HuHtrA1 or 1.5 nM of HuHtrA1_PD. The results are shown below.

| YW505.94a.28 format | HuHtrA1_PD $IC_{50}$ nM | HuHtrA1 $IC_{50}$ nM |
|---|---|---|
| IgG | 0.229 | 0.335 |
| Fab | 2.03 | 1.95 |

Example 4: Determination of Inhibitory Activity of Anti-HtrA1 Antibodies Using Macromolecular Substrates Bovine β-casein (Sigma-Aldrich) was repurified on a MonoQ ion exchange column to yield highly purified material. HuHtrA1 was incubated in Eppendorf tubes together with increasing concentrations of IgG94 in assay buffer for 15 min at 37° C. after which the macromolecular substrates were added. For β-casein digestion, the final concentration of reactants were: 10 nM HuHtrA1, 50 µg/ml β-casein, 2.3-150 nM IgG94. For decorin the final concentrations were: 125 nM HuHtrA1, 50 µg/ml decorin (R & D Systems), 2-125 nM IgG94. For biglycan the final concentrations were: 75 nM HuHtrA1, 50 µg/ml biglycan (R & D Systems), 2.3-150 nM IgG94. After incubation at 37° C. (2 h for β-casein, 14 h for decorin, 6 h for biglycan), SDS sample buffer was added and samples boiled and analyzed by SDS-PAGE (non-reducing).

Hydrolysis of fluorescent dye-labeled casein, BODIPY FL casein (Invitrogen), was carried out in 96-well black optical bottom plates (Nalge Nunc Int., Rochester, N.Y.). HuHtrA1 or MuHtrA1 were incubated with IgG94 serially diluted in assay buffer for 15 min at 37° C. After addition of BODIPY FL in assay buffer, the reactant concentrations were as follows: 30 nM HuHtrA1, 30 nM MuHtrA1, 5 µg/ml BODIPY FL, 0.24-250 nM IgG94. The increase of fluorescence signal (excitation 484 nm, emission 535 nm) was measured on a SPECTRAmax M5 microplate reader (Molecular Devices, Sunnyvale, Calif.) and the linear rates of BODIPY FL cleavage (mRFU/min) determined and expressed as percentage of uninhibited rates (control).

Figure 6:
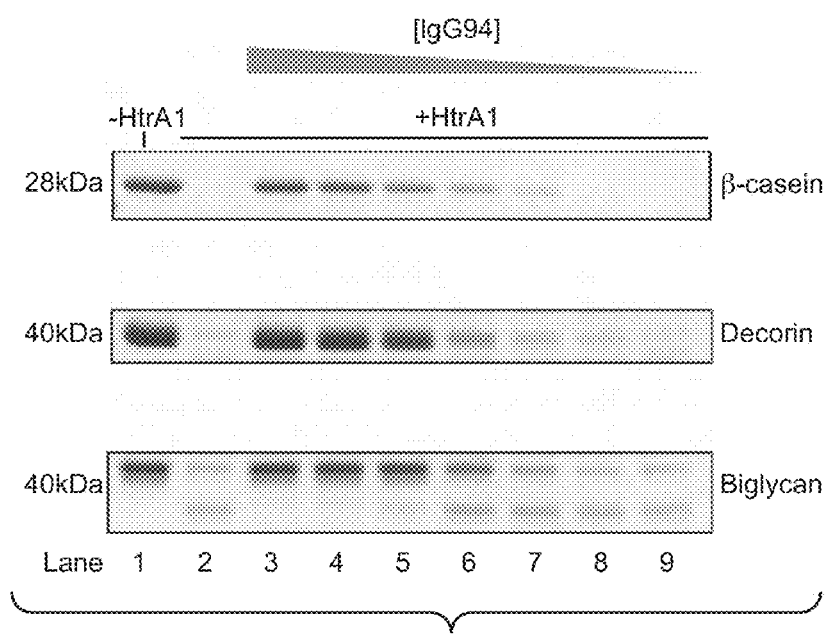
FIG. 6. Inhibition of HuHtrA1-mediated macromolecular substrate cleavage by IgG94. Increasing concentrations of IgG94 (2.3-150 nM for β-casein; 2-125 nM for decorin; 2.3-150 nM for biglycan) were incubated with HuHtrA1 (10 nM for β-casein, 125 nM for decorin, 75 nM for biglycan) for 15 min at 37° C. The substrates β-casein, decorin and biglycan (50 μg/ml) were added and incubated for 2-14 h. After addition of SDS-sample buffer the digests were analyzed by SDS-PAGE (non-reducing conditions) and stained by SimplyBlue Safestain.

As shown in FIG. 6, HuHtrA1 degraded the macromolecular substrates β-casein, decorin and biglycan (lane 2). In the absence of HuHtrA1, the substrates remained intact during the experimental period (FIG. 6, lane 1). Preincubation of HuHtrA1 with increasing concentrations of IgG94 (FIG. 6, lane 9-lane 3) resulted in a concentration-dependent inhibition of substrate degradation. At the highest IgG94 concentrations tested, degradation of β-casein, decorin and biglycan was completely prevented (FIG. 6, lane 3). The results show that IgG94 potently and effectively inhibited HuHtrA1 activity towards three macromolecular substrates.

Figure 4:
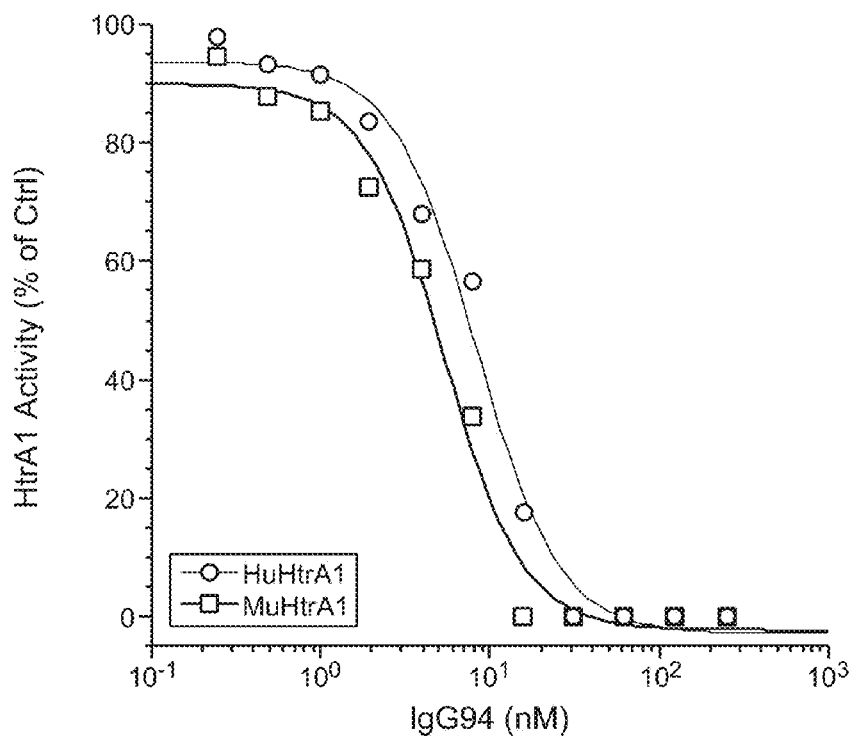
FIG. 4. IgG94 inhibits hydrolysis of fluorescent dye-labeled casein (BODIPY FL) by HuHtrA1 and MuHtrA1. HuHtrA1 and MuHtrA1 were incubated with IgG94 for 15 min at 37° C. Hydrolysis of casein BODIPY FL reagent was measured on a microplate reader at 37° C. and the linear rates of fluorescence increase determined and expressed as percent of uninhibited rates (% of control).

As shown in FIG. 4, IgG94 concentration-dependently inhibited BODIPY FL hydrolysis by both HuHtrA1 and MuHtrA1 with $IC_{50}$ values of 8.3 nM and 5.4 nM, respectively. The results show that IgG94 recognizes and completely neutralizes the enzymatic activities of both HuHtrA1 and MuHtrA1 towards the macromolecular substrate BODIPY FL.

Example 5: Determination of the Specificity of Anti-HtrA1 Antibodies to HtrA1

Figure 5:
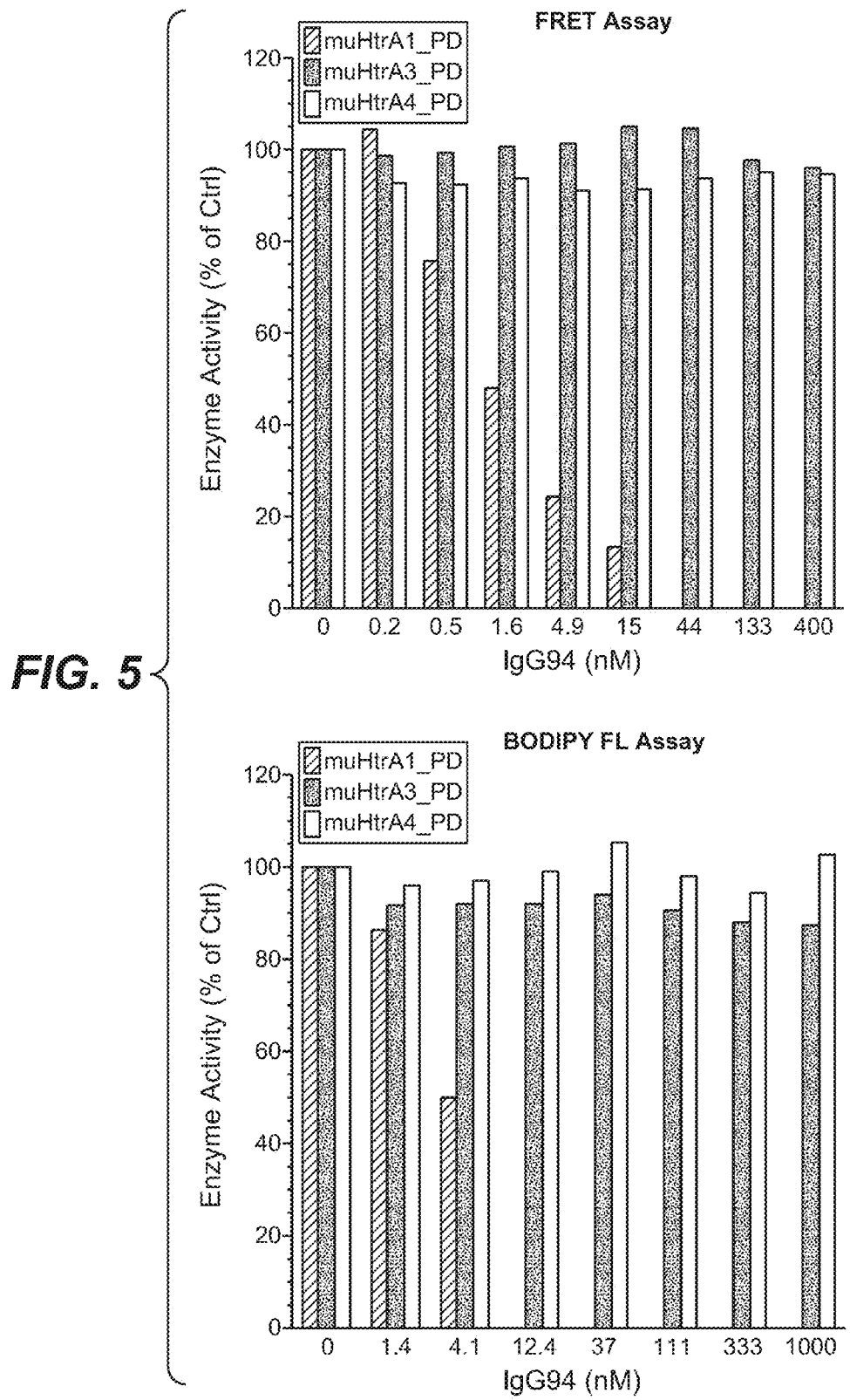
FIG. 5. Specificity of IgG94. MuHtrA1_PD, MuHtrA3_PD and MuHtrA4_PD were incubated with increasing concentrations of IgG94 and enzyme activities towards the peptide substrate H2-Opt (top panel) or casein BODIPY FL reagent (bottom panel) determined and expressed as percentage of uninhibited enzyme activities (% of control)

The specificity of IgG94 was assessed by measuring its activity for inhibiting muHtrA1_PD as compared to its ability to inhibit the structurally related proteases MuHtrA3_PD and MuHtrA4_PD (see FIG. 5). The specificity was determined using the FRET assay as described above in Example 3, except that the concentrations of MuHtrA1_PD, MuHtrA3_PD and MuHtrA4_PD 6 nM, 20 nM and 20 nM, respectively, and the concentration range of IgG94 was 0.2-400 nM. The specificity was also analyzed using the BODIPY FL casein substrate as described above in Example 4, except that the concentration of MuHtrA1_PD, MuHtrA3_PD and MuHtrA4_PD was 50 nM and the concentration range of IgG94 was 1.4-1000 nM. IgG94 inhibited MuHtrA1_PD cleavage of H2-Opt (FIG. 5, top panel) and BODIPY FL (FIG. 5, bottom panel), but did not inhibit cleavage of the same substrates by MuHtrA3_PD and MuHtrA4_PD up to concentrations of 400 nM and 1000 nM for H2-Opt and BODIPY FL substrates, respectively. The results suggest that IgG94 has excellent specificity and does not impair activities of related proteases.

Example 6: Determination of Antibody Affinity by BIAcore

To determine the binding affinity of Fab94 by single-cycle kinetics, Surface Plasmon Resonance (SRP) measurement with a BIAcore™ T100 instrument was used. Briefly, series S sensor chip CM5 was activated with EDC and NHS reagents according to the supplier's instructions, and streptavidin (Pierce) was coupled to achieve approximately 2000 response units (RU), followed by blocking unreacted groups with 1M ethanolamine.

For kinetics measurements, biotinylated HuHtrA1_PD or MuHtrA1_PD were first injected at 10 µl/min flow rate to capture approximately 100 RU at 3 different flow cells (FC), except for FC1 (reference cell), and then 5-fold serial dilutions of Fab94 (0.48 nM-300 nM) in 0.01M HEPES pH 7.4, 0.15M NaCl, 0.005% surfactant P20 were injected (flow rate: 300 µl/min) with no regeneration between injections. The sensorgrams were evaluated by BIAcore™ T100 Evaluation Software (version 2.0) after subtraction of reference cell signal. Association rates ($k_{on}$) and dissociation rates ($k_{off}$) were calculated using a simple one-to-one Langmuir binding model. The equilibrium dissociation constant ($K_D$) was calculated as the ratio $k_{off}/k_{on}$ (see Table 1 below). The binding kinetics of Fab94 to HuHtrA1_PD and to MuHtrA1_PD were very similar. The $K_D$ values were 31.1 nM and 28.9 nM, respectively.

TABLE 1

Binding Affinities of Fab94 to HuHtrA1_PD and MuHtrA1_PD by Surface Plasmon Resonance.

| | $k_{on}$ ($10^5$ M$^{-1}$s$^{-1}$) | $k_{off}$ ($10^4$ s$^{-1}$) | $K_D$ (nM) |
|---|---|---|---|
| HuHtrA1_PD | 3.5 | 109.0 | 31.1 |
| MuHtrA1_PD | 4.5 | 129.0 | 28.9 |

Example 7: Epitope Mapping of IgG94 on HuHtrA1_PD

To identify the functional binding epitope of IgG94, a panel of HuHtrA1_PD mutants with individual alanine mutations was generated for binding experiments. Most of the mutated residues are located on surface loops surrounding the active site and also included the catalytic serine (S328) and aspartate (D250). The mutants were expressed in E. coli and the trimers purified by size exclusion chromatography as described in Example 2. Binding was determined using an ELISA assay, which was conducted using a MAXISORP™ microtiter plate coated with HuHtrA1_PD mutants at 2 µg/ml in PBS for 1 h, followed by blocking with PBST buffer (0.5% BSA and 0.05% Tween 20 in PBS) for 1 h at room temperature. Five-fold serially diluted Ig94 (50 nM to 0.0006 nM) in PBST buffer was added and incubated for 30 min. The plates were washed with PBT buffer (0.05% Tween 20 in PBS), and HRP-conjugated goat anti-human IgG (H+L) (Invitrogen) was added (1:5000 in PBST buffer) and incubated for 1 h. The plates were washed with PBT buffer and developed by adding tetramethylbenzidine substrate (Kirkegaard and Perry Laboratories, Gaithersburg, Md.). The absorbance at 450 nm was plotted as a function of antibody concentration in solution to determine $EC_{50}$ values. The location of mutants effecting binding were then mapped onto the structure of HtrA1.

Figure 7B:
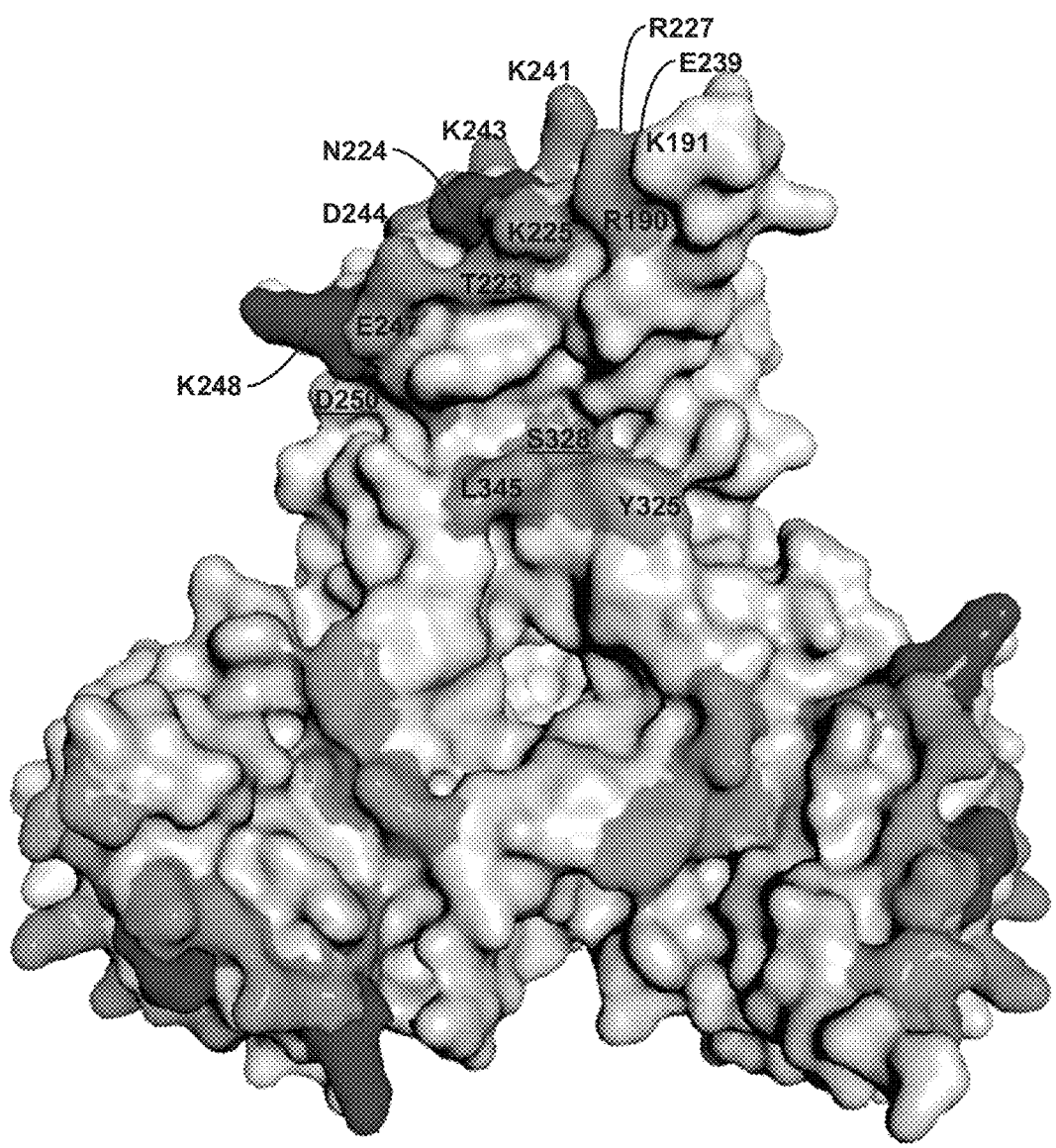
Figure 7C:
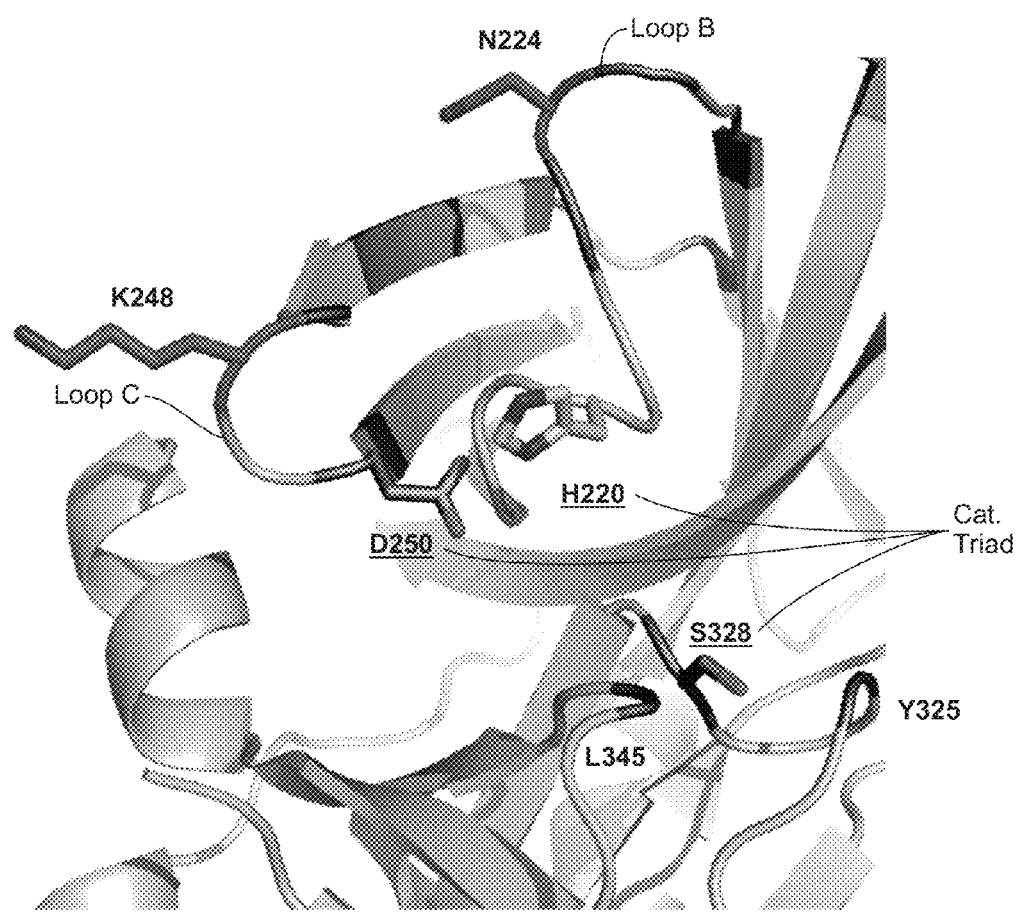
Figure 8A:
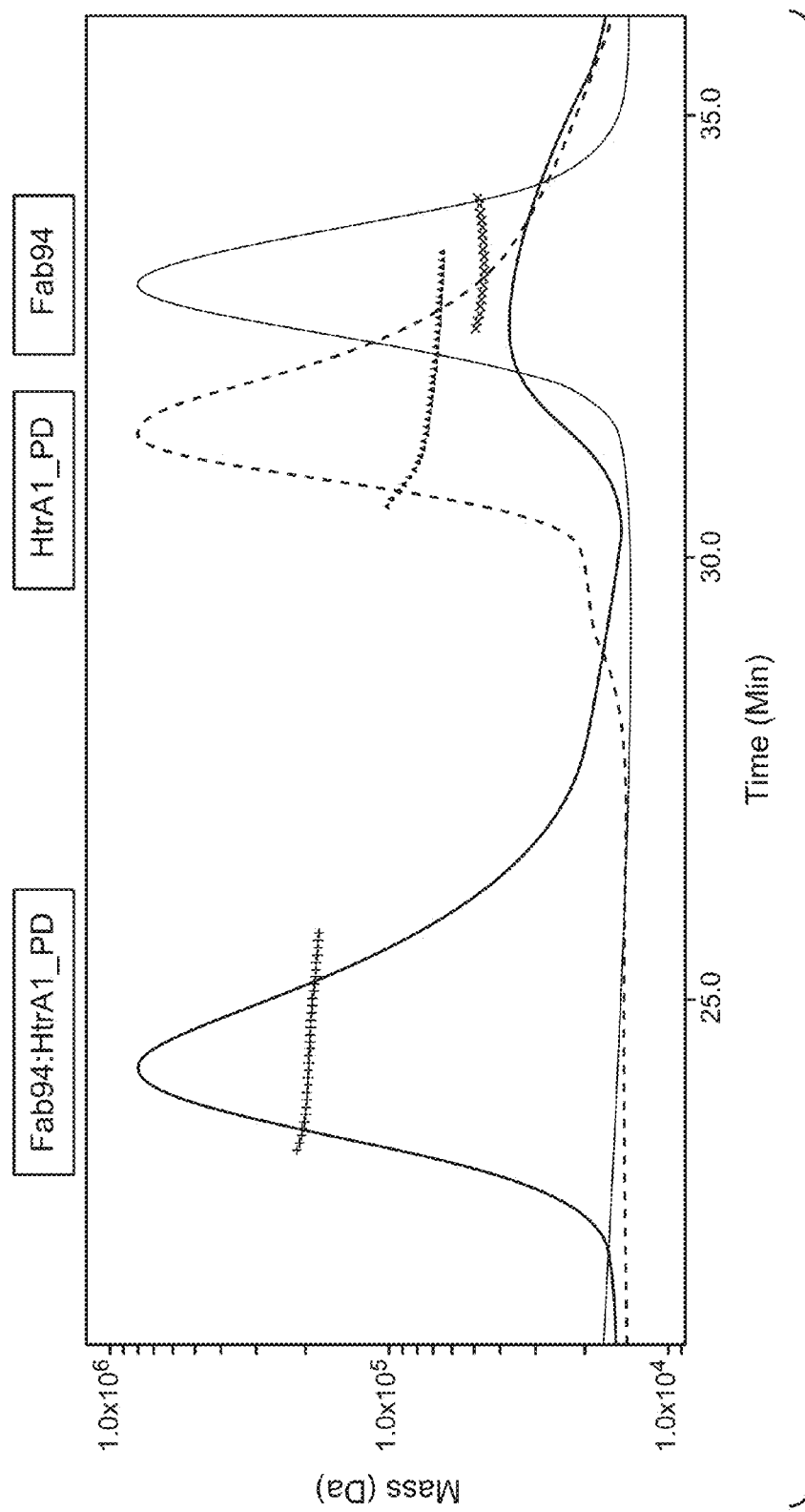
FIGS. 8A-B. SEC-MALLS (size exclusion chromatography-multi-angle laser light scattering) of the Fab94:HuHtrA1_PD(S328A) complex (FIG. 8A) and the IgG94:HuHtrA1_PD(S328A) complex (FIG. 8B). Shown are the elution peaks by SEC (x-axis) and the masses of individual proteins and complexes (y-axis; dotted lines across the elution peaks).
Figure 8B:
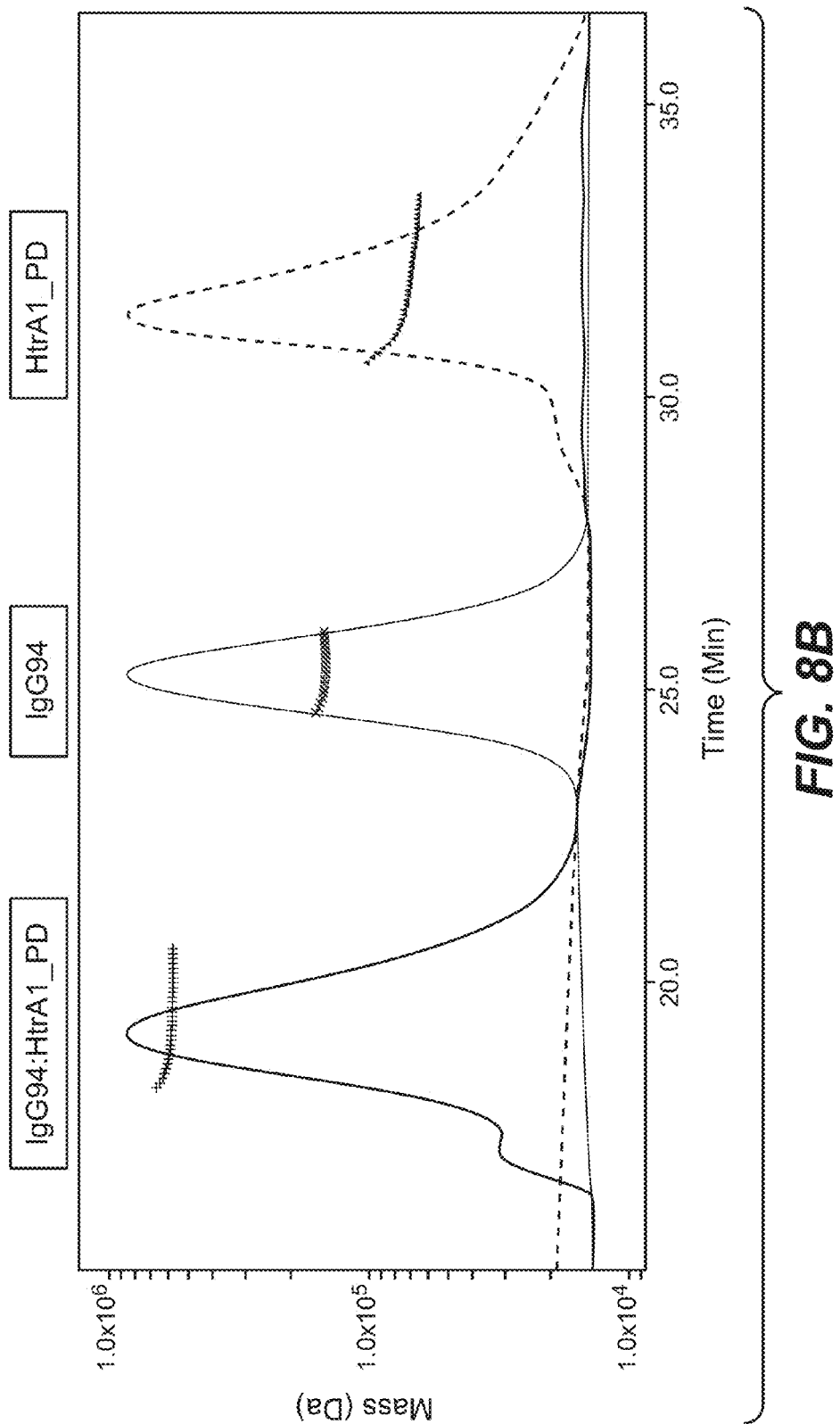

In the binding ELISA, IgG94 showed the greatest reduction in binding to the mutants HuHtrA1_PD(N224A) and HuHtrA1_PD(K248A) (see FIG. 7A). Upon repetition of the experiment using a lower concentration of HtrA1 to coat the plates (1 µg/ml) and a shortened incubation time (reduced from 1 hour to 20 minutes incubation), IgG94 also showed at least a 5-fold reduction in binding to HuHtrA1 mutants V201A, H220A, T223A, K225A, K243A and E247A (see FIG. 7A). The results indicate that IgG94 binds to an epitope that includes residues N224 and K248, which are located on Loop B and Loop C (see FIGS. 7B and 7C). In trypsin-like serine proteases these loops are known to be part of the specificity determining region that interacts with substrates. K248 (Loop C) is very close to the catalytic D250 and N224 to the catalytic H220. Therefore, binding of IgG94 to these residues may impair substrate access to the catalytic cleft either by direct steric hindrance or by an indirect allosteric mechanism as found for neutralizing anti-HGFA antibodies that also recognize residues in Loop C (Ganesan, R., et al., Structure 17:1614-1624 (2009); Wu, Y., et al., Proc Natl Acad Sci USA 104:19784-9 (2007)). Alternatively, antibody binding may inhibit catalysis by directly influencing the catalytic triad residues D250 and/or H220.

Example 8: Stoichiometry of Complexes of HtrA1_PD with Fab94 and IgG94 by Size Exclusion Chromatography-Multi-Angle Light Scattering (SEC-MALLS)

A catalytically inactive form HuHtrA1_PD(S328A) was used for complex formation. The Fab94:HuHtrA1_PD (S328A) and IgG94:HuHtrA1_PD(S328A) complexes were formed in Tris buffer (50 mM Tris-HCl, pH 8.0, 200 mM NaCl, 10% glycerol, 0.25% CHAPS). The complexes and the individual components alone were incubated at 4° C. overnight and then injected and resolved on a 5200 Superdex 10/300 GL column (GE Healthcare) in Tris buffer with a flow rate of 0.5 mL/min. Data was collected with an 18-angle light scatter detector (Dawn Helios II with QELS) and a refractive index detector (Optilab reX) from Wyatt Technologies. Analysis was done with Astra 5 software to yield molar mass independently of elution time. Normalization was performed with a control IgG.

SEC-MALLS experiments show that Fab94 and IgG94 form complexes with HuHtrA1_PD(S328A) that have distinct masses. The determined masses and deduced stoichiometry of the complexes are shown in Table 2.

TABLE 2

Stoichiometry of HuHtrA1_PD(S328A) in complex with Fab94 and IgG94 determined by SEC-MALLS.

| Components* | Mass by MALLS (Da)** | Best-fit stoichiometry<sup>&</sup> | Expected mass (Da) | Mass difference (%) |
|---|---|---|---|---|
| HtrA1_PD | 76,755 | — | — | — |
| Fab94 | 47,400 | — | — | — |
| IgG94 | 151,200 | — | — | — |
| Fab94:HtrA1_PD | 210,100 | 3:1 | 218,955 | 4.2 |
| IgG94:HtrA1_PD | 618,600 | 3:2 | 607,110 | 1.9 |

*HuHtrA1_PD was HuHtrA1_PD with the catalytic serine mutated to alanine (HuHtrA1_PD(S328A)); the mass represents the trimer
**Average of two independent experiments
<sup>&</sup>Ratio of antibody:protease trimer The determined mass of the Fab94:HtrA1_PD(S328A) complex of 210, 100 Da is consistent with a complex of 3 Fabs binding to one HuHtrA1_PD(S328A) trimer (3:1 complex). The difference between the experimental and the theoretical masses of such a 3:1 complex is only 4.2%. Therefore, one Fab is able to bind to each HuHtrA1_PD (S328A) monomer within one HtrA1 homo-trimer.

The determined mass of the IgG94:HtrA1_PD(S328A) complex of 618, 600 Da fits well to a 3:2 stoichiometry, in that 3 IgG molecules bind to two HuHtrA1_PD(S328A) trimers. The difference between the experimental and the theoretical mass of such a 3:2 complex is only 1.9%.

The elucidated stoichiometries are in agreement with the findings that Fab94 and IgG94 are able to completely inhibit HtrA1 activity, in that each monomer within an HtrA1 trimer is binding to one Fab or to one Fab arm of an IgG. Thus, in these complexes there is no 'free' HtrA1 monomer available, in agreement with the complete inhibition of HtrA1 enzyme activity by Fab94 and IgG94. We propose a 'cage' model for the IgG94:HtrA1_PD(S328A) complex in which the Fab arms of the 3 IgGs are bridging two trimers, each Fab arm binding to one monomer (see FIG. 9). The model also accounts for the about 16-fold increased potency of IgG94 over Fab94 in enzymatic assays (see e.g., FIG. 3) in that IgG94, strongly benefits from avidity effects in its binding to HtrA1_PD trimers.

Example 9: Affinity Maturation of YW505.94

Construct Libraries for Anti-HtrA1 Affinity Maturation.

Clone YW505.94a was derived from YW505.94 [Ab94] by changing Kabat residue N28 to serine within CDR H1 in order to remove a potential N-linked glycosylation site. Phagemid pWO703, derived from phagemid pV0350-2b (Lee et al., *J. Mol. Biol.* 340, 1073-1093 (2004)), which contains a stop codon (TAA) in all CDR-L3 positions and displays monovalent Fab on the surface of M13 bacteriophage, served as a library template for grafting the heavy chain variable domain ($V_H$) of clone YW505.94a for affinity maturation. Both hard and soft randomization strategies were used for affinity maturation. For hard randomization, one light chain library (L1/L2/L3hard) with selected positions at three light chain CDRs was randomized using amino acids designed to mimic a natural human antibody and the designed DNA degeneracy was as described (Lee et al., 2004). For soft randomization, selected residues at Kabat positions 91, 92, 93, 94 and 96 of CDR-L3, 28-35 of CDR-H1, 50-58 of CDR-H2, and 95-100 of CDR-H3 with two different combinations of CDR loops, L3/H1soft, L3/H2soft and L3/H3soft, were targeted for randomization. To achieve the soft randomization conditions, which introduce a mutation rate of approximately 50% at the selected positions, the mutagenic DNA was synthesized with 70-10-10-10 mixtures of bases favoring the wild type nucleotides (Gallop et al., *J. of Med. Chem.* 37, 1233-1251 (1994)).

Phage Sorting Strategy to Isolate Affinity-Improved Variants.

For affinity improvement selection, phage libraries were subjected to plate sorting for the first round, followed by four rounds of solution sorting. For the first round of plate sorting, four libraries (L1/L2/L3hard, L3/H1soft, L3/H2soft and L3/H3soft) were sorted against a human HtrA1 (HuHtrA1) coated plate (NUNC Maxisorp plate) separately with phage input at about 3 O.D./ml in 1% BSA and 0.05% Tween 20 for 1 hour at room temperature (RT). After the first round of plate sorting, four rounds of solution sorting were performed to increase the stringency of selection. For solution sorting, 1 O.D./ml of phage propagated from first round of plate sorting were incubated with 500 nM of biotinylated HuHtrA1 in 100 ul buffer containing 1% Superblock (Pierce biotechnology) and 0.05% Tween20 for at least 1 hour at room termperature (RT). The mixture was further diluted 10× with 1% Superblock and applied 100 ul/well to neutravidin-coated wells (10 ug/ml) for 15 min at RT with gentle shaking so that biotinylated HuHtrA1 could bind phage. The wells were washed with PBS-0.05% Tween20 ten times. To determine background binding, control wells containing phage without biotinylated HuHtrA1 selection were captured on neutravidin-coated plates. Bound phage was eluted with 0.1N HCl for 20 min, neutralized by 1/10 volume of 1M Tris pH11, titered, and propagated for the next round. Next, three more rounds of solution sorting were carried out using two methods of increasing selection stringency simultaneously. The first method, which is for on-rate selection, decreases biotinylated target protein concentration from 10 nM to 0.1 nM. The second method, which is for off-rate selection, adds excess amounts of non-biotinylated HuHtrA1 protein (100~1000 fold more) to compete off weaker binders. Also, the phage input was decreased (0.1~0.5 O.D/ml) to lower the background phage binding.

High Throughput Affinity Screening ELISA (Single Spot Competition).

Colonies were picked from the fifth round screening and grown overnight at 37° C. in 350 ul/well of 2YT media with 50 ug/ml carbenicillin and 1e 10/ml KO7 in 96-well block (QIAgene). From the same plate, a colony of XL-1 infected parental phage was picked as a control. 96-well Nunc Maxisorp plates were coated with 100 ul/well of HuHtrA1 protein (2 ug/ml) in PBS at RT for 2 hours. The plates were blocked with 100 ul of 0.5% BSA and 0.05% Tween in PBS (PBST buffer) for one hour.

The phage supernatant was diluted 1:5 in PBST buffer with or without 5 nM HuHtrA1 in 100 ul total volume and incubated at least 1 hour at RT. Then, 75 ul of mixture were transferred to the HuHtrA1 coated plates. The plate was gently shacken for 15 min to allow the capture of unbound phage to the HuHtrA1 coated plate. The plate was washed five times with 0.05% Tween20 in PBS (PBT buffer). The binding was quantified by adding horse radish peroxidase (HRP)-conjugated anti-M13 antibody in ELISA buffer (1:5000) and incubated for 30 min at RT. The plates were washed with PBT buffer five times. Next, 100 ul/well of a 1:1 ratio of 3,3',5,5'-tetramethylbenzidine (TMB) Peroxidase substrate and Peroxidase Solution B ($H_2O_2$) (Kirkegaard-Perry Laboratories (Gaithersburg, Md.)) was added to the well and incubated for 5 minutes at RT. The reaction was stopped by adding 100 ul 1M Phosphoric Acid ($H_3PO_4$) to each well and allowed to incubate for 5 minutes at RT. The OD of each well was determined using a standard ELISA plate reader at 450 nm. The OD reduction (%) was calculated by the following equation:

$$OD_{450nm} \text{ reduction (\%)} = [(OD_{450nm} \text{ of wells with competitor})/(OD_{450nm} \text{ of well with no competitor})]*100$$

In comparison to the $OD_{450nm}$ reduction (%) of the well of parental phage (100%), clones that had the $OD_{450nm}$ reduction (%) lower than 50% were picked for sequence analysis (see FIGS. 15 and 16). Unique clones were selected for phage preparation to determine binding affinity (phage $IC_{50}$) by phage competition ELISA (see FIGS. 17 and 18). Then, the most affinity-improved clones (YW505.94a.28 & YW505.94a.54) were reformatted into human IgG1 for antibody production and further BIAcore binding kinetic analysis.

Phage Competition ELISA to Determine $IC_{50}$.

Figure 17:
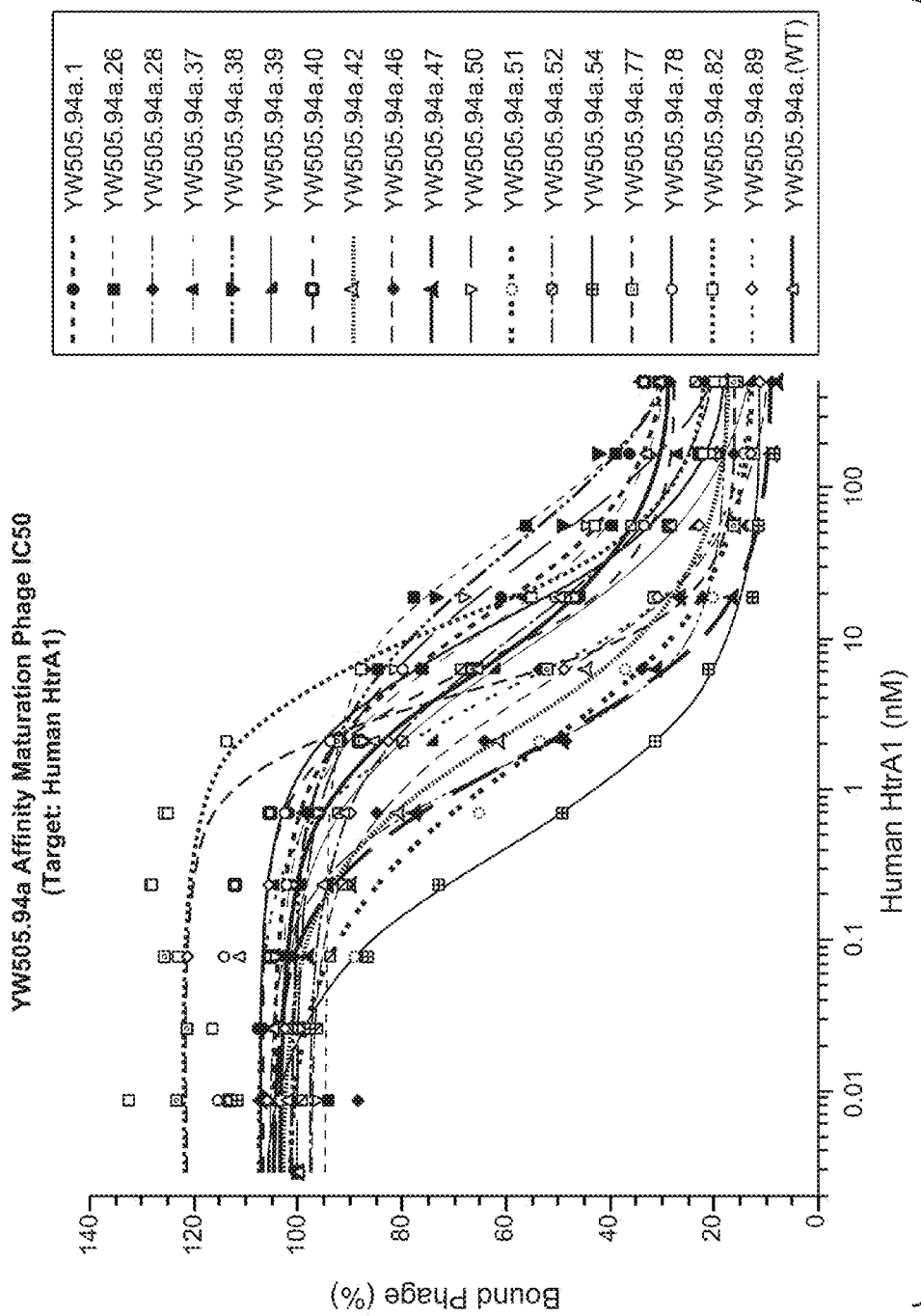
FIG. 17. Results of a phage competition assay demonstrating the binding of YW505.94a affinity-improved variants against HuHtrA1.
Figure 18:
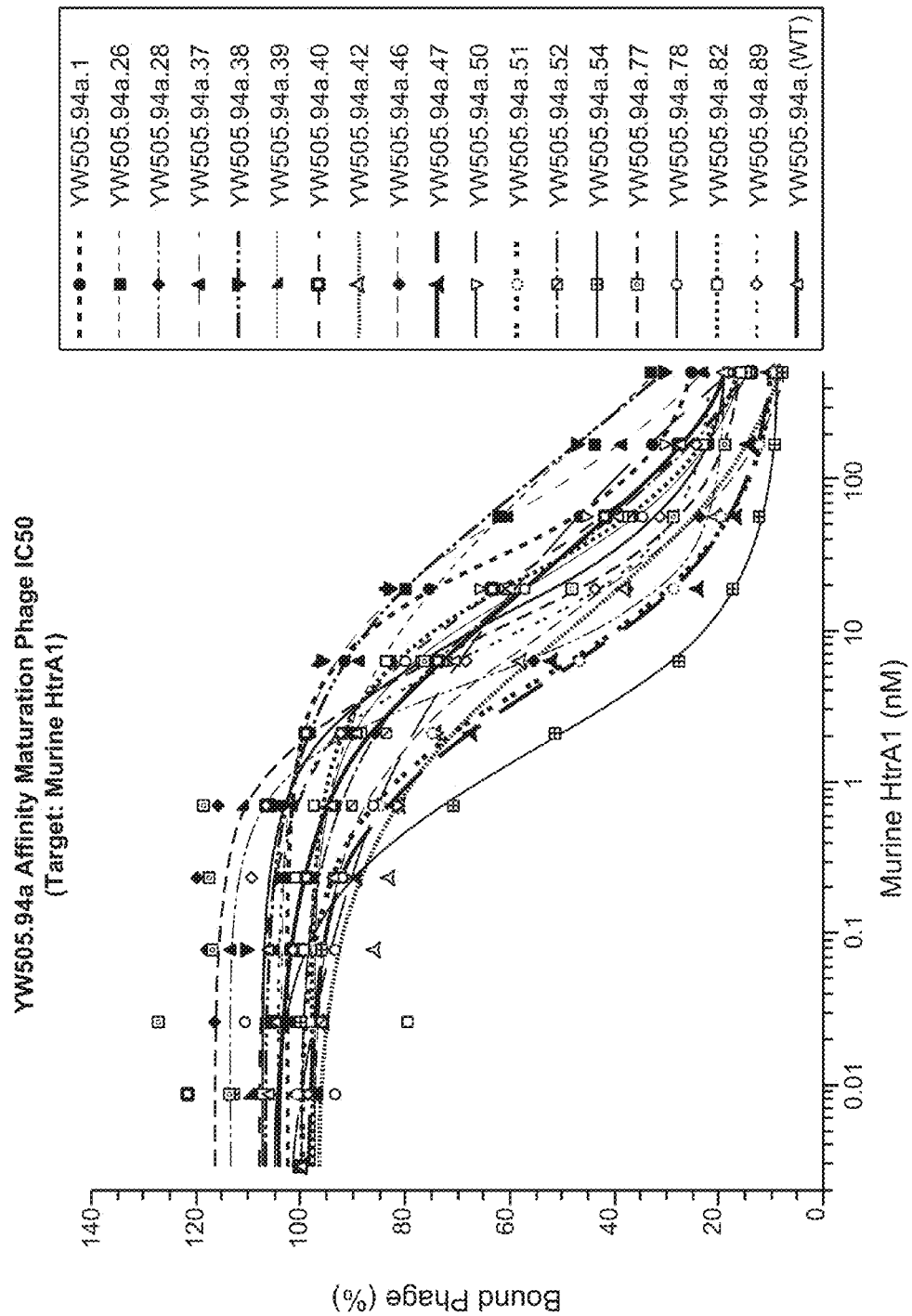
FIG. 18. Results of a phage competition assay demonstrating the binding of YW505.94a affinity-improved variants against MuHtrA1.

MAXISORP™ microtiter plates were coated with HuHtrA1 at 2 µg/ml in PBS for 2 hr at RT and then blocked with PBST buffer for another hour at RT. Purified phage from culture supernatants were incubated with serially diluted HuHtrA1 or MuHtrA1 in PBST buffer in a tissue-culture microtiter plate for an hour, after which 80 µl of the mixture was transferred to the HuHtrA1-coated wells for 15 minutes to capture unbound phage. The plate was washed with PBT buffer, and HRP-conjugated anti-M13 (Amersham Pharmacia Biotech) was added (1:5000 in PBST buffer) for one hour. The plate was washed with PBT buffer and developed by adding tetramethylbenzidine substrate (Kirkegaard and Perry Laboratories, Gaithersburg, Md.). The absorbance at 450 nm was plotted as a function of HuHtrA1 or MuHtrA1 concentration in solution to determine phage $IC_{50}$. This was used as an affinity estimate for the Fab clone displayed on the surface of the phage. FIG. 17 shows results from a phage competition assay demonstrating the binding of YW505.94a affinity-improved variants against HuHtrA1. FIG. 18 shows results from a phage competition assay demonstrating the binding of YW505.94a affinity-improved variants against MuHtrA1.

Antibody Affinity Determinations by BIAcore.

To determine the binding affinity of HtrA1 antibodies by single cycle kinetics, Surface Plasmon Resonance (SRP) measurement with a BIAcore™ T100 instrument was used. Briefly, a series S sensor chip CM5 was activated with EDC and NHS reagents according to the supplier's instructions, and streptavidin (Pierce) was coupled to achieve approximately 2000 response units (RU), followed by blocking un-reacted groups with 1M ethanolamine.

For kinetics measurements, biotinylated human or murine HtrA1 was first injected at 10 ul/min flow rate to capture approximately 100 RU at 3 different flow cells (FC), except for FC1 (reference), and then 5-fold serial dilutions of anti-HtrA1 Fab in HBS-P buffer (0.01M HEPES pH 7.4, 0.15M NaCl, 0.005% surfactant P20) from low (0.48 nM) to high (300 nM) [5 points] were injected (flow rate: 300 min) one after the other in the same cycle with no regeneration between injections. The sensorgram was recorded and subject to reference and buffer subtraction before evaluation by BIAcore™ T100 Evaluation Software (version 2.0). Association rates ($k_{on}$) and dissociation rates ($k_{off}$) were calculated using a simple one-to-one Langmuir binding model. The equilibrium dissociation constant (Kd) was calculated as the ratio $k_{off}/k_{on}$. The results are shown in Table 3 below.

TABLE 3

Binding Affinities of Affinity Matured Fabs as Compared to the Parent Fab.

| | HuHtrA1 | | | MuHtrA1 | | |
|---|---|---|---|---|---|---|
| Fab | $k_{on}$ $(M^{-1}s^{-1})$ | $k_{off}$ $(s^{-1})$ | $K_D$ (nM) | $k_{on}$ $(M^{-1}s^{-1})$ | $k_{off}$ $(s^{-1})$ | $K_D$ (nM) |
| YW505.94 | 3.51e5 | 109e-4 | 31.1 | 4.47e5 | 129e-4 | 28.9 |
| YW505.94a | 8.13e5 | 4.48e-2 | 55 | 1.48e6 | 8.56e-2 | 58 |
| YW505.94a.28 | 1.69e6 | 5.74e-3 | 3.4 | 2.02e6 | 9.3e-3 | 4.6 |
| YW505.94a.54 | 2.97e6 | 7.84e-3 | 2.6 | 2.82e6 | 4.55e-3 | 1.6 |

Example 10: Sparing of Photoreceptors, Outer Nuclear Layer (ONL), and Functional Responses in the Absence of HtrA1 Following Constant Light Exposure Construction of HtrA1 Knockout Mouse.

To generate HtrA1 (+/−) embryonic stem cells, linearized targeting vector DNA was electroporated into ES cells of Balb/c background to introduce Flox sites in the region 5' of exon 1 and 3' of exon 1 and an introduced neomycin-resistance gene (Neo). ES clones resistant to neomycin were selected, and exon 1 plus the neomycin cassette was excised by electroporating the ES cells with a cre-recombinase-expressing expression plasmid. Homologous recombination was confirmed by sequencing of the entire HtrA1 locus and upstream promoter region in the targeted ES cell. Targeted clones were injected into C57BL/6 blastocysts to generate male chimeric mice of germline transmission. Interbreeding of +/−female and +/−male mice was performed to generate −/−female or −/−male HtrA1 mice on a Balb/c background. Successful deletion of HtrA1 was confirmed by RT-PCR of ovaries from HtrA1 wt and ko mice.

Constant Light Exposure Model.

Male Balb/c Htra1 wt/wt or ko/ko mice, 8-13 weeks old, are in normal housing (<100 lux in cage) until start of constant light exposure (CLE). To start CLE, mice are housed singly in normal cages covered with a wire rack only, without a filter top. Food pellets and Hydrogels are placed on the bottom of the cage, and not on the wire top, for nourishment so as to not impede light entering the cage. Ten cages are placed on a Metro rack outfitted with fluorescent lights and enclosed in white panels to deliver ~1200 lux to mice for up to 14 days. Cages are rotated counterclockwise around the rack daily during CLE to ensure equal light exposure. If multiple shelves are used, cages are also rotated between shelves to ensure equal light exposure.

Optical Coherence Tomography.

Optical coherence tomography (OCT) is performed 4-7 days before light exposure to provide a retinal thickness baseline measurement. OCT is performed using a Heidelberg Spectralis HRA+OCT camera. Animals are anesthetized with 70-80 mg/kg ketamine/15 mg/kg xylazine in 150-300 ul sterile saline, eyes are dilated with 1% tropicamide drops and retina thickness is measured by OCT. Artificial tears are used to keep eyes moist to prevent cataracts. After OCT, animals are allowed to recover from anesthesia and returned to their cages and light rack.

Electroretinogram.

Electroretinograms (ERG) ERGs are performed 7 days before light exposure and at 15 days post CLE. ERGs are performed and recorded using a Diagnosys LLC Espion 2 visual electrophysiology system and a Colordome desktop Ganzfeld as a light source. Mice are dark adapted overnight in a dark room to equilibrate photoreceptors. Once dark adapted, all subsequent procedures are performed in the dark with only a red light for illumination. Animals are anesthetized with Ketamine, 75-80 mg/kg, & Xylazine, 7.5-15 mg/kg, IP in 200-300 ul PBS. Mouse body temperature is maintained at 37° C. using a homeothermic plate connected to its control unit. Pupils are dilated with 1% tropicamide. ERGs from both eyes will be recorded simultaneously with Burian-Allen silver or platinum wire loop electrodes. Mice are placed on a platform, a reference electrode is inserted subcutaneously through the forehead, and a ground electrode is inserted subcutaneously at the base of the tail. Gonak hypermellose solution is placed on the cornea to establish an electrical contact between the cornea and the electrode, and protect eyes from drying during the experiment. Electrodes are placed on the left and right eyes and mouse inserted into a ColorDome light stimulator. Eyes will be stimulated with white light (7 flash intensities 4e-5, 2e-5, 0.5, 2, 5, 10, 20 cd.s/m$^2$) and signals bandpass-filtered at 0.15-1000 Hz and sampled at 2 kHz.

Determination of HtrA mRNA Levels in the Mouse Retina and Ovary.

Whole eyes were enucleated, the retina removed and placed in RLT Buffer (Qiagen) and frozen at −80° C. until homoginization. Retina's were homogenized and shredded by gentleMACS M tubes (Miltinyi Biotec). Similar to the retina, ovarys were isolated from female HtrA1 wt, het and ko mice and homogenized as described for the retina. RNA was isolated using Qiagen Plus RNeasy kit; cDNA was generated with High Capacity cDNA kit (Applied Biosystem); Taqman qPCR was performed using 20 ug cDNA, Taqman Gene Expression Master Mix (Applied Biosystem) and Taqman Gene Expression Assay primers (Applied Biosystem) to exon 1-2 (retina and ovary), exon 3-4 (ovary) and exon 5-6 (ovary) and ran on an ABI 7500 Real-time PCR System (Applied Biosystem). HtrA expression was normalized to 18s expression (primer from Applied Biosystem).

Figure 11:
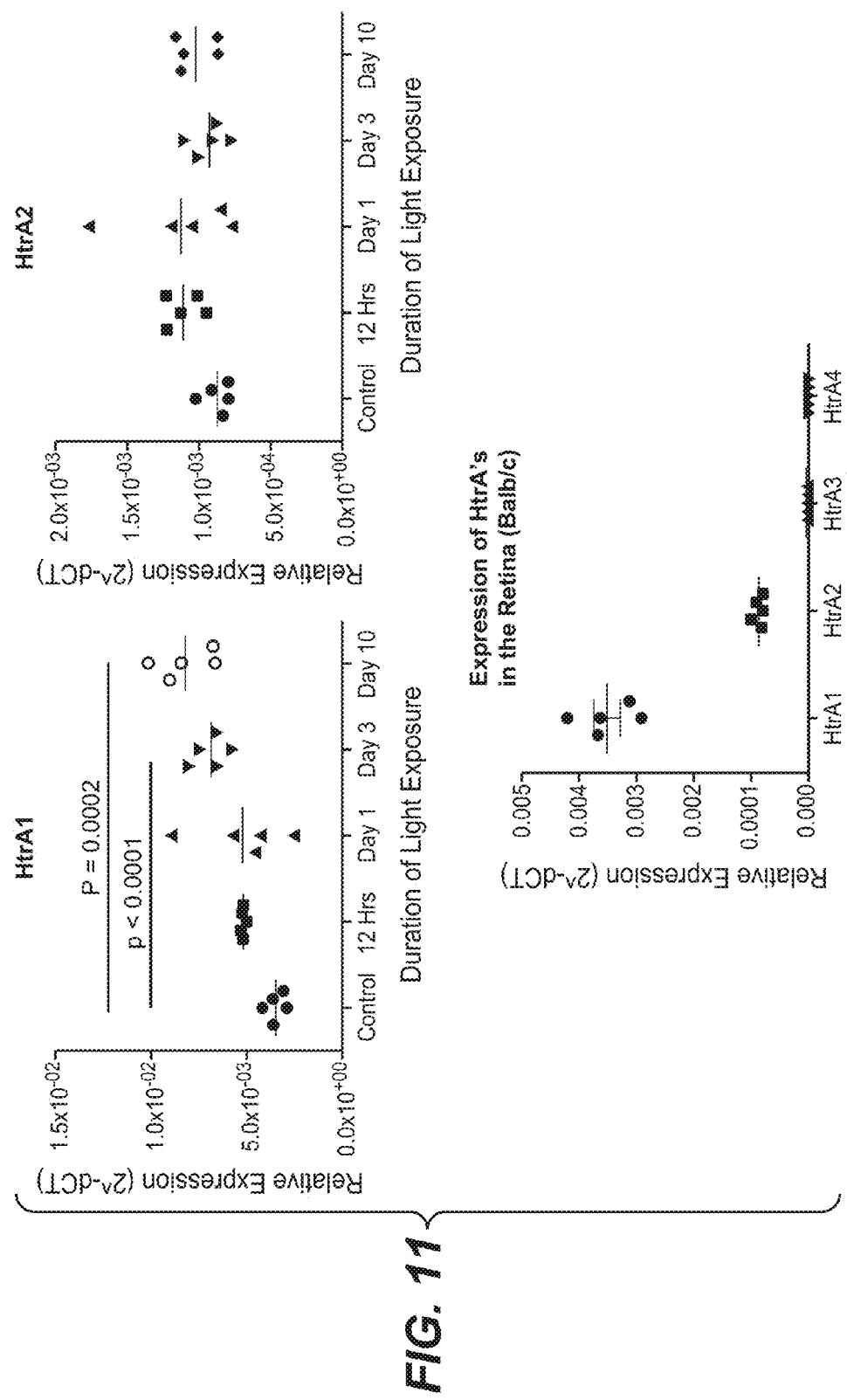
FIG. 11. HtrA1 mRNA expression increases in the retina in a mouse model of constant light exposure (top left panel). HtrA2 levels do not vary significantly in the same model (top right panel). HtrA1 expression is significantly higher than HtrA2, HtrA3 and HtrA4 expression levels in the mouse retina at baseline (bottom panel).

As shown in FIG. 11, HtrA1 mRNA expression increases in a mouse model of constant light exposure. However, in the same model, HtrA2 levels do not increase in the retina. In addition, HtrA1 levels are are significantly higher than HtrA2, HtrA3 and HtrA4 levels in the retina of a non-exposed mouse.

Figure 12:
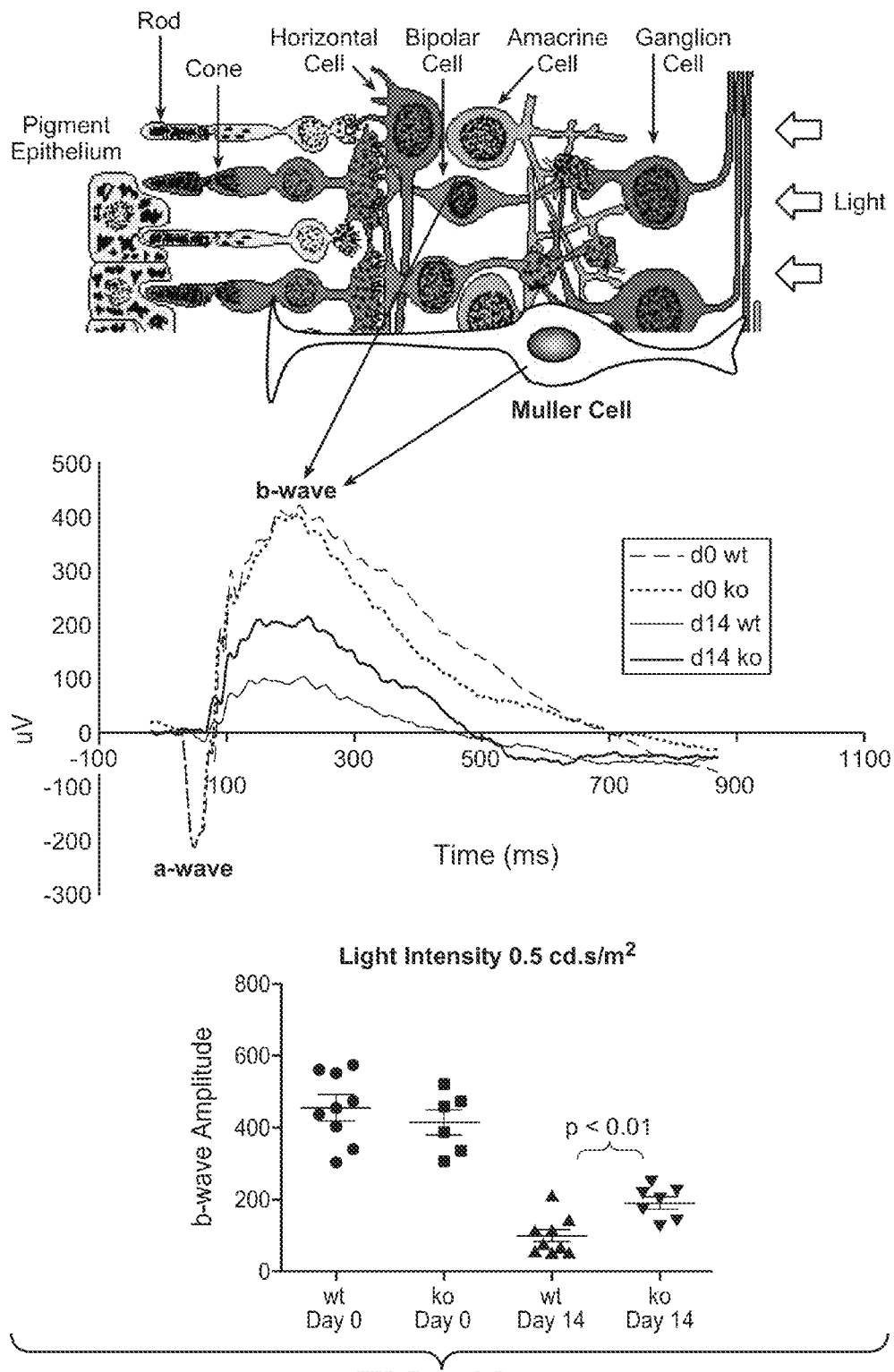
FIG. 12. Increased bi-polar cell/Muller cell responses in the absence of HtrA1 expression in a mouse model of constant light exposure.
Figure 13:
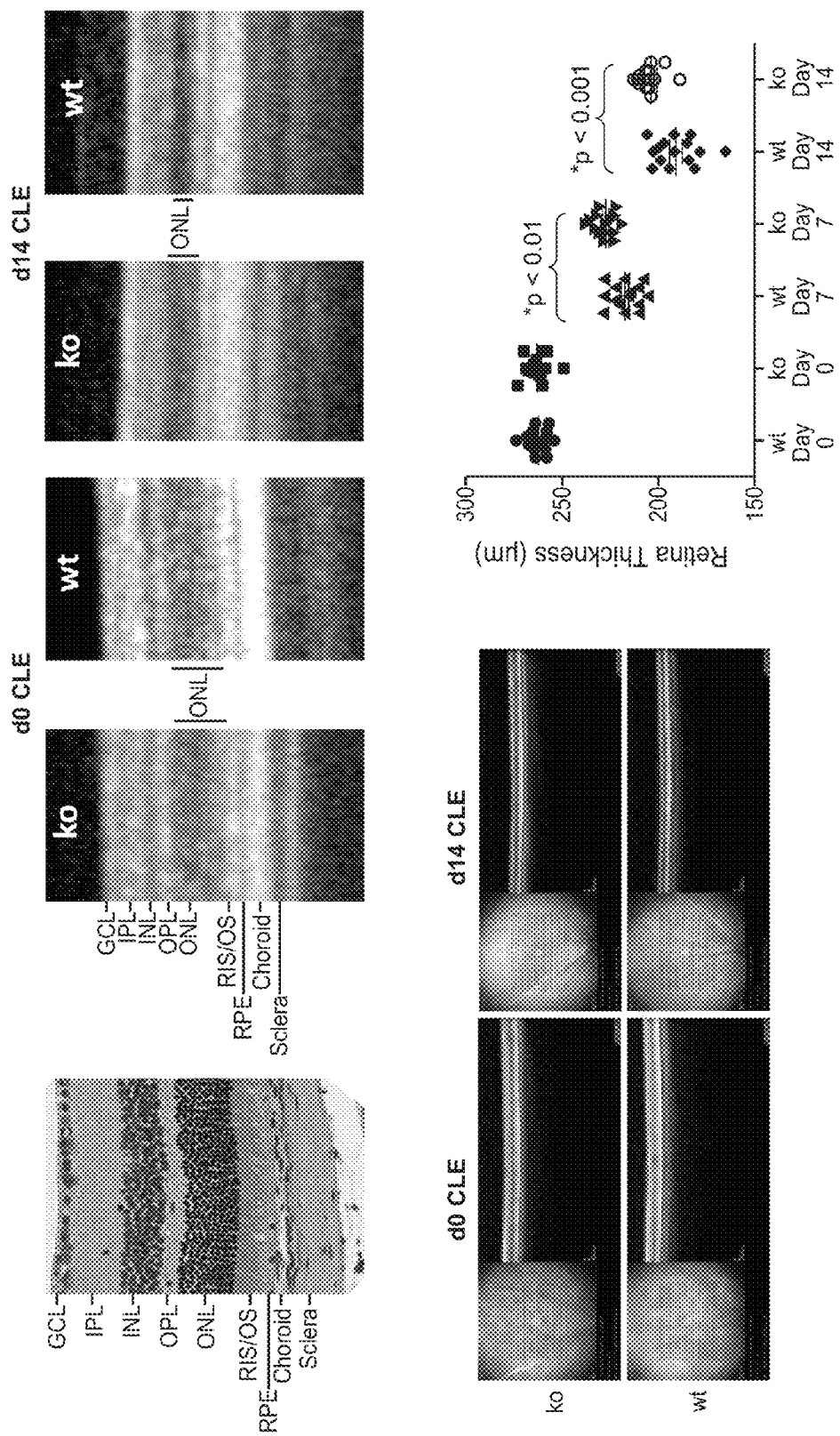
FIG. 13. Sparing of retina in the absence of HtrA1 expression in a mouse model of constant light exposure.
Figure 14:
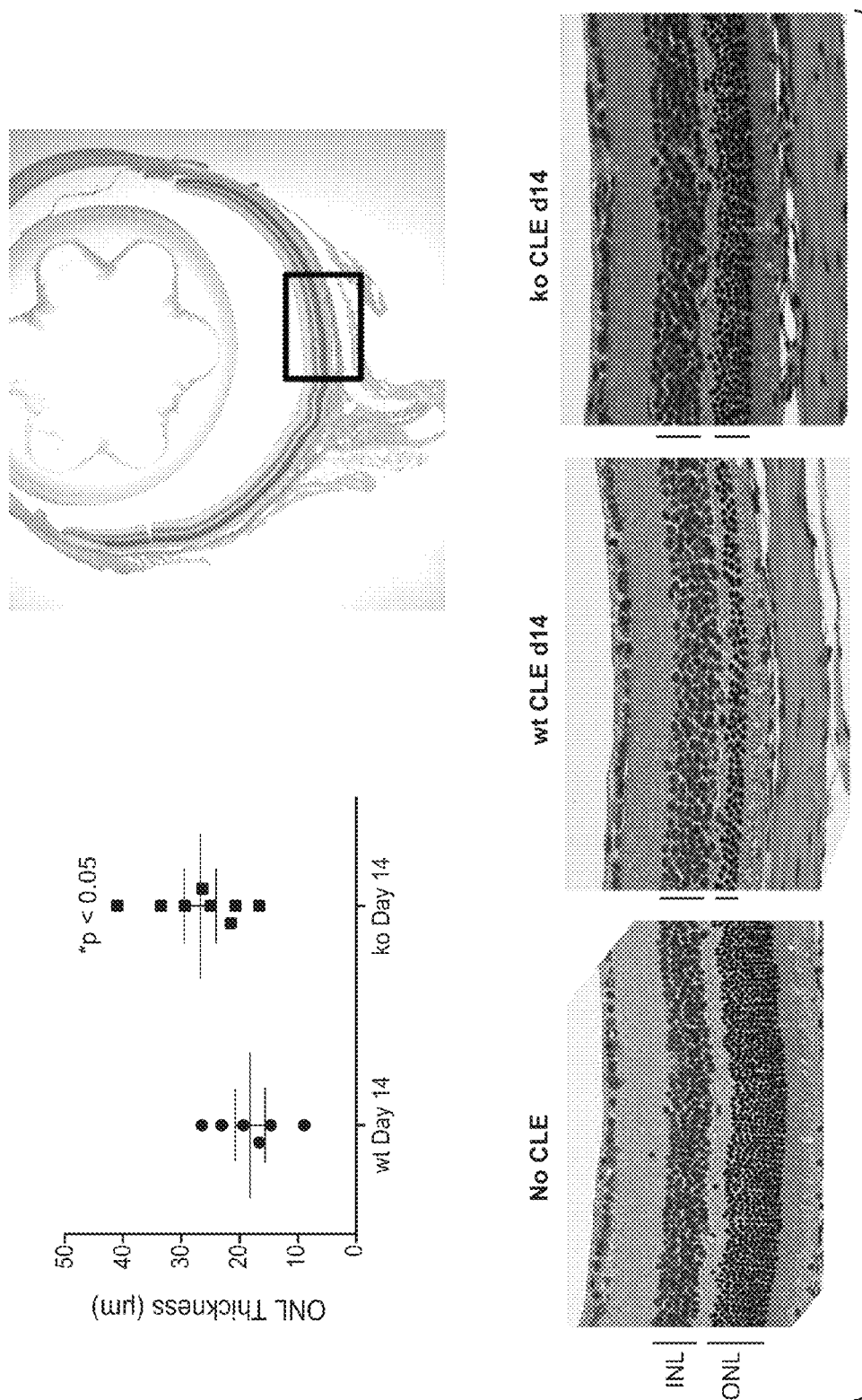
FIG. 14. Sparing of outer nuclear layer (ONL) photoreceptor cells in the absence of HtrA1 expression in a mouse model of constant light exposure.

In addition, we found that mice lacking HtrA1 expression show a sparing of photoreceptors (FIG. 13), the outer nuclear layer (ONL) (FIG. 14), and functional responses (ERG) (FIG. 12) in a mouse model of light-induced degeneration.

Example 11: Effects of an Anti-HtrA1 Antibody in a Rat Model of Constant Light Exposure Rats will be subjected to constant light exposure as described above for mice. The efficacy of an anti-HtrA1 antibody to protect the rat eye from degeneration caused by the light exposure will be evaluated. Rat eyes will be subject to intravitreal injections of an anti-HtrA1 antibody at a dose and frequency suitable to maintain an effective concentration of the anti-HtrA1 antibody in the eye during the course of the experiment. The rat eyes will be monitored following light exposure to determine retinal thickness by OCT and functionality by ERG, as described above for the mouse model.

Example 12: HtrA1 Expression is Abundant in Rat Vitreous and Accumulates in Mouse Eye Fluid and Eye Tissue Upon Light Stress ELISA Assay.

For analysis of rat tissues, an anti-muHtrA1 rabbit polyclonal antibody (Genentech) was diluted to 125 ng/mL, while for analysis of mouse eye fluid and retina tissue, an anti-huHtrA1 mouse monoclonal antibody (Genentech) was diluted to 250 ng/mL, both in PBS, and coated onto 384-well ELISA plates (Nunc; Neptune, N.J.) during an overnight incubation at 4° C. Plates were washed with PBS plus 0.05% Tween-20 and blocked during a two hour incubation with PBS plus 0.5% bovine serum albumin (BSA). This and all subsequent incubations were performed at room temperature with gentle agitation. Recombinant murine HtrA1 standard (Genentech) and samples from rat or murine tissues were diluted in sample/standard dilution buffer (PBS, 0.5% BSA, 15 ppm Proclin, 0.05% Tween 20, 0.25% CHAPS, 0.2% BgG, 5 mM EDTA, 0.35M NaCl, (pH 7.4)), added to washed plates, and incubated for 1.5-2 hours. Plate-bound HtrA1 was detected during a 1-hour incubation with a biotinylated anti-muHtrA1 rabbit polyclonal antibody (Genentech) diluted to 100 ng/mL for rat tissues, and for mouse eye fluid and retina tissue, biotinylated anti-huHtrA1 mouse monoclonal antibody (Genentech) was diluted to 200 ng/mL, both in assay buffer (PBS, 0.5% BSA, 15 ppm Proclin, 0.05% Tween 20), followed by a wash step and a 30-minute incubation with streptavidin-HRP (GE Healthcare; Piscataway, N.J.), also diluted in assay buffer (1:20, 000). After a final wash, tetramethyl benzidine (KPL, Gaithersburg, Md.) was added, color was developed for 10-15 minutes, and the reaction was stopped with 1 M phosphoric acid. The plates were read at 450 nm with a 620 nm reference using a microplate reader. The concentrations of rat or murine HtrA1 were calculated from a four-parameter fit of the muHtrA1 standard curve.

As shown in FIG. 19A, expression of HtrA1 was low in rat ovary, brain, spleen, and total eye tissue as compared to the levels of expression of HtrA1 in rat vitreous. As shown in FIG. 19B, the level of HtrA1 in mouse eye fluid increased in a model of constant light exposure as compared to a control. As shown in FIG. 19C, the level of HtrA1 in mouse retinal tissue increased in a model of contant light exposure as compared to a control.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

SEQUENCE LISTING

<160> NUMBER OF SEQ ID NOS: 90

<210> SEQ ID NO 1
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 1

Arg Ala Ser Gln Asp Val Ser Thr Ala Val Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Ala Ser Phe Leu Tyr Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln Ser Tyr Thr Thr Pro Pro Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Asn Ile Ser Gly Tyr Tyr Ile His
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Ile Asp Pro Tyr Gly Gly Asp Thr Asn Tyr Ala Asp Ser Val Lys
1               5                   10                  15

Gly

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Thr Phe Leu Thr Ser Trp Gly His Tyr Phe Asp Tyr
```

<210> SEQ ID NO 7
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Ser Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Thr Thr Pro Pro
                85                  90                  95
Thr Phe Gly Gln Gly Thr Lys Val Glu Ile Lys Arg
            100                 105

<210> SEQ ID NO 8
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Ser Gly Tyr
            20                  25                  30
Tyr Ile His Trp Val Arg Gln Ala Pro Gly Lys Gly Leu Glu Trp Val
        35                  40                  45
Gly Trp Ile Asp Pro Tyr Gly Gly Asp Thr Asn Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Gly Thr Phe Leu Thr Ser Trp Gly His Tyr Phe Asp Tyr Trp
            100                 105                 110
Gly Gln Gly Thr
        115

<210> SEQ ID NO 9
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
            35                  40                  45

Tyr Ala Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Trp
                85                  90                  95

Thr Phe Gly Gln Gly Thr Lys Val Glu Ile Lys Arg
            100                 105
```

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Val Ile Ser Gly Asp Gly Gly Ser Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Phe Asp Tyr Trp Gly Gln Gly Thr
            100                 105
```

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Met Lys His Gln His Gln His Gln His Gln His Gln His Met His
1               5                   10                  15

Gln Ser Thr Ala Ala
            20
```

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: N-term Mca
<220> FEATURE:
<221> NAME/KEY: MOD_RES
<222> LOCATION: (9)..(9)
<223> OTHER INFORMATION: Lys(DNP)

<400> SEQUENCE: 12

Ile Arg Arg Val Ser Tyr Ser Phe Lys Lys
1               5                   10

<210> SEQ ID NO 13
<211> LENGTH: 480
<212> TYPE: PRT
<213> ORGANISM: Homo sapiens

<400> SEQUENCE: 13

Met Gln Ile Pro Arg Ala Ala Leu Leu Pro Leu Leu Leu Leu Leu Leu
1               5                   10                  15

Ala Ala Pro Ala Ser Ala Gln Leu Ser Arg Ala Gly Arg Ser Ala Pro
            20                  25                  30

Leu Ala Ala Gly Cys Pro Asp Arg Cys Glu Pro Ala Arg Cys Pro Pro
        35                  40                  45

Gln Pro Glu His Cys Glu Gly Gly Arg Ala Arg Asp Ala Cys Gly Cys
    50                  55                  60

Cys Glu Val Cys Gly Ala Pro Glu Gly Ala Ala Cys Gly Leu Gln Glu
65                  70                  75                  80

Gly Pro Cys Gly Glu Gly Leu Gln Cys Val Val Pro Phe Gly Val Pro
                85                  90                  95

Ala Ser Ala Thr Val Arg Arg Arg Ala Gln Ala Gly Leu Cys Val Cys
            100                 105                 110

Ala Ser Ser Glu Pro Val Cys Gly Ser Asp Ala Asn Thr Tyr Ala Asn
        115                 120                 125

Leu Cys Gln Leu Arg Ala Ala Ser Arg Arg Ser Glu Arg Leu His Arg
    130                 135                 140

Pro Pro Val Ile Val Leu Gln Arg Gly Ala Cys Gly Gln Gly Gln Glu
145                 150                 155                 160

Asp Pro Asn Ser Leu Arg His Lys Tyr Asn Phe Ile Ala Asp Val Val
                165                 170                 175

Glu Lys Ile Ala Pro Ala Val Val His Ile Glu Leu Phe Arg Lys Leu
            180                 185                 190

Pro Phe Ser Lys Arg Glu Val Pro Val Ala Ser Gly Ser Gly Phe Ile
        195                 200                 205

Val Ser Glu Asp Gly Leu Ile Val Thr Asn Ala His Val Val Thr Asn
    210                 215                 220

Lys His Arg Val Lys Val Glu Leu Lys Asn Gly Ala Thr Tyr Glu Ala
225                 230                 235                 240

Lys Ile Lys Asp Val Asp Glu Lys Ala Asp Ile Ala Leu Ile Lys Ile
                245                 250                 255

Asp His Gln Gly Lys Leu Pro Val Leu Leu Leu Gly Arg Ser Ser Glu
            260                 265                 270

Leu Arg Pro Gly Glu Phe Val Val Ala Ile Gly Ser Pro Phe Ser Leu
        275                 280                 285

Gln Asn Thr Val Thr Thr Gly Ile Val Ser Thr Gln Arg Gly Gly
    290                 295                 300

Lys Glu Leu Gly Leu Arg Asn Ser Asp Met Asp Tyr Ile Gln Thr Asp
305                 310                 315                 320
```

```
Ala Ile Ile Asn Tyr Gly Asn Ser Gly Gly Pro Leu Val Asn Leu Asp
            325                 330                 335

Gly Glu Val Ile Gly Ile Asn Thr Leu Lys Val Thr Ala Gly Ile Ser
        340                 345                 350

Phe Ala Ile Pro Ser Asp Lys Ile Lys Lys Phe Leu Thr Glu Ser His
            355                 360                 365

Asp Arg Gln Ala Lys Gly Lys Ala Ile Thr Lys Lys Tyr Ile Gly
370                 375                 380

Ile Arg Met Met Ser Leu Thr Ser Ser Lys Ala Lys Glu Leu Lys Asp
385                 390                 395                 400

Arg His Arg Asp Phe Pro Asp Val Ile Ser Gly Ala Tyr Ile Ile Glu
            405                 410                 415

Val Ile Pro Asp Thr Pro Ala Glu Ala Gly Leu Lys Glu Asn Asp
            420                 425                 430

Val Ile Ile Ser Ile Asn Gly Gln Ser Val Val Ser Ala Asn Asp Val
            435                 440                 445

Ser Asp Val Ile Lys Arg Glu Ser Thr Leu Asn Met Val Val Arg Arg
    450                 455                 460

Gly Asn Glu Asp Ile Met Ile Thr Val Ile Pro Glu Glu Ile Asp Pro
465                 470                 475                 480

<210> SEQ ID NO 14
<211> LENGTH: 480
<212> TYPE: PRT
<213> ORGANISM: Mus musculus

<400> SEQUENCE: 14

Met Gln Ser Leu Arg Thr Thr Leu Leu Ser Leu Leu Leu Leu Leu Leu
1               5                   10                  15

Ala Ala Pro Ser Leu Ala Leu Pro Ser Gly Thr Gly Arg Ser Ala Pro
            20                  25                  30

Ala Ala Thr Val Cys Pro Glu His Cys Asp Pro Thr Arg Cys Ala Pro
        35                  40                  45

Pro Pro Thr Asp Cys Glu Gly Gly Arg Val Arg Asp Ala Cys Gly Cys
50                  55                  60

Cys Glu Val Cys Gly Ala Leu Glu Gly Ala Ala Cys Gly Leu Gln Glu
65                  70                  75                  80

Gly Pro Cys Gly Glu Gly Leu Gln Cys Val Val Pro Phe Gly Val Pro
            85                  90                  95

Ala Ser Ala Thr Val Arg Arg Arg Ala Gln Ala Gly Leu Cys Val Cys
            100                 105                 110

Ala Ser Ser Glu Pro Val Cys Gly Ser Asp Ala Lys Thr Tyr Thr Asn
        115                 120                 125

Leu Cys Gln Leu Arg Ala Ala Ser Arg Arg Ser Glu Lys Leu Arg Gln
    130                 135                 140

Pro Pro Val Ile Val Leu Gln Arg Gly Ala Cys Gly Gln Gly Gln Glu
145                 150                 155                 160

Asp Pro Asn Ser Leu Arg His Lys Tyr Asn Phe Ile Ala Asp Val Val
            165                 170                 175

Glu Lys Ile Ala Pro Ala Val Val His Ile Glu Leu Tyr Arg Lys Leu
        180                 185                 190

Pro Phe Ser Lys Arg Glu Val Pro Val Ala Ser Gly Ser Gly Phe Ile
    195                 200                 205

Val Ser Glu Asp Gly Leu Ile Val Thr Asn Ala His Val Val Thr Asn
```

```
            210                 215                 220
Lys Asn Arg Val Lys Val Glu Leu Lys Asn Gly Ala Thr Tyr Glu Ala
225                 230                 235                 240

Lys Ile Lys Asp Val Asp Glu Lys Ala Asp Ile Ala Leu Ile Lys Ile
                245                 250                 255

Asp His Gln Gly Lys Leu Pro Val Leu Leu Gly Arg Ser Ser Glu
                    260                 265                 270

Leu Arg Pro Gly Glu Phe Val Val Ala Ile Gly Ser Pro Phe Ser Leu
                275                 280                 285

Gln Asn Thr Val Thr Thr Gly Ile Val Ser Thr Thr Gln Arg Gly Gly
                290                 295                 300

Lys Glu Leu Gly Leu Arg Asn Ser Asp Met Asp Tyr Ile Gln Thr Asp
305                 310                 315                 320

Ala Ile Ile Asn Tyr Gly Asn Ser Gly Gly Pro Leu Val Asn Leu Asp
                    325                 330                 335

Gly Glu Val Ile Gly Ile Asn Thr Leu Lys Val Thr Ala Gly Ile Ser
                340                 345                 350

Phe Ala Ile Pro Ser Asp Lys Ile Lys Lys Phe Leu Thr Glu Ser His
                355                 360                 365

Asp Arg Gln Ala Lys Gly Lys Ala Val Thr Lys Lys Lys Tyr Ile Gly
                370                 375                 380

Ile Arg Met Met Ser Leu Thr Ser Ser Lys Ala Lys Glu Leu Lys Asp
385                 390                 395                 400

Arg His Arg Asp Phe Pro Asp Val Leu Ser Gly Ala Tyr Ile Ile Glu
                    405                 410                 415

Val Ile Pro Asp Thr Pro Ala Glu Ala Gly Gly Leu Lys Glu Asn Asp
                420                 425                 430

Val Ile Ile Ser Ile Asn Gly Gln Ser Val Val Thr Ala Asn Asp Val
                435                 440                 445

Ser Asp Val Ile Lys Lys Glu Asn Thr Leu Asn Met Val Val Arg Arg
450                 455                 460

Gly Asn Glu Asp Ile Val Ile Thr Val Ile Pro Glu Glu Ile Asp Pro
465                 470                 475                 480

<210> SEQ ID NO 15
<211> LENGTH: 459
<212> TYPE: PRT
<213> ORGANISM: Mus musculus

<400> SEQUENCE: 15

Met Gln Ala Arg Ala Leu Leu Pro Ala Thr Leu Ala Ile Leu Ala Thr
1               5                   10                  15

Leu Ala Val Leu Ala Leu Ala Arg Glu Pro Pro Ala Ala Pro Cys Pro
                20                  25                  30

Ala Arg Cys Asp Val Ser Arg Cys Pro Ser Pro Arg Cys Pro Gly Gly
                35                  40                  45

Tyr Val Pro Asp Leu Cys Asn Cys Cys Leu Val Cys Ala Ala Ser Glu
                50                  55                  60

Gly Glu Pro Cys Gly Arg Pro Leu Asp Ser Pro Cys Gly Asp Ser Leu
65                  70                  75                  80

Glu Cys Val Arg Gly Val Cys Arg Cys Arg Trp Thr His Thr Val Cys
                    85                  90                  95

Gly Thr Asp Gly His Thr Tyr Ala Asp Val Cys Ala Leu Gln Ala Ala
                100                 105                 110
```

Ser Arg Arg Ala Leu Gln Val Ser Gly Thr Pro Val Arg Gln Leu Gln
            115                 120                 125

Lys Gly Ala Cys Pro Ser Gly Leu His Gln Leu Thr Ser Pro Arg Tyr
130                 135                 140

Lys Phe Asn Phe Ile Ala Asp Val Val Glu Lys Ile Ala Pro Ala Val
145                 150                 155                 160

Val His Ile Glu Leu Phe Leu Arg His Pro Leu Phe Gly Arg Asn Val
            165                 170                 175

Pro Leu Ser Ser Gly Ser Gly Phe Ile Met Ser Glu Ala Gly Leu Ile
            180                 185                 190

Val Thr Asn Ala His Val Val Ser Ser Ser Thr Ala Ser Gly Arg
            195                 200                 205

Gln Gln Leu Lys Val Gln Leu Gln Asn Gly Asp Ala Tyr Glu Ala Thr
            210                 215                 220

Ile Gln Asp Ile Asp Lys Lys Ser Asp Ile Ala Thr Ile Val Ile His
225                 230                 235                 240

Pro Lys Lys Lys Leu Pro Val Leu Leu Leu Gly His Ser Ala Asp Leu
            245                 250                 255

Arg Pro Gly Glu Phe Val Val Ala Ile Gly Ser Pro Phe Ala Leu Gln
            260                 265                 270

Asn Thr Val Thr Thr Gly Ile Val Ser Thr Ala Gln Arg Asp Gly Lys
            275                 280                 285

Glu Leu Gly Leu Arg Asp Ser Asp Met Asp Tyr Ile Gln Thr Asp Ala
            290                 295                 300

Ile Ile Asn Tyr Gly Asn Ser Gly Gly Pro Leu Val Asn Leu Asp Gly
305                 310                 315                 320

Glu Val Ile Gly Ile Asn Thr Leu Lys Val Ala Ala Gly Ile Ser Phe
            325                 330                 335

Ala Ile Pro Ser Asp Arg Ile Thr Arg Phe Leu Ser Glu Phe Gln Asn
            340                 345                 350

Lys His Val Lys Asp Trp Lys Lys Arg Phe Ile Gly Ile Arg Met Arg
            355                 360                 365

Thr Ile Thr Pro Ser Leu Val Glu Glu Leu Lys Ala Ala Asn Pro Asp
370                 375                 380

Phe Pro Ala Val Ser Ser Gly Ile Tyr Val Gln Glu Val Val Pro Asn
385                 390                 395                 400

Ser Pro Ser Gln Arg Gly Gly Ile Gln Asp Gly Asp Ile Ile Val Lys
            405                 410                 415

Val Asn Gly Arg Pro Leu Ala Asp Ser Ser Glu Leu Gln Glu Ala Val
            420                 425                 430

Leu Asn Glu Ser Ser Leu Leu Leu Glu Val Arg Arg Gly Asn Asp Asp
            435                 440                 445

Leu Leu Phe Ser Ile Ile Pro Glu Val Val Met
            450                 455

<210> SEQ ID NO 16
<211> LENGTH: 483
<212> TYPE: PRT
<213> ORGANISM: Mus musculus

<400> SEQUENCE: 16

Met Ser Phe Gln Arg Leu Trp Ala Val Arg Thr Gln Phe Leu Leu Leu
1               5                   10                  15

Trp Leu Leu Leu Pro Ala Val Pro Val Pro Trp Ala Glu Ala Arg Arg
            20                  25                  30

```
Ser Arg Val Ser Leu Pro Cys Pro Asp Ala Cys Asp Pro Thr Arg Cys
         35                  40                  45
Pro Thr Leu Pro Thr Cys Ser Ala Gly Leu Ala Pro Val Pro Asp Arg
 50                  55                  60
Cys Gly Cys Cys Arg Val Cys Ala Ala Ala Glu Gly Gln Glu Cys Gly
 65                  70                  75                  80
Gly Ala Arg Gly Arg Pro Cys Ala Pro Arg Leu Arg Cys Gly Ala Pro
                 85                  90                  95
Phe Ser Arg Asp Pro Ser Gly Gly Ala Trp Leu Gly Thr Cys Gly Cys
                100                 105                 110
Ala Glu Gly Ala Glu Asp Ala Val Val Cys Gly Ser Asp Gly Arg Thr
             115                 120                 125
Tyr Pro Ser Leu Cys Ala Leu Arg Lys Glu Asn Arg Ala Ala Arg Gln
         130                 135                 140
Arg Gly Ala Leu Pro Ala Val Pro Val Gln Lys Gly Ala Cys Glu Glu
145                 150                 155                 160
Ala Gly Thr Thr Arg Ala Gly Arg Leu Arg Arg Lys Tyr Asn Phe Ile
                165                 170                 175
Ala Ala Val Val Glu Lys Val Ala Pro Ser Val Val His Leu Gln Leu
             180                 185                 190
Phe Arg Arg Ser Pro Leu Thr Asn Gln Glu Ile Pro Ser Ser Ser Gly
         195                 200                 205
Ser Gly Phe Ile Val Ser Glu Asp Gly Leu Ile Val Thr Asn Ala His
     210                 215                 220
Val Leu Thr Asn Gln Gln Lys Ile Gln Val Glu Leu Gln Ser Gly Ala
225                 230                 235                 240
Arg Tyr Glu Ala Thr Val Lys Asp Ile Asp His Lys Leu Asp Leu Ala
                245                 250                 255
Leu Ile Lys Ile Glu Pro Asp Thr Glu Leu Pro Val Leu Leu Leu Gly
             260                 265                 270
Arg Ser Ser Asp Leu Arg Ala Gly Glu Phe Val Val Ala Leu Gly Ser
         275                 280                 285
Pro Phe Ser Leu Gln Asn Thr Val Thr Ala Gly Ile Val Ser Thr Thr
     290                 295                 300
Gln Arg Gly Gly Arg Glu Leu Gly Leu Lys Asn Ser Asp Ile Asp Tyr
305                 310                 315                 320
Ile Gln Thr Asp Ala Ile Ile Asn His Gly Asn Ser Gly Gly Pro Leu
                325                 330                 335
Val Asn Leu Asp Gly Asp Val Ile Gly Ile Asn Thr Leu Lys Val Thr
             340                 345                 350
Ala Gly Ile Ser Phe Ala Ile Pro Ser Asp Arg Ile Arg Gln Phe Leu
         355                 360                 365
Glu Asp Tyr His Glu Arg Gln Leu Lys Gly Lys Ala Pro Leu Gln Lys
     370                 375                 380
Lys Tyr Leu Gly Leu Arg Met Leu Pro Leu Thr Leu Asn Leu Leu Gln
385                 390                 395                 400
Glu Met Lys Arg Gln Asp Pro Glu Phe Pro Asp Val Ser Ser Gly Val
                405                 410                 415
Phe Val Tyr Glu Val Ile Gln Gly Ser Ala Ala Ser Ser Gly Leu
             420                 425                 430
Arg Asp His Asp Val Ile Val Ser Ile Asn Gly Gln Pro Val Thr Thr
         435                 440                 445
```

```
Thr Thr Asp Val Ile Glu Ala Val Lys Asp Asn Asp Phe Leu Ser Ile
        450                 455                 460

Ile Val Leu Arg Gly Ser Gln Thr Leu Phe Leu Thr Val Thr Pro Glu
465                 470                 475                 480

Ile Ile Asn

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Trp Val Arg Gln Ala Pro Gly Lys Gly Leu Glu Trp Val Gly
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ala Ser Gln Ser Ile Asn Thr Tyr Leu Ala
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Gln Ser Asp Asp Thr Pro Pro Thr
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Phe Ser Ile Ser Gly Tyr Tyr Ile His
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Ala Ser Gln Val Val Gly Asn Tyr Leu Ala
1               5                   10
```

```
<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Gln Ser Asp Asp His Pro Pro Thr
1               5

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      Consensus peptide
<220> FEATURE:
<221> NAME/KEY: MOD_RES
<222> LOCATION: (5)..(5)
<223> OTHER INFORMATION: Asp, Ser or Val
<220> FEATURE:
<221> NAME/KEY: MOD_RES
<222> LOCATION: (6)..(6)
<223> OTHER INFORMATION: Val or Ile
<220> FEATURE:
<221> NAME/KEY: MOD_RES
<222> LOCATION: (7)..(7)
<223> OTHER INFORMATION: Ser, Asn or Gly
<220> FEATURE:
<221> NAME/KEY: MOD_RES
<222> LOCATION: (8)..(8)
<223> OTHER INFORMATION: Thr or Asn
<220> FEATURE:
<221> NAME/KEY: MOD_RES
<222> LOCATION: (9)..(9)
<223> OTHER INFORMATION: Ala or Tyr
<220> FEATURE:
<221> NAME/KEY: MOD_RES
<222> LOCATION: (10)..(10)
<223> OTHER INFORMATION: Val or Leu

<400> SEQUENCE: 23

Arg Ala Ser Gln Xaa Xaa Xaa Xaa Xaa Xaa Ala
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      Consensus peptide
<220> FEATURE:
<221> NAME/KEY: MOD_RES
<222> LOCATION: (3)..(3)
<223> OTHER INFORMATION: Ser, Val or Asp
<220> FEATURE:
<221> NAME/KEY: MOD_RES
<222> LOCATION: (4)..(4)
<223> OTHER INFORMATION: Tyr, Asp or Ser
<220> FEATURE:
<221> NAME/KEY: MOD_RES
<222> LOCATION: (5)..(5)
<223> OTHER INFORMATION: Thr, Ser, Ala, Asp or Asn
<220> FEATURE:
<221> NAME/KEY: MOD_RES
<222> LOCATION: (6)..(6)
<223> OTHER INFORMATION: Thr, His, Asn, Ser, Ala, Leu or Arg
<220> FEATURE:
<221> NAME/KEY: MOD_RES
<222> LOCATION: (8)..(8)
<223> OTHER INFORMATION: Pro, Thr, Ala or Ser
```

<400> SEQUENCE: 24

Gln Gln Xaa Xaa Xaa Xaa Pro Xaa Thr
1               5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      Consensus peptide
<220> FEATURE:
<221> NAME/KEY: MOD_RES
<222> LOCATION: (3)..(3)
<223> OTHER INFORMATION: Asn, Ser or Thr
<220> FEATURE:
<221> NAME/KEY: MOD_RES
<222> LOCATION: (5)..(5)
<223> OTHER INFORMATION: Ser, Asp, Tyr or Ala
<220> FEATURE:
<221> NAME/KEY: MOD_RES
<222> LOCATION: (6)..(6)
<223> OTHER INFORMATION: Gly or Asp

<400> SEQUENCE: 25

Gly Phe Xaa Ile Xaa Xaa Tyr Tyr Ile His
1               5                   10

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      Consensus peptide
<220> FEATURE:
<221> NAME/KEY: MOD_RES
<222> LOCATION: (10)..(10)
<223> OTHER INFORMATION: Asn or Asp

<400> SEQUENCE: 26

Trp Ile Asp Pro Tyr Gly Gly Asp Thr Xaa Tyr Ala Asp Ser Val Lys
1               5                   10                  15

Gly

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      Consensus peptide
<220> FEATURE:
<221> NAME/KEY: MOD_RES
<222> LOCATION: (6)..(6)
<223> OTHER INFORMATION: Ser or Thr

<400> SEQUENCE: 27

Gly Thr Phe Leu Thr Xaa Trp Gly His Tyr Phe Asp Tyr
1               5                   10

<210> SEQ ID NO 28
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 28

Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Asn Thr Tyr
            20                  25                  30

Leu Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Thr Pro Pro
                85                  90                  95

Thr Phe Gly Gln Gly Thr Lys Val Glu Ile Lys Arg
            100                 105

<210> SEQ ID NO 29
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Ile Ser Gly Tyr
            20                  25                  30

Tyr Ile His Trp Val Arg Gln Ala Pro Gly Lys Gly Leu Glu Trp Val
        35                  40                  45

Gly Trp Ile Asp Pro Tyr Gly Gly Asp Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Thr Phe Leu Thr Ser Trp Gly His Tyr Phe Asp Tyr Trp
            100                 105                 110

Gly Gln Gly Thr
        115

<210> SEQ ID NO 30
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Pro Ser Leu Ser Ala Ser Val Gly
1               5                   10                  15

Asp Arg Val Thr Ile Thr Cys Arg Ala Ser Gln Val Val Gly Asn Tyr
            20                  25                  30

Leu Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
```

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asp His Pro Pro
                 85                  90                  95

Thr Phe Gly Gln Gly Thr Lys Val Glu Ile Lys Arg
            100                 105

<210> SEQ ID NO 31
<211> LENGTH: 108
<212> TYPE: PRT
<213> ORGANISM: Artificial Sequence
<220> FEATURE:
<223> OTHER INFORMATION: Description of Artificial Sequence: Synthetic
      Consensus polypeptide
<220> FEATURE:
<221> NAME/KEY: MOD_RES
<222> LOCATION: (28)..(28)
<223> OTHER INFORMATION: Asp, Ser or Val
<220> FEATURE:
<221> NAME/KEY: MOD_RES
<222> LOCATION: (29)..(29)
<223> OTHER INFORMATION: Val or Ile
<220> FEATURE:
<221> NAME/KEY: MOD_RES
<222> LOCATION: (30)..(30)
<223> OTHER INFORMATION: Ser, Asn or Gly
<220> FEATURE:
<221> NAME/KEY: MOD_RES
<222> LOCATION: (31)..(31)
<223> OTHER INFORMATION: Thr or Asn
<220> FEATURE:
<221> NAME/KEY: MOD_RES
<222> LOCATION: (32)..(32)
<223> OTHER INFORMATION: Ala or Tyr
<220> FEATURE:
<221> NAME/KEY: MOD_RES
<222> LOCATION: (33)..(33)
<223> OTHER INFORMATION: Val or Leu
<220> FEATURE:
<221> NAME/KEY: MOD_RES
<222> LOCATION: (91)..(91)
<223> OTHER INFORMATION: Ser, Val or Asp
<220> FEATURE:
<221> NAME/KEY: MOD_RES
<222> LOCATION: (92)..(92)
<223> OTHER INFORMATION: Tyr, Asp or Ser
<220> FEATURE:
<221> NAME/KEY: MOD_RES
<222> LOCATION: (93)..(93)
<223> OTHER INFORMATION: Thr, Ser, Ala, Asp or Asn
<220> FEATURE:
<221> NAME/KEY: MOD_RES
<222> LOCATION: (94)..(94)
<223> OTHER INFORMATION: Thr, His, Asn, Ser, Ala, Leu or Arg
<220> FEATURE:
<221> NAME/KEY: MOD_RES
<222> LOCATION: (96)..(96)
<223> OTHER INFORMATION: Pro, Thr, Ala or Ser

<400> SEQUENCE: 31

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Xaa Xaa Xaa Xaa Xaa
                 20                  25                  30

Xaa Ala Trp Tyr Gln Gln Lys Pro Gly Lys Ala Pro Lys Leu Leu Ile
                 35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
```

```
                    65                  70                  75                  80
Glu Asp Phe Ala Thr Tyr Tyr Cys Gln Gln Xaa Xaa Xaa Xaa Pro Xaa
                85                  90                  95

Thr Phe Gly Gln Gly Thr Lys Val Glu Ile Lys Arg
                100                 105

<210> SEQ ID NO 32
<211> LENGTH: 116
<212> TYPE: PRT
<213> ORGANISM: Artificial Sequence
<220> FEATURE:
<223> OTHER INFORMATION: Description of Artificial Sequence: Synthetic
      Consensus polypeptide
<220> FEATURE:
<221> NAME/KEY: MOD_RES
<222> LOCATION: (28)..(28)
<223> OTHER INFORMATION: Asn, Ser or Thr
<220> FEATURE:
<221> NAME/KEY: MOD_RES
<222> LOCATION: (30)..(30)
<223> OTHER INFORMATION: Ser, Asp, Tyr or Ala
<220> FEATURE:
<221> NAME/KEY: MOD_RES
<222> LOCATION: (31)..(31)
<223> OTHER INFORMATION: Gly or Asp
<220> FEATURE:
<221> NAME/KEY: MOD_RES
<222> LOCATION: (59)..(59)
<223> OTHER INFORMATION: Asn or Asp
<220> FEATURE:
<221> NAME/KEY: MOD_RES
<222> LOCATION: (104)..(104)
<223> OTHER INFORMATION: Ser or Thr

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Xaa Ile Xaa Xaa Tyr
                20                  25                  30

Tyr Ile His Trp Val Arg Gln Ala Pro Gly Lys Gly Leu Glu Trp Val
                35                  40                  45

Gly Trp Ile Asp Pro Tyr Gly Gly Asp Thr Xaa Tyr Ala Asp Ser Val
            50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Thr Phe Leu Thr Xaa Trp Gly His Tyr Phe Asp Tyr Trp
                100                 105                 110

Gly Gln Gly Thr
            115

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ala Ser Gln Asp Val Gly Thr Tyr Leu Ala
1               5                   10

<210> SEQ ID NO 34
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Gln Val Tyr Ser His Pro Pro Thr
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Gln Ser Tyr Thr Asn Pro Pro Thr
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Gln Ser Tyr Ala Thr Pro Thr Thr
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Gln Ser Tyr Ser Ser Pro Ala Thr
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Gln Val Tyr Thr Thr Pro Pro Thr
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39
```

```
Gln Gln Val Tyr Ala Thr Pro Ser Thr
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Gln Ser Tyr Asn Ser Pro Ala Thr
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Gln Ser Tyr Ser Thr Pro Ala Thr
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Gln Ser Tyr Thr Ala Pro Thr Thr
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Gln Asp Ser Thr Leu Pro Pro Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Gln Ser Asp Ala Ala Pro Pro Thr
1               5

<210> SEQ ID NO 45
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 45

Gln Gln Ser Tyr Ser Thr Pro Pro Thr
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Gln Ser Tyr Thr Arg Pro Pro Thr
1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Phe Ser Ile Ser Asp Tyr Tyr Ile His
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Phe Ser Ile Asp Gly Tyr Tyr Ile His
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Phe Thr Ile Tyr Asp Tyr Tyr Ile His
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Phe Ser Ile Ala Gly Tyr Tyr Ile His
1               5                   10
```

```
<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Phe Thr Ile Ser Asp Tyr Tyr Ile His
1               5                   10

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Trp Ile Asp Pro Tyr Gly Gly Asp Thr Asp Tyr Ala Asp Ser Val Lys
1               5                   10                  15

Gly

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Thr Phe Leu Thr Thr Trp Gly His Tyr Phe Asp Tyr
1               5                   10

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Val Ser Thr Ala Val
1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Ile Asn Thr Tyr Leu
1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 56

Asp Val Gly Thr Tyr Leu
1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Val Val Gly Asn Tyr Leu
1               5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Ala Ser Phe Leu Tyr
1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Tyr Thr Thr Pro Pro
1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Val Tyr Ser His Pro Pro
1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Tyr Thr Asn Pro Pro
1               5

<210> SEQ ID NO 62
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ser Tyr Ala Thr Pro Thr
1               5

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ser Asp Asp Thr Pro Pro
1               5

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ser Tyr Ser Ser Pro Ala
1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Val Tyr Thr Thr Pro Pro
1               5

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Val Tyr Ala Thr Pro Ser
1               5

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ser Tyr Asn Ser Pro Ala
```

```
1               5

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Tyr Ser Thr Pro Ala
1               5

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser Tyr Thr Ala Pro Thr
1               5

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Ser Thr Leu Pro Pro
1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Asp Ala Ala Pro Pro
1               5

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ser Asp Asp His Pro Pro
1               5

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
                          peptide

<400> SEQUENCE: 73

Ser Tyr Ser Thr Pro Pro
1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Tyr Thr Arg Pro Pro
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Phe Ser Ile Ser Gly Tyr Tyr
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Phe Ser Ile Ser Asp Tyr Tyr
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Phe Ser Ile Asp Gly Tyr Tyr
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Phe Thr Ile Tyr Asp Tyr Tyr
1               5

<210> SEQ ID NO 79
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Phe Ser Ile Ala Gly Tyr Tyr
1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Phe Thr Ile Ser Asp Tyr Tyr
1               5

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Trp Ile Asp Pro Tyr Gly Gly Asp Thr Asn
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Trp Ile Asp Pro Tyr Gly Gly Asp Thr Asp
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Thr Phe Leu Thr Ser Trp Gly His Tyr
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84
```

```
Gly Thr Phe Leu Thr Thr Trp Gly His Tyr
1               5                   10
```

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, Ser or Val
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
<222> LOCATION: (3)..(3)
<223> OTHER INFORMATION: Ser, Asn or Gly
<220> FEATURE:
<221> NAME/KEY: MOD_RES
<222> LOCATION: (4)..(4)
<223> OTHER INFORMATION: Thr or Asn
<220> FEATURE:
<221> NAME/KEY: MOD_RES
<222> LOCATION: (5)..(5)
<223> OTHER INFORMATION: Ala or Tyr
<220> FEATURE:
<221> NAME/KEY: MOD_RES
<222> LOCATION: (6)..(6)
<223> OTHER INFORMATION: Val or Leu

<400> SEQUENCE: 85

```
Xaa Xaa Xaa Xaa Xaa Xaa
1               5
```

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Val or Asp
<220> FEATURE:
<221> NAME/KEY: MOD_RES
<222> LOCATION: (2)..(2)
<223> OTHER INFORMATION: Tyr, Asp or Ser
<220> FEATURE:
<221> NAME/KEY: MOD_RES
<222> LOCATION: (3)..(3)
<223> OTHER INFORMATION: Thr, Ser, Ala, Asp or Asn
<220> FEATURE:
<221> NAME/KEY: MOD_RES
<222> LOCATION: (4)..(4)
<223> OTHER INFORMATION: Thr, His, Asn, Ser, Ala, Leu or Arg
<220> FEATURE:
<221> NAME/KEY: MOD_RES
<222> LOCATION: (6)..(6)
<223> OTHER INFORMATION: Pro, Thr, Ala or Ser

<400> SEQUENCE: 86

```
Xaa Xaa Xaa Xaa Pro Xaa
1               5
```

<210> SEQ ID NO 87
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asn, Ser or Thr
<220> FEATURE:
<221> NAME/KEY: MOD_RES
<222> LOCATION: (5)..(5)
<223> OTHER INFORMATION: Ser, Asp, Tyr or Ala
<220> FEATURE:
<221> NAME/KEY: MOD_RES
<222> LOCATION: (6)..(6)
<223> OTHER INFORMATION: Gly or Asp

<400> SEQUENCE: 87

Gly Phe Xaa Ile Xaa Xaa Tyr Tyr
1               5

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Asn or Asp

<400> SEQUENCE: 88

Trp Ile Asp Pro Tyr Gly Gly Asp Thr Xaa
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser or Thr

<400> SEQUENCE: 89

Gly Thr Phe Leu Thr Xaa Trp Gly His Tyr
1               5                   10

<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 90

His His His His His His
1               5
```

What is claimed is:

1. An isolated monoclonal antibody that binds to HtrA1, wherein the antibody comprises the following six hypervariable regions (HVRs):
   an HVR-H1 comprising the amino acid sequence of SEQ ID NO: 4;
   an HVR-H2 comprising the amino acid sequence of SEQ ID NO: 5;
   an HVR-H3 comprising the amino acid sequence of SEQ ID NO: 6;
   an HVR-L1 comprising the amino acid sequence of SEQ ID NO: 1;

an HVR-L2 comprising the amino acid sequence of SEQ ID NO: 2; and
an HVR-L3 comprising the amino acid sequence of SEQ ID NO: 3.

2. The antibody of claim 1, comprising (a) a VH sequence having at least 95% sequence identity to the amino acid sequence of SEQ ID NO: 8; (b) a VL sequence having at least 95% sequence identity to the amino acid sequence of SEQ ID NO: 7; or (c) a VH sequence as in (a) and a VL sequence as in (b).

3. The antibody of claim 2, comprising (a) a VH sequence of SEQ ID NO: 8; (b) a VL sequence of SEQ ID NO: 7; or (c) a VH sequence as in (a) and a VL sequence as in (b).

4. The antibody of claim 1, wherein the antibody is a human antibody, a humanized antibody, or a chimeric antibody.

5. The antibody of claim 1, wherein the antibody is an antibody fragment that binds to HtrA1.

6. An immunoconjugate comprising the antibody of claim 1 and a cytotoxic agent.

7. A pharmaceutical formulation comprising the antibody of claim 1 and a pharmaceutically acceptable carrier.

8. An isolated monoclonal antibody that binds to HtrA1, wherein the antibody comprises the following six hypervariable regions (HVRs):
    an HVR-H1 comprising the amino acid sequence of SEQ ID NO: 20;
    an HVR-H2 comprising the amino acid sequence of SEQ ID NO: 5;
    an HVR-H3 comprising the amino acid sequence of SEQ ID NO: 6;
    an HVR-L1 comprising the amino acid sequence of SEQ ID NO: 1;
    an HVR-L2 comprising the amino acid sequence of SEQ ID NO: 2; and
    an HVR-L3 comprising the amino acid sequence of SEQ ID NO: 3.

9. The antibody of claim 8, comprising (a) a VH sequence having at least 95% sequence identity to the amino acid sequence of SEQ ID NO: 29; (b) a VL sequence having at least 95% sequence identity to the amino acid sequence of SEQ ID NO: 7; or (c) a VH sequence as in (a) and a VL sequence as in (b).

10. The antibody of claim 9, comprising (a) a VH sequence of SEQ ID NO: 29; (b) a VL sequence of SEQ ID NO: 7; or (c) a VH sequence as in (a) and a VL sequence as in (b).

11. The antibody of claim 8, wherein the antibody is a human antibody, a humanized antibody, or a chimeric antibody.

12. The antibody of claim 8, wherein the antibody is an antibody fragment that binds to HtrA1.

13. An immunoconjugate comprising the antibody of claim 8 and a cytotoxic agent.

14. A pharmaceutical formulation comprising the antibody of claim 8 and a pharmaceutically acceptable carrier.

15. An isolated monoclonal antibody that binds to HtrA1, wherein the antibody comprises the following six hypervariable regions (HVRs):
    an HVR-H1 comprising the amino acid sequence of SEQ ID NO: 20;
    an HVR-H2 comprising the amino acid sequence of SEQ ID NO: 5;
    an HVR-H3 comprising the amino acid sequence of SEQ ID NO: 6;
    an HVR-L1 comprising the amino acid sequence of SEQ ID NO: 18;
    an HVR-L2 comprising the amino acid sequence of SEQ ID NO: 2; and
    an HVR-L3 comprising the amino acid sequence of SEQ ID NO: 19.

16. The antibody of claim 15, comprising (a) a VH sequence having at least 95% sequence identity to the amino acid sequence of SEQ ID NO: 29; (b) a VL sequence having at least 95% sequence identity to the amino acid sequence of SEQ ID NO: 28; or (c) a VH sequence as in (a) and a VL sequence as in (b).

17. The antibody of claim 16, comprising (a) a VH sequence of SEQ ID NO: 29; (b) a VL sequence of SEQ ID NO: 28; or (c) a VH sequence as in (a) and a VL sequence as in (b).

18. The antibody of claim 15, wherein the antibody is a human antibody, a humanized antibody, or a chimeric antibody.

19. The antibody of claim 15, wherein the antibody is an antibody fragment that binds to HtrA1.

20. An immunoconjugate comprising the antibody of claim 15 and a cytotoxic agent.

21. A pharmaceutical formulation comprising the antibody of claim 15 and a pharmaceutically acceptable carrier.

22. An isolated monoclonal antibody that binds to HtrA1, wherein the antibody comprises the following six hypervariable regions (HVRs):
    an HVR-H1 comprising the amino acid sequence of SEQ ID NO: 20;
    an HVR-H2 comprising the amino acid sequence of SEQ ID NO: 5;
    an HVR-H3 comprising the amino acid sequence of SEQ ID NO: 6;
    an HVR-L1 comprising the amino acid sequence of SEQ ID NO: 21;
    an HVR-L2 comprising the amino acid sequence of SEQ ID NO: 2; and
    an HVR-L3 comprising the amino acid sequence of SEQ ID NO: 22.

23. The antibody of claim 22, comprising (a) a VH sequence having at least 95% sequence identity to the amino acid sequence of SEQ ID NO: 29; (b) a VL sequence having at least 95% sequence identity to the amino acid sequence of SEQ ID NO: 30; or (c) a VH sequence as in (a) and a VL sequence as in (b).

24. The antibody of claim 23, comprising (a) a VH sequence of SEQ ID NO: 29; (b) a VL sequence of SEQ ID NO: 30; or (c) a VH sequence as in (a) and a VL sequence as in (b).

25. The antibody of claim 22, wherein the antibody is a human antibody, a humanized antibody, or a chimeric antibody.

26. The antibody of claim 22, wherein the antibody is an antibody fragment that binds to HtrA1.

27. An immunoconjugate comprising the antibody of claim 22 and a cytotoxic agent.

28. A pharmaceutical formulation comprising the antibody of claim 22 and a pharmaceutically acceptable carrier.

29. An isolated monoclonal antibody that binds to HtrA1, wherein the antibody comprises the amino acid sequences of any one of the following sets of six HRV-H1, HVR-H2, HVR-H3, HVR-L1, HVR-L2, and HVR-L3 sequences, respectively:
    SEQ ID NOs: 20, 5, 6, 1, 2, and 34;
    SEQ ID NOs: 47, 5, 6, 1, 2, and 35;
    SEQ ID NOs: 20, 5, 6, 1, 2, and 36;
    SEQ ID NOs: 48, 5, 6, 1, 2, and 3;
    SEQ ID NOs: 47, 5, 6, 1, 2, and 37;

SEQ ID NOs: 49, 5, 6, 1, 2, and 3;
SEQ ID NOs: 20, 5, 6, 1, 2, and 38;
SEQ ID NOs: 20, 5, 6, 1, 2, and 39;
SEQ ID NOs: 20, 52, 6, 1, 2, and 40;
SEQ ID NOs: 20, 5, 53, 1, 2, and 41;
SEQ ID NOs: 20, 52, 6, 1, 2, and 3;
SEQ ID NOs: 47, 5, 6, 1, 2, and 42;
SEQ ID NOs: 20, 5, 6, 33, 2, and 43;
SEQ ID NOs: 20, 5, 6, 1, 2, and 44;
SEQ ID NOs: 20, 5, 53, 1, 2, and 3;
SEQ ID NOs: 50, 5, 6, 1, 2, and 45;
SEQ ID NOs: 51, 5, 6, 1, 2, and 3; or
SEQ ID NOs: 20, 52, 6, 1, 2, and 46.

30. The antibody of claim 29, wherein the antibody is a human antibody, a humanized antibody, or a chimeric antibody.

31. The antibody of claim 29, wherein the antibody is an antibody fragment that binds to HtrA1.

32. An immunoconjugate comprising the antibody of claim 29 and a cytotoxic agent.

33. A pharmaceutical formulation comprising the antibody of claim 29 and a pharmaceutically acceptable carrier.

\* \* \* \* \*

UNITED STATES PATENT AND TRADEMARK OFFICE
CERTIFICATE OF CORRECTION

PATENT NO. : 9,738,727 B2
APPLICATION NO. : 13/651289
DATED : August 22, 2017
INVENTOR(S) : Yan Wu et al.

It is certified that error appears in the above-identified patent and that said Letters Patent is hereby corrected as shown below:

On the Title Page

Under Inventors, replace "Menno van Lookeren-Campagne" with --Menno van Lookeren Campagne--.

Page 2, under OTHER PUBLICATIONS, in Cariello et al., replace "The mutiple" with --The multiple--.

Page 3, under OTHER PUBLICATIONS, in Levin, replace "The occurence" with --The occurrence--.

In the Specification

Column 7, Line 13, replace "protease activityin" with --protease activity in--.

Column 14, Line 46, replace "or consistingof amino" with --or consisting of amino--.

Column 24, Line 22, replace "equipped spectrophometer" with --equipped spectrophotometer--.

Column 35, Line 11, replace "from degredation," with --from degradation,--.

Column 36, Line 28, replace "The immunuoconjugates" with --The immunoconjugates--.

Column 38, Line 53, replace "may be slected" with --may be selected--.

Column 41, Line 6, replace "with photdynamic" with --with photodynamic--.

Column 43, in Light chain VR for Anti-HtrA1 Antibody YW505.94, replace "YS<u>ASFLYSG</u>" with --Y<u>SASFLYSG</u>--.

Signed and Sealed this
Twenty-seventh Day of March, 2018

Andrei Iancu
*Director of the United States Patent and Trademark Office*

CERTIFICATE OF CORRECTION (continued)
U.S. Pat. No. 9,738,727 B2

Column 45, in Consensus Heavy Chain VR, replace "GF$X_l X_m X_n$YYIH" with --GF$X_l I X_m X_n$YYIH--.

Column 48, Line 37, replace "of Carbenicilin." with --of Carbenicillin.--;
　　　Line 40, replace "with Carbenicilin" with --with Carbenicillin--.

Column 50, Line 37, replace "a microfludizer" with --a microfluidizer--;
　　　Line 58, replace "(Mca-IRRVSYSF(" with --(Mca-IRR$\underline{V}$SYSF(--;
　　　Line 66, replace "triisoproplysilane" with --triisopropylsilane--.

Column 51, Line 63, replace "inhibitory potenciesof" with --inhibitory potencies of--.

Column 53, Lines 1-3, replace "the concentrations of MuHtrA1_PD, MuHtrA3_PD and MuHtrA4_PD 6 nM, 20 nM and 20 nM, respectively," with --the concentrations of MuHtrA1_PD, MuHtrA3_PD and MuHtrA4_PD were 6 nM, 20 nM, and 20 nM, respectively,--;
　　　Line 34, replace "300 μl/min" with --30 μl/min--.

Column 54, Line 55, replace "5200" with --S200--.

Column 55, Line 18, replace "210, 100 Da" with --210,100 Da--;
　　　Line 25, replace "618, 600 Da" with --618,600 Da--;
　　　Line 50, replace "pWO703," with --PW0703,--.

Column 56, Line 21, replace "termperature" with --temperature--;
　　　Line 55, replace "gently shacken" with --gently shaken--.

Column 57, Line 59, replace "300 min" with --30 μl/min--.

Column 59, Line 25, replace "homoginization." with --homogenization--;
　　　Line 41, replace "are are" with --are--.

Column 60, Line 49, replace "contant light" with --constant light--.